US006562618B1

(12) United States Patent
Tamatani et al.

(10) Patent No.: US 6,562,618 B1
(45) Date of Patent: May 13, 2003

(54) MONOCLONAL ANTIBODY AGAINST CONNECTIVE TISSUE GROWTH FACTOR AND MEDICINAL USES THEREOF

(75) Inventors: Takuya Tamatani, Kanagawa (JP); Katsunari Tezuka, Kanagawa (JP); Shinji Sakamoto, Kanagawa (JP); Masaharu Takigawa, Okayama (JP)

(73) Assignees: Japan Tobacco, Inc., Tokyo (JP); Nichirei Corporation, Tokyo (JP)

( * ) Notice: Subject to any disclaimer, the term of this patent is extended or adjusted under 35 U.S.C. 154(b) by 0 days.

(21) Appl. No.: 09/582,337

(22) PCT Filed: Dec. 16, 1998

(86) PCT No.: PCT/JP98/05697

§ 371 (c)(1),
(2), (4) Date: Sep. 18, 2000

(87) PCT Pub. No.: WO99/33878

PCT Pub. Date: Jul. 8, 1999

(30) Foreign Application Priority Data

Dec. 25, 1997 (JP) .............................................. 9-367699
Dec. 15, 1998 (JP) ............................................ 10-356183

(51) Int. Cl.$^7$ ........................ C07K 16/22; C07K 21/08; A61K 49/16; C12N 5/12
(52) U.S. Cl. ............... 435/326; 530/385.15; 530/387.3; 530/391.1; 530/391.3; 530/388.24; 424/133.1; 424/135.1; 424/145.1; 435/70.21; 435/328; 435/346; 435/810
(58) Field of Search ..................... 530/388.15, 388.24, 530/391.1, 391.3, 387.3; 435/326, 346, 70.21, 810, 328; 424/133.1, 135.1, 145.1

(56) References Cited

U.S. PATENT DOCUMENTS

| | | | |
|---|---|---|---|
| 5,408,040 A | | 4/1995 | Grotendorst et al. |
| 5,783,187 A | | 7/1998 | Grotendorst et al. |
| 6,107,049 A | * | 8/2000 | Allard et al. |
| 6,175,057 B1 | * | 1/2001 | Mucke et al. |

FOREIGN PATENT DOCUMENTS

| WO | WO 96/38172 | 12/1996 |
|---|---|---|
| WO | WO 99/07407 | 2/1999 |

OTHER PUBLICATIONS

Kuby et al., 1994, Immunology, second edition, pp. 85–96.*
Harlow et al in Antibodies a Laboratory Manual, 1988, Cold Spring harbor laboratory publication, Cold Spring Harbor, NY, pp. 139–149.*
Bradham et al., *The Journal of Cell Biology*, 114(6):1285–1294 (Sep. 1991).
Brigstock et al., *The Journal of Biological Chemistry*, 272(32):20275–20282 (1997).
Frazier et al., *Int. J. Biochem. Cell Biol.*, 29(1):153–161 (1997).
Grotendorst et al., *Cell Growth & Differentiation*, 7:469–480 (Apr. 1996).
Hammes et al., *Kidney International*, 48:501–509 (1995).
Igarashi et al., *The Journal of Investigative Dermatology*, 105(2):280–284 (Aug. 1995).
Igarashi et al., *The Journal of Investigative Dermatology*, 106(4):729–733 (Apr. 1996).
Kikuchi et al., *The Journal of Investigative Dermatology*, 105:128–132 (Jul. 1995).
Kireeva et al., *Experimental Cell Research*, 233:63–77 (1997).
Kothapalli et al., *Cell Growth & Differentiation*, 8:61–68 (Jan. 1997).
Mendez et al., *Nature Genetics*, 15:146–156 (Feb. 1997).
Oemar et al., *Circulation*, 95(4):831–839 (Feb. 18, 1997).
Pawar et al., *Journal of Cellular Physiology*, 165:556–565 (1995).
Ryseck et al., *Cell Growth & Differentiation*, 2:225–233 (May 1991).
Steffen et al.. *Growth Factors*, 15:199–213 (1998).

* cited by examiner

Primary Examiner—Christina Chan
Assistant Examiner—Phuong N. Huynh
(74) Attorney, Agent, or Firm—Karl Bozicevic; James S. Keddie; Bozicevic, Field & Francis LLP

(57) ABSTRACT

A human monoclonal antibody useful for the treatment of various diseases caused by human connective tissue growth factor (CTGF) and preventing the onset of the above diseases; medicinal uses thereof; and various monoclonal antibodies having various characteristics against various mammalian CTGFs useful for detecting and assaying CTGFs present in body fluids of mammals suffering from various diseases.

17 Claims, 25 Drawing Sheets

Fig. 1

| Clone Name | Immunized Animal | Antigen | Isotype | Crossreactivity Human | Crossreactivity Mouse | Crossreactivity Rat | Reactivity to Tissues from Arteriosclerotic Lesions in WHHL rabbit | Activity of Inhibiting the Binding of 293 Cells |
|---|---|---|---|---|---|---|---|---|
| A4.3 | human antibody-producing mouse | human CTGF | G2 · κ | ○○○ | ○○○ | ○○○ | ○ | ○ |
| A11.1 | human antibody-producing mouse | human CTGF | G2 · κ | ○○○ | ○△× | ○×× | ○ | ○ |
| A15.1 | human antibody-producing mouse | human CTGF | G2 · κ | ○○○ | ○△× | ×× | | ○ |
| A29.6 | human antibody-producing mouse | human CTGF | G2 · κ | ○○○ | ○×× | ×× | ○ | ○ |
| B13.7 | human antibody-producing mouse | human CTGF | G2 · κ | ○○○ | ○○× | △×× | | × |
| B22.2 | human antibody-producing mouse | human CTGF | G2 · κ | ○○○ | ○○○ | ○○○ | | × |
| B29.6 | human antibody-producing mouse | human CTGF | G2 · κ | ○△× | ○×× | △×× | × | × |
| B35.1 | human antibody-producing mouse | human CTGF | G2 · κ | ○○○ | ○○○ | ○○○ | × | ○ |
| C2.1 | human antibody-producing mouse | human CTGF | G2 · κ | ○○○ | ○△× | ○△× | ○ | × |
| C26.11 | human antibody-producing mouse | human CTGF | G2 · κ | ○○○ | ○△× | ○△× | | ○ |
| C59.1 | human antibody-producing mouse | human CTGF | G2 · κ | ○○○ | ○○× | ○×× | | × |
| C114.4 | human antibody-producing mouse | human CTGF | G2 · κ | ○○△ | ○○○ | ○○△ | ○ | ○ |
| 8-64-6 | normal mouse | human CTGF | G1 · κ | ○○○ | ○×× | ○○△ | | ○ |
| 8-86-2 | normal mouse | human CTGF | G1 · κ | ○○△ | ○△× | ○△× | × | ○ |
| 8-97-3 | normal mouse | human CTGF | G1 · κ | ○○△ | ○△× | ○△× | | × |
| 8-149-3 | normal mouse | human CTGF | G1 · κ | ○○○ | ○○○ | ○○△ | × | × |
| 15-38-1 | normal mouse | human CTGF | G1 · κ | ○○△ | ○○△ | ○○△ | | |
| 13-51-2 | normal rat | mouse CTGF | | ××× | ○△× | ○○○ | ○ | × |
| 17-132 | normal rat | mouse CTGF | | ○○△ | ○○○ | ○○○ | | ○ |
| 23-96 | normal rat | mouse CTGF | | ××× | ○○○ | ○×× | | × |
| 24-53 | normal rat | mouse CTGF | | ○○○ | ○○○ | ○○△ | | × |
| 24-67 | normal rat | mouse CTGF | | ××× | ○○○ | ○○△ | | × |
| 25-91 | normal rat | mouse CTGF | | ××× | ○△× | △×× | | × |
| 25-101 | normal rat | mouse CTGF | | ××× | ○△× | ○○○ | | × |
| 25-256 | normal rat | mouse CTGF | | ××× | ○○○ | ○×× | | × |
| 25-338 | normal rat | mouse CTGF | | ××× | ○○○ | ○○○ | | × |
| 25-410 | normal rat | mouse CTGF | | ××× | ○○○ | ○△× | | × |
| 25-463 | normal rat | mouse CTGF | | ××× | ○○△ | ○△× | | × |
| 2-228-1 | normal hamster | mouse CTGF | | ○○× | ○○△ | ○○△ | | ○ |

Fig. 2

| Clone name | Immunized Animal | Antigen | Isotype | Crossreactivity | | | Epitope Mapping | Activity of Inhibiting the Binding of NRK Cells | Activity of Inhibiting the Proliferation of NRK Cells |
|---|---|---|---|---|---|---|---|---|---|
| | | | | Human CTGF | Mouse CTGF | Rat CTGF | | | |
| A4.3 | human antibody-producing mouse | human CTGF | IgG2/κ | ○○△ | ○○△ | ○○× | A | × | ○ |
| A11.1 | human antibody-producing mouse | human CTGF | IgG2/κ | ○○○ | ○○△ | ○△× | (B) | | ○ |
| A15.1 | human antibody-producing mouse | human CTGF | IgG2/κ | ○○△ | ○×× | ××× | B | | ○ |
| A29.6 | human antibody-producing mouse | human CTGF | IgG2/κ | ○○○ | ○○○ | ○△× | B | × | ○ |
| B13.7 | human antibody-producing mouse | human CTGF | IgG2/κ | ○○△ | ○○× | ○×× | B | | ○ |
| B22.2 | human antibody-producing mouse | human CTGF | IgG2/κ | ○○△ | ○○△ | ○○△ | B | × | ○ |
| B29.6 | human antibody-producing mouse | human CTGF | IgG2/κ | ○○△ | ○○△ | ○○× | - | | ○ |
| B35.1 | human antibody-producing mouse | human CTGF | IgG2/κ | ○○△ | ○○× | ○×× | B/C | ○ | ○ |
| C26.11 | human antibody-producing mouse | human CTGF | IgG2/κ | ○○△ | ○○× | ○×× | B(C) | ○ | ○ |
| C59.1 | human antibody-producing mouse | human CTGF | IgG2/κ | ○○△ | ○○× | ○△× | (D) | ○ | ○ |
| C114.4 | human antibody-producing mouse | human CTGF | IgG2/κ | ○○× | ○○× | ○△× | D | | ○ |
| M32.2 | human antibody-producing mouse | human CTGF | IgG2/κ | ○○△ | ○△× | △×× | A-/B/C | | ○ |
| M33.3 | human antibody-producing mouse | human CTGF | IgG2/κ | ○○△ | ○○△ | ○○△ | A-/B | | ○ |
| M84.4 | human antibody-producing mouse | human CTGF | IgG2/κ | ○○△ | ○○△ | △×× | A-/B/C | × | ○ |
| M107.2 | human antibody-producing mouse | human CTGF | IgG2/κ | ○○△ | ○○△ | ○△× | B | | ○ |
| M122 | human antibody-producing mouse | human CTGF | IgG2/κ | | | | D | | ○ |
| M124.6 | human antibody-producing mouse | human CTGF | IgG2/κ | ○○△ | ○○△ | ○○△ | B | | ○ |
| M194.2 | human antibody-producing mouse | human CTGF | IgG2/κ | ○○△ | ○○△ | ○△× | A-/B | × | ○ |
| M244 | human antibody-producing mouse | human CTGF | IgG2/κ | | | | B | | ○ |
| M255 | human antibody-producing mouse | human CTGF | IgG2/κ | | | | D | | ○ |
| M268.1 | human antibody-producing mouse | human CTGF | IgG2/κ | ○○× | ○○△ | ○○× | B | | ○ |
| M288.5 | human antibody-producing mouse | human CTGF | IgG2/κ | ○×× | ○△× | ○×× | A-/B | | ○ |
| M291.2 | human antibody-producing mouse | human CTGF | IgG2/κ | ○○× | ○△× | ○×× | D | | ○ |
| M295.2 | human antibody-producing mouse | human CTGF | IgG2/κ | ○○○ | ○○○ | ○○△ | B | × | ○ |
| M315 | human antibody-producing mouse | human CTGF | IgG2/κ | | | | B/C | ○ | ○ |
| M320.2 | human antibody-producing mouse | human CTGF | IgG2/κ | | | | B | × | ○ |
| N45.2 | human antibody-producing mouse | human CTGF | IgG2/κ | ○○△ | ○○× | ○△× | A-/B | × | ○ |
| N50.1 | human antibody-producing mouse | human CTGF | IgG2/κ | ○○× | ○○× | ○△× | A-/B | | ○ |
| N60.1 | human antibody-producing mouse | human CTGF | IgG2/κ | ○○△ | ○○× | ○△× | B/C | × | ○ | p<0.01 vs Normal mice (abdomen-opened only)
**p<0.01 vs PBS-injected group (Student t-test)

MONOCLONAL ANTIBODY AGAINST CONNECTIVE TISSUE GROWTH FACTOR AND MEDICINAL USES THEREOF

CROSS-REFERENCES

This application is a U.S. National Phase application of PCT Application No. PCT/JP98/05697 filed Dec. 16, 1998, which is the international application of Japanese Application No. 9/367699 filed Dec. 25, 1997 and Japanese Application No. 10/356,183 filed Dec. 15, 1998, to which applications we claim priority.

TECHNICAL FIELD

The present invention relates to monoclonal antibodies reactive to mammalian connective tissue growth factor (CTGF) or a portion thereof; cells producing the monoclonal antibodies; antibody-immobilized insoluble carriers on which the monoclonal antibodies or a portion thereof are immobilized; labeled antibodies obtained by labeling the monoclonal antibodies with labeling agents; kits for detecting, separating, assaying or purifying mammalian CTGF; methods for detecting, separating, assaying or purifying mammalian CTGF; pharmaceutical compositions comprising the monoclonal antibodies; transgenic mice to which the human CTGF gene is introduced; a polypeptide of rat CTGF; a DNA encoding rat CTGF; and antibodies reactive to rat CTGF.

BACKGROUND ART

Injured tissues are regenerated by the following process: removal of useless tissue fragments and cell fragments or bacteria and so on by phagocytes such as macrophages that migrate to the injured site; recovery of vessels; and the subsequent tissue renewal. Transforming growth factor β(TGF-β) produced by macrophages and neutrophils, which appear during the process of the tissue regeneration and recovery, has been revealed to serve as the first regulatory factor in the regeneration-recovery process.

TGF-β has multiple functions. The factor is known to regulate the production of the extracellular matrix (ECM) from connective tissue cells as well as to induce the proliferation of mesenchymal cells and to inhibit the proliferation of vascular endothelial cells and epithelial cells.

Increased production of platelet-derived growth factor (PDGF) and connective tissue growth factor (CTGF; also called Hcs24) is found in the culture supernatant of the above-mentioned mesenchymal cells of which proliferation is induced by a stimulus with TGF-β. Because of this, it is presumed that the cell proliferation is not directly but indirectly induced by TGF-β with the help of other regulatory factors.

Human and mouse CTGFs have been identified previously (so far, there is no report on the identification of rat CTGF), and their physicochemical and biological properties have been analyzed (<human CTGF>: J. Cell Biology, vol. 114, No. 6, p.1285–1294, 1991; Int. J. Biochem. Cell Biol., Vol. 29, No. 1, p. 153–161, 1997; Circulation, vol. 95, No. 4, p.831–839, 1997; Cell Growth Differ., Vol. 7, No. 4, p. 469–480, 1996; J. Invest. Dermatol., Vol. 106, No. 4, p. 729–733, 1996; J. Invest. Dermatol., Vol. 105, No. 2, p. 280–284, 1995; J. Invest. Dermatol. Vol. 105, No. 1, p. 128–132, 1995; WO96/38172; <mouse CTGF (Fisp12)>: Unexamined Published Japanese Patent Application (JP-A) No. Hei 5-255397; Cell Growth Differ., vol. 2, No. 5, p. 225–233, 1991; FEBS Letters, Vol. 327, No. 2, p. 125–130, 1993; DNA Cell Biol., Vol. 10, No. 4, p. 293–308, 1991).

CTGF is a cysteine-rich secretory glycoprotein with a molecular weight of about 38 kDa. It has been revealed that the biosynthesis and secretion of the protein are induced by TGF-β. CTGF has similar properties with PDGF in the light of that: their productions are induced by TGF-β; they bind to the PDGF receptor and induce the proliferation of mesenchymal cells; and they are produced by fibroblasts and epithelial cells. However, they exhibit no homology at the amino acid level and thus the two molecules are distinct to each other (The Journal of Cell Biology, vol. 114, No. 6, p. 1287–1294, 1991; Molecular Biology of the Cell, Vol. 4, p.637–645, 1993).

In recent studies, low molecular weight species of CTGF have been found in the culture supernatant of human and mouse fibroblast cells as well as in the secreting fluid derived from the porcine uterus. They are biologically active but are presumed to be degradation products of 38 kDa CTGF molecules, since their molecular weights are about 10–12 kDa (Growth Factors, vol. 15, No. 3, p. 199–213, 1998; J. Biol. Chen., vol. 272, No. 32, p. 20275–20282, 1997).

Details of the relationship between physiological functions of CTGF and diseases have yet to be fully clarified. However, it has been found that: CTGF production is induced by TGF-β; the expression level of CTGF mRNA is significantly high in tissues and cells derived from patients affected with various diseases (Int. J. Biochem. Cell. Biol., Vol. 29, No. 1, p. 153–161, 1997; Circulation, Vol. 95, No. 4, p. 831–839, 1997; J. Invest. Dermatol, Vol. 106, No. 4, p. 729–733, 1996; J. Invest. Dermatol., Vol. 105, No. 2, p. 128–132, 1995; J. Cell Physiol., Vol. 165, No. 3, p. 556–565, 1995; Kidney Int., Vol. 48, No. 2, p. 5001–5009, 1995); and CTGF enhances the chemotaxis and proliferation of the vascular endothelial cells (J. Cell. Biol., Vol. 114, No. 6, p. 1285–1294, 1991; Exp. Cell Res., Vol. 233, p. 63–77, 1997; Journal of Japanese Association for Oral Biology, Vol. 38, extra number, p. 463, PD0187, 1996; the 69th meeting of the Japanese Biochemical Society, proceedings, p. 683, 1P0535, 1996). These findings suggest the possibility that CTGF is associated with the onset and/or advancement of a variety of diseases.

Identification of the specific diseases awaits further findings and advancement in research. Nonetheless, CTGF has been presumed to be involved in the onset and/or advancement of a wide variety of diseases including, for example, cancers, arteriosclerosis, and skin diseases (for example, psoriasis, scleroderma, atopy, and keloid), kidney diseases, arthritis (for example, rheumatoid arthritis), various fibrotic diseases (fibrotic diseases in tissues as observed in arteriosclerosis, cirrhosis, arthritis, scleroderma, keloid, kidney fibrosis and pulmonary fibrosis, etc.).

To elucidate the association of CTGF with such various diseases, it is generally effective to detect and assay CTGF and/or the protein fragments thereof in the body fluids (serum, etc.) from patients and mammals affected with the diseases; the values determined are compared with normal values (obtained from mammals including normal persons, normal mice, normal rats and normal rabbits, etc.).

The detection and assay of secretory proteins such as CTGF are carried out by immunological assays based on antigen-antibody interaction by using the antibody (preferably used are monoclonal antibodies) which is reactive to the secretory protein to be detected; specifically, immunoassays such as radioimmunoassay (RIA) and enzyme immunoassay (EIA, ELISA) are widely used as the most convenient and useful methods for the purpose.

In this context, for the purpose of assaying CTGF, it is necessary to develop detection and assay methods using such immunoassay systems and also to prepare monoclonal antibodies against CTGF required for the establishment of assay methods. There are some reports on the preparation of antiserum reactive to CTGF (Exp. Cell Res., Vol. 233, p. 63–77, 1997; Cell Growth Differ., Vol. 8, No. 1, p. 61–68, 1997; the 69th meeting of Japanese Biochemical Society, proceedings, p. 683, 1P0534, 1996) but no report on the preparation of functional anti-CTGF monoclonal antibody which has particularly high affinity for CTGF and/or the capability of neutralizing the CTGF activity; no immunoassay systems for CTGF have so far been provided at all.

Such monoclonal antibodies having the capability of neutralizing the CTGF activity described hereinabove are useful not only as components in an immunoassay system but also as pharmaceutical antibody preparations for the treatment and/or prevention of the above-mentioned diseases caused by CTGF secretion. However, there have not been any report on such monoclonal antibodies yet.

DISCLOSURE OF THE INVENTION

Thus, the development of monoclonal antibodies reactive to CTGFs from various mammals such as humans, mice, rats and rabbits, has been desirably awaited. Such monoclonal antibodies are useful for the understanding of biological functions of CTGF associated with the onset and/or advancement of the above-mentioned various diseases as well as for the understanding of cause-effect relations between CTGF and the various diseases. Such monoclonal antibodies are also usable as active ingredients of pharmaceutical products for treating and preventing the diseases caused by CTGF. In particular, development of monoclonal antibodies having sufficiently high affinities for CTGF, the capability of neutralizing the CTGF activity, and/or the sufficient crossreactivity to CTGFs from a variety of mammalian species, is demanded when the antibodies are used as components in immunoassay systems for detecting CTGF to elucidate the functions of CTGF as well as the relationship between CTGF and various diseases.

In addition, it is necessary to develop monoclonal antibodies with reduced antigenicity or without antigenicity as well as with the neutralizing activity described above, when the antibodies are used for the treatment and/or prevention of various diseases in patients.

In order to fulfill the social needs, the present inventors extensively studied the monoclonal antibodies against CTGFs from a variety of mammals, and using CTGFs from various mammals as immunogens, succeeded in preparing various monoclonal antibodies against CTGFs from a variety of mammals; the antibodies are different in properties such as antigenic specificity, affinity for the antigens, the neutralizing activity and the crossreactivity.

The present inventors also succeeded, for the first time in the world, in preparing various human monoclonal antibodies against human CTGF, by immunizing, with human CTGF as an immunogen, transgenic mice created to produce human antibodies by using recombinant technology. Furthermore, the present inventors found that intact CTGFs in body fluids (serum, etc.) from a variety of mammals (human, mouse, rat, and rabbit) could be highly sensitively assayed by using various immunoassay systems constructed with the various monoclonal antibodies described above. Thus the present inventions were achieved.

The present invention was also achieved by the findings that the latter, i.e., the human antibodies, has not only the capability of significantly neutralizing the human CTGF activity, but also therapeutic effects on, for example, fibrotic diseases in tissues (kidney fibrosis, etc.) as well. The fact that these human antibodies are non-antigenic in humans, dramatically elevates the utility value of antibody as a pharmaceutical, because antigenicity is a major therapeutic problem (side effect) in medical treatment with antibody pharmaceuticals comprising antibodies derived from non-human mammals such as mice.

In particular, the present invention provides, for the first time in the field to which the present invention pertains, monoclonal antibodies that are reactive to various mammalian CTGFs and possess various useful properties as pharmaceuticals to treat and prevent diseases in patients and as components in immunoassay systems to detect and assay CTGF in body fluids from various mammals such as humans, mice, and rats.

In addition to this, the present invention provides methods and kits of immunoassay for CTGF using such various monoclonal antibodies against CTGF for the first time.

The inventive anti-human CTGF monoclonal antibodies are extremely useful as pharmaceuticals for the treatment and prevention of various diseases caused by CTGF because the antibodies are nonantigetic in humans.

By using an immunoassay with the monoclonal antibodies of the present invention, it is possible to conveniently and highly sensitively detect and assay intact CTGF in the body fluids from healthy and diseased mammals (humans, mice, rats and rabbits).

Specifically, the present inventions are defined as follows:
(1) a monoclonal antibody or a portion thereof, comprising a property in any of (a) to (g) below:
 (a) reactive to human, mouse and rat connective tissue growth factors (CTGFs);
 (b) reactive to both human and mouse CTGFs but not reactive to rat CTGF;
 (c) reactive to both mouse and rat CTGFs but not reactive to human CTGF;
 (d) inhibiting binding of human CTGF to human kidney-derived fibroblast cell line 293-T (ATCC CRL1573), or the binding of mouse CTGF to said cell line 293-T;
 (e) inhibiting binding of human CTGF to any cells of rat kidney-derived fibroblast cell line NRK-49F (ATCC CRL-1570), human osteosarcoma-derived cell line MG-63 (ATCC CRL-1427), or human lung-derived fibroblasts;
 (f) inhibiting cell proliferation of rat kidney-derived fibroblast cell line NRK-49F (ATCC CRL-1570) induced by a stimulus with human or mouse CTGF; or,
 (g) inhibiting an increase of hydroxyproline in the kidney, wherein said hydroxyproline level tends to be elevated;
(2) the monoclonal antibody or a portion thereof according to (1), comprising a property in any of (a) to (c) below:
 (a) obtainable by immunizing a mouse with human CTGF or a portion thereof, and reactive to human, mouse and rat CTGFS;
 (b) obtainable by immunizing a hamster with mouse CTGF or a portion thereof, and reactive to human, mouse and rat CTGFS; or,
 (c) obtainable by immunizing a rat with mouse CTGF or a portion thereof, and reactive to human, mouse and rat CTGFS;

(3) the monoclonal antibody or a portion thereof according to (1), comprising a property in any of (a) to (c) below:
  (a) obtainable by immunizing a mouse with human CTGF or a portion thereof, reactive to human, mouse and rat CTGFs and inhibiting binding of human CTGF to human kidney-derived fibroblast cell line 293-T (ATCC CRL1573);
  (b) obtainable by immunizing a rat with mouse CTGF or a portion thereof, reactive to human, mouse and rat CTGFs and inhibiting binding of mouse CTGF to human kidney-derived fibroblast cell line 293-T (ATCC CRL1573); or,
  (c) obtainable by immunizing a hamster with mouse CTGF or a portion thereof, and reactive to human, mouse and rat CTGFs and inhibiting binding of mouse CTGF to human kidney-derived fibroblast cell line 293-T (ATCC CRL1573);
(4) the monoclonal antibody or a portion thereof according to (1), wherein said monoclonal antibody is produced by a hybridoma identified by an international deposit accession No. FERM BP-6208;
(5) the monoclonal antibody or a portion thereof according to (1), wherein said monoclonal antibody comprises a property substantially equivalent to that of a monoclonal antibody produced by a hybridoma identified by an international deposit accession No. FERM BP-6208;
(6) the monoclonal antibody or a portion thereof according to (1), wherein said monoclonal antibody is produced by a hybridoma identified by an international deposit accession No. FERM BP-6209;
(7) the monoclonal antibody or a portion thereof according to (1), wherein said monoclonal antibody comprises a property substantially equivalent to that of a monoclonal antibody produced by a hybridoma identified by an international deposit accession No. FERM BP-6209;
(8) a human monoclonal antibody or a portion thereof, reactive to any human, mouse or rat CTGF;
(9) the human monoclonal antibody or a portion thereof according to (8), wherein said human monoclonal antibody is reactive to human CTGF;
(10) a human monoclonal antibody or a portion thereof, reactive to human CTGF and comprises a property in any of (a) to (d) below:
  (a) inhibiting binding of human CTGF to human kidney-derived fibroblast cell line 293-T (ATCC CRL1573);
  (b) inhibiting binding of human CTGF to any of rat kidney-derived fibroblast cell line NRK-49F (ATCC CRL-1570), human osteosarcoma-derived cell line MG-63 (ATCC CRL-1427), or human lung-derived fibroblasts;
  (c) inhibiting the cell proliferation of rat kidney-derived fibroblast cell line NRK-49F (ATCC CRL-1570) induced by a stimulus with human or mouse CTGF; or,
  (d) inhibiting an increase of hydroxyproline in kidney, wherein said hydroxyproline level tends to be elevated;
(11) the human monoclonal antibody or a portion thereof according to any one of (8) to (10), wherein said human monoclonal antibody is derived from a non-human transgenic mammal which is capable of producing a human antibody;
(12) the human monoclonal antibody or a portion thereof according to (11), wherein said human monoclonal antibody is obtainable by immunizing a non-human transgenic mammal which is capable of producing a human antibody, with human CTGF;
(13) the human monoclonal antibody or a portion thereof according to any one of (8) to (12), wherein said non-human transgenic mammal is a transgenic mouse;
(14) the human monoclonal antibody or a portion thereof according to any one of (8) to (13), wherein a V-region DNA encoding a heavy chain variable region of said human monoclonal antibody is derived from a gene segment selected from the group consisting of DP-5, DP-38, DP-65 and DP-75;
(15) the human monoclonal antibody or a portion thereof according to any one of (8) to (13), wherein a V-region DNA encoding a light chain variable region of said human monoclonal antibody is derived from a gene segment selected from the group consisting of DPK1, DPK9, DPK12 and DPK24;
(16) the human monoclonal antibody or a portion thereof according to any one of (8) to (15), wherein a V-region DNA encoding a heavy chain variable region of said human monoclonal antibody is derived from a gene segment selected from the group consisting of DP-5, DP-38, DP-65 and DP-75, and wherein a V-region DNA encoding a light chain variable region of said human monoclonal antibody is derived from a gene segment selected from the group consisting of DPK1, DPK9, DPK12 and DPK24;
(17) the human monoclonal antibody or a portion thereof according to (9), wherein an amino acid sequence of a heavy chain variable region of said human monoclonal antibody comprises an amino acid sequence defined below in any of (a) to (j) below:
  (a) the amino acid positions 21 to 120 of the amino acid sequence of SEQ ID NO: 6;
  (b) the amino acid positions 21 to 120 of the amino acid sequence of SEQ ID NO: 6, wherein one or more amino acids are deleted, substituted, inserted or added;
  (c) the amino acid positions 21 to 118 of the amino acid sequence of SEQ ID NO: 8;
  (d) the amino acid positions 21 to 118 of the amino acid sequence of SEQ ID NO: 8, wherein one or more amino acids are deleted, substituted, inserted or added;
  (e) the amino acid positions 21 to 116 of the amino acid sequence of SEQ ID NO: 10;
  (f) the amino acid positions 21 to 116 of the amino acid sequence of SEQ ID NO: 10, wherein one or more amino acids are deleted, substituted, inserted or added;
  (g) the amino acid positions 21 to 116 of the amino acid sequence of SEQ ID NO: 12;
  (h) the amino acid positions 21 to 116 of the amino acid sequence of SEQ ID NO: 12, wherein one or more amino acids are deleted, substituted, inserted or added;
  (i) the amino acid positions 21 to 117 of the amino acid sequence of SEQ ID NO: 14; or,
  (j) the amino acid positions 21 to 117 of the amino acid sequence of SEQ ID NO: 14, wherein one or more amino acids are deleted, substituted, inserted or added;
(18) the human monoclonal antibody or a portion thereof according to (9), wherein an amino acid sequence of a light chain variable region of said human monoclonal antibody comprises an amino acid sequence in any of (a) to (j) below:
(a) the amino acid positions 21 to 120 of the amino acid sequence of SEQ ID NO: 16;
(b) the amino acid positions 21 to 120 of the amino acid sequence of SEQ ID NO: 16, wherein one or more amino acids are deleted, substituted, inserted or added;
(c) the amino acid positions 21 to 121 of the amino acid sequence of SEQ ID NO: 18;
(d) the amino acid positions 21 to 121 of the amino acid sequence of SEQ ID NO: 18, wherein one or more amino acids are deleted, substituted, inserted or added;
(e) the amino acid positions 23 to 117 of the amino acid sequence of SEQ ID NO: 20;
(f) the amino acid positions 23 to 117 of the amino acid sequence of SEQ ID NO: 20, wherein one or more amino acids are deleted, substituted, inserted or added;
(g) the amino acid positions 17 to 111 of the amino acid sequence of SEQ ID NO: 22;
(h) the amino acid positions 17 to 111 of the amino acid sequence of SEQ ID NO: 22, wherein one or more amino acids are deleted, substituted, inserted or added;
(i) the amino acid positions 23 to 118 of the amino acid sequence of SEQ ID NO: 24; or,
(j) the amino acid positions 23 to 118 of the amino acid sequence of SEQ ID NO: 24, wherein one or more amino acids are deleted, substituted, inserted or added;
(19) a monoclonal antibody or a portion thereof, reactive to human CTGF, which is produced by a hybridoma identified by an international deposit accession No. FERM BP-6535;
(20) a monoclonal antibody or a portion thereof, reactive to human CTGF and comprises a property substantially equivalent to that of a monoclonal antibody produced by a hybridoma identified by an international deposit accession No. FERM BP-6535;
(21) a monoclonal antibody or a portion thereof, reactive to human CTGF, and which is produced by a hybridoma identified by an international deposit accession No. FERM BP-6598;
(22) a monoclonal antibody or a portion thereof, reactive to human CTGF and comprises a property substantially equivalent to that of a monoclonal antibody produced by a hybridoma identified by an international deposit accession No. FERM BP-6598;
(23) a monoclonal antibody or a portion thereof, reactive to human CTGF, which is produced by a hybridoma identified by an international deposit accession No. FERM BP-6599;
(24) a monoclonal antibody or a portion thereof, reactive to human CTGF and comprises a property substantially equivalent to that of a monoclonal antibody produced by a hybridoma identified by an international deposit accession No. FERM BP-6599;
(25) a monoclonal antibody or a portion thereof, reactive to human CTGF, which is produced by a hybridoma identified by an international deposit accession No. FERM BP-6600;
(26) a monoclonal antibody or a portion thereof, reactive to human CTGF and comprises a property substantially equivalent to that of a monoclonal antibody produced by a hybridoma identified by an international deposit accession No. FERM BP-6600;
(27) a monoclonal antibody or a portion thereof, reactive to human CTGF, and which is non-reactive to a antigen-antibody complex of human CTGF and the monoclonal antibody reactive to human CTGF of (17) or (18);
(28) the monoclonal antibody or a portion thereof according to (27), wherein said monoclonal antibody is a human monoclonal antibody;
(29) a monoclonal antibody or a portion thereof, reactive to rat CTGF;
(30) a recombinant chimeric monoclonal antibody, reactive to human CTGF, and of which a variable region is derived from a variable region of the monoclonal antibody according to any one of (2) to (7), (27) or (29) and of which a constant region is derived from a constant region of a human immunoglobulin;
(31) a recombinant humanized monoclonal antibody, reactive to human CTGF, of which a whole or portion of the complementarity-determining regions of a hyper-variable region is derived from complementarity-determining regions of the monoclonal antibody of any one of (2) to (7), (27) or (29), of which framework regions of a hyper-variable region are derived from the framework regions of a human immunoglobulin and of which a constant region is derived from a constant region of a human immunoglobulin;
(32) a cell producing the monoclonal antibody according to any one of (1) to (29);
(33) a cell producing the recombinant monoclonal antibody according to (30) or (31);
(34) the cell according to (32), wherein said cell is a hybridoma obtainable by fusing a mammalian myeloma cell with a mammalian B cell which is capable of producing the monoclonal antibody;
(35) the cell according to (32) or (33), wherein said cell is a genetically engineered cell transformed by either one or both of the DNAs encoding a heavy chain and light chain of the monoclonal antibody;
(36) the hybridoma according to (34), wherein said hybridoma is identified by an international deposit accession No. FERM BP-6535;
(37) the hybridoma according to (34), wherein said hybridoma is identified by an international deposit accession No. FERM BP-6598;
(38) the hybridoma according to (34), wherein said hybridoma is identified by an international deposit accession No. FERM BP-6599;
(39) the hybridoma according to (34), wherein said hybridoma is identified by an international deposit accession No. FERM BP-6600;
(40) the hybridoma according to (34), wherein said hybridoma is identified by an international deposit accession No. FERM BP-6208;
(41) the hybridoma according to (34), wherein said hybridoma is identified by an international deposit accession No. FERM BP-6209;
(42) an antibody-immobilized insoluble carrier on which the monoclonal antibody according to anyone of (1) to (31) is immobilized;
(43) the antibody-immobilized insoluble carrier according to (42), wherein said insoluble carrier is selected from the group consisting of plates, test tubes, tubes, beads, balls, filters and membranes;

(44) the antibody-immobilized insoluble carrier according to (42), wherein said insoluble carrier is a filter or membrane, or that used for affinity column chromatography;

(45) a labeled antibody which is prepared by labeling the monoclonal antibody of any one of (1) to (31) with a labeling agent capable of providing a detectable signal by itself or together with other substances;

(46) the labeled antibody according to (45), wherein said labeling agent is an enzyme, fluorescent substance, chemiluminescent substance, biotin, avidin, or radioisotope;

(47) a kit for detecting or assaying mammalian CTGF, comprising at least one monoclonal antibody, an antibody-immobilized insoluble carrier, and a labeled antibody, which is selected from the group consisting of the monoclonal antibody according to any one of (1) to (31), the antibody-immobilized insoluble carrier according to (42) or (43), and the labeled antibody according to (45) or (46);

(48) the kit for detecting or assaying mammalian CTGF according to (47), comprising the antibody-immobilized insoluble carrier according to (42) or (43) and the labeled antibody according to (45) or (46);

(49) a method for detecting or assaying mammalian CTGF by an immunoassay using at least one monoclonal antibody, an antibody-immobilized insoluble carrier, and a labeled antibody, which is selected from the group consisting of the monoclonal antibody according to any one of (1) to (31), the antibody-immobilized insoluble carrier according to (42) or (43), and the labeled antibody according to (45) or (46);

(50) the method for detecting or assaying mammalian CTGF by an immunoassay according to (49), comprising at least the following steps of (a) and (b):
(a) reacting a sample with the antibody-immobilized insoluble carrier according to (42) or (43); and,
(b) reacting the labeled antibody according to (45) or (46) with an antigen-antibody complex formed by binding mammalian CTGF in said sample to the antibody-immobilized insoluble carrier;

(51) the method for detecting or assaying mammalian CTGF by an immunoassay according to (49), comprising at least the following steps of (a) and (b):
(a) reacting a sample with the labeled antibody according to (45) or (46); and,
(b) reacting the antibody-immobilized insoluble carrier according to (42) or (43) with the antigen-antibody complex formed by binding said labeled antibody and mammalian CTGF in said sample;

(52) the method for detecting or assaying mammalian CTGF by an immunoassay according to (49), comprising at least the following step of (a):
(a) reacting a mixture comprising the antibody-immobilized insoluble carrier according to (42) or (43), the labeled antibody according to (45) or (46), and a sample;

(53) the method for detecting or assaying mammalian CTGF by an immunoassay according to (49), comprising at least the following step of (a):
(a) reacting a sample and a mammalian CTGF standard labeled with a labeling agent capable of providing a detectable signal by itself or together with other substances, with the antibody-immobilized insoluble carrier according to (42) or (43);

(54) the method for detecting or assaying mammalian CTGFs by an immunoassay according to (49), comprising at least the following steps of (a) and (b):
(a) reacting the monoclonal antibody according to any one of (1) to (31) with a mixture comprising a sample and a mammalian CTGF standard labeled with a labeling agent capable of providing a detectable signal by itself or together with other substances; and,
(b) reacting a mammalian antiserum reactive to said monoclonal antibody with the antigen-antibody complex formed by binding mammalian CTGF in said sample or said labeled mammalian CTGF standard and said monoclonal antibody;

(55) the method for detecting or assaying mammalian CTGFs by an immunoassay according to (49), comprising at least the following steps of any of (a) to (c):
(a) reacting the monoclonal antibody according to any of one s (1) to (31) with a sample;
(b) reacting a mammalian CTGF standard labeled with a labeling agent capable of providing a detectable signal by itself or together with other substances with a reaction product resulted from the reaction in step (a); and,
(c) reacting a mammalian antiserum reactive to said monoclonal antibody with the antigen-antibody complex formed by binding mammalian CTGF in said sample or said labeled mammalian CTGF standard, and said monoclonal antibody;

(56) a kit for separating or purifying mammalian CTGF, comprising the antibody-immobilized insoluble carrier according to (42) or (44);

(57) a method for separating or purifying mammalian CTGF, comprising using affinity chromatography with the antibody-immobilized insoluble carrier according to (42) or (44);

(58) the purification method for mammalian CTGF according to (57), wherein said affinity chromatography is affinity column chromatography;

(59) a transgenic mouse in which DNA encoding human CTGF is integrated into an endogenous gene locus;

(60) a rat CTGF comprising an amino acid sequence of, or substantially equivalent to the amino acid sequence of SEQ ID NO: 2;

(61) a DNA encoding a rat CTGF comprising the amino acid sequence of SEQ ID NO: 2;

(62) the DNA according to (61), comprising nucleotide sequence in the positions of 213 to 1256 of SEQ ID NO: 1;

(63) a pharmaceutical composition comprising the monoclonal antibody or a portion thereof according to any one of (2) to (31) and a pharmaceutically acceptable carrier;

(64) a pharmaceutical composition comprising the human monoclonal antibody or a portion thereof according to any one of (9) to (18) or (28) and a pharmaceutically acceptable carrier;

(65) a pharmaceutical composition comprising the human monoclonal antibody or a portion thereof according to any one of (14) to (18) and (28);

(66) the pharmaceutical composition according to any one of (63) to (65), for inhibiting proliferation of cells capable of proliferating by a stimulus with CTGF;

(67) the pharmaceutical composition according to any one of (63) to (65), for treating or preventing a disease accompanied by proliferation of cells capable of proliferating by a stimulus with CTGF;

(68) the pharmaceutical composition according to (66) or (67), wherein said proliferation is cell proliferation in a tissue selected from the group consisting of brain, neck, lung, heart, liver, pancreas, kidney, stomach, large intestine, small intestine, duodenum, bone marrow, uterus, ovary, testis, prostate gland, skin, mouth, tongue and blood vessels;

(69) the pharmaceutical composition according to (68), wherein said tissue is the lung, liver, kidney or skin;

(70) the pharmaceutical composition according to (69), wherein said tissue is the kidney;

(71) the pharmaceutical composition according to (67), wherein said disease is further accompanied by tissue fibrosis;

(72) the pharmaceutical composition according to (71), wherein said tissue fibrosis is tissue fibrosis in lung, liver, kidney or skin;

(73) the pharmaceutical composition according to (72), wherein said tissue fibrosis is kidney fibrosis;

(74) a pharmaceutical composition for treating or preventing a kidney disease, comprising a CTGF inhibitor or an agent for inhibiting CTGF production, and a pharmaceutically acceptable carrier;

(75) the pharmaceutical composition according to (74), wherein said inhibitor is a monoclonal antibody reactive to CTGF;

(76) the pharmaceutical composition according to (74), wherein said inhibitor is the monoclonal antibody of any one of (9) to (31);

(77) the pharmaceutical composition according to (76), wherein said inhibitor is the human monoclonal antibody according to any one of (14) to (18) and (28);

(78) the pharmaceutical composition according to any one of (74) to (77), wherein said disease is accompanied by tissue fibrosis;

(79) a pharmaceutical composition for inhibiting proliferation of cells in kidney which are capable of proliferating by a stimulus with CTGF, comprising a substance having an activity of inhibiting proliferation of said cells and a pharmaceutically acceptable carrier;

(80) the pharmaceutical composition according to (79), wherein said substance is a monoclonal antibody reactive to CTGF;

(81) the pharmaceutical composition according to (79), wherein said inhibitor is the monoclonal antibody according to any one of (9) to (31);

(82) the pharmaceutical composition according to (81), wherein said inhibitor is the human monoclonal antibody according to any one of (14) to (18) and (28).

The present inventions are described in detail herein below by defining terminologies used herein.

Herein, "mammals" mean humans, bovine, goats, rabbits, mice, rats, hamsters and guinea pigs; preferred are humans, rabbits, rats, hamsters or mice, and particularly preferred are humans, rats, hamsters or mice.

The terminologies "mammals except human" and "non-human mammals" in the present invention have the same meaning, and both indicate all the above-defined mammals except humans.

"Amino acids" used in the present invention mean any amino acid existing in nature and preferably the following amino acids presented by alphabetical triplets or single letter codes used to represent amino acids. (Gly/G) glycine, (Ala/A) alanine, (Val/V) valine, (Leu/L) leucine, (Ile/I) isoleucine, (Ser/S) serine, (Thr/T) threonine, (Asp/D) aspartic acid, (Glu/E) glutamic acid, (Asn/N) asparagine, (Gln/Q) glutamine, (Lys/K) lysine, (Arg/R) arginine, (Cys/C) cysteine, (Met/M) methionine, (Phe/F) phenylalanine, (Tyr/Y) tyrosine, (Trp/W) tryptophane, (His/H) histidine, (Pro/P) proline.

The term "connective tissue growth factor (CTGF)" as referred to in the present invention means CTGF derived from the above-mentioned mammals, and includes, for example, human and mouse CTGFs having the above-described structure and function as reported in previous reports (for example: The Journal of Cell Biology Vol. 114, No. 6, p. 1287–1294, 1991; Molecular Biology of the Cell, Vol. 4, p. 637–645, 1993; Biochem. Biophys. Res. Comm. Vol.234, p.206–210, 1997, etc.). As a matter of course, the "connective tissue growth factor" also includes rat CTGF that is included within the scope of the present invention.

Moreover, "connective tissue growth factor" as referred to in the present invention includes not only the CTGF (for example, human CTGF) with a molecular weight of about 38 kDa as documented in reports but also a low-molecular-weight CTGF protein, with a molecular weight ranging from about 10 to about 12 kDa. The low-molecular-weight protein is assumed to be a degradation product of the full-length CTGF (for example, human CTGF) with a molecular weight of about 38 kDa (Growth Factors, Vol. 15, No. 3, p. 199–213, 1998; J. Biol. Chem., Vol. 272, No. 32, p. 20275–20282, 1997). Although the structure of this low-molecular-weight CTGF remains to be clarified, there is a possibility that, in the case of human CTGF, the low-molecular-weight CTGF corresponds to a C-terminal protein (molecular weight: about 11,800 Da) consisting of 103 amino acid residues resulted from the cleavage of the full-length human CTGF consisting of 349 amino acids between leucine at amino acid position 246 (Leu246) and glutamic acid at amino acid position 247 (Glu247) or another C-terminal protein (molecular weight: about 11,671 Da) consisting of 102 amino acid residues resulted from the cleavage of the full-length human CTGF between glutamic acid at amino acid position 247 (Glu247) and glutamic acid at amino acid position 248 (Glu248).

In addition, CTGF as referred to in the present invention includes CTGFs having substantially the same amino acid sequence as that of the natural CTGF (in particular, human CTGF) having the native primary structure (amino acid sequence) or a portion thereof, as long as the "monoclonal antibody" of the present invention, which is described hereinafter, is reactive to the natural CTGF or a portion thereof.

Here, "having substantially the same amino acid sequence" means to include a protein having an amino acid sequence where multiple amino acids, preferably 1 to 10 amino acids, particularly preferably 1 to 5 amino acids, in the amino acid sequence of the natural CTGF protein, are substituted, deleted and/or modified, and a protein having an amino acid sequence where multiple amino acids, preferably 1 to 10 amino acids, particularly preferably 1 to 5 amino acids, are added to the amino acid sequence, as long as the protein has substantially the same biological properties as the natural CTGF protein. Furthermore, a combination of two or more of the above alterations including a substitution, deletion, modification and addition is also included.

The CTGF of the present invention can be produced by suitably using a method known in the technical field, such as recombinant technology, chemical synthesis or cell culture, or by using a modified method thereof.

The CTGF of the present invention also includes "a portion" of the CTGF. The terminology "a portion of CTGF" here refers to a polypeptide comprising any arbitrary partial amino acid sequence derived from the above-defined CTGF (including the above-mentioned low-molecular-weight CTGF of about 10 to 12 kDa). Specifically, the polypeptide includes CTGF peptide fragments with 5 to 100 amino acid residues (for example, the peptides in the C-terminus), more specifically, includes CTGF peptide fragments with 5 to 50 amino acid residues, and even more specifically the peptide fragments with 5 to 30 amino acid residues. Preferably, the polypeptide has a partial structure of CTGF comprising a domain that binds or interacts with the receptor thereof (receptor binding site, etc.) or comprising a domain necessary to the biological function of CTGF (active site, etc.).

These polypeptides (partial structures or fragments) can be produced according to a method known in the technical field, or a modified method thereof, by using recombinant technology or chemical synthesis. The polypeptides can also be produced by appropriately digesting the CTGF isolated by the cell culture method with proteases and such.

"Monoclonal antibody" as referred to in the present invention is a monoclonal antibody reactive to mammalian connective tissue growth factor (CTGF) or a portion thereof. Specifically, the "monoclonal antibody" is a monoclonal antibody having a property described above in any of the inventions (1) to (31). More specifically, "monoclonal antibody" means the various monoclonal antibodies with a variety of properties and industrial utilities described below in the examples and as indicated in the drawings.

As a preferable embodiment, the monoclonal antibody of the present invention is exemplified by the following monoclonal antibodies described in (i) to (iv):

(i) the monoclonal antibody according to (1), wherein the monoclonal antibody comprises a property described in any of (d) to (g);

(ii) the monoclonal antibody according to (2);

(iii) the monoclonal antibody according to any one of (4) to (7);

(iv) the monoclonal antibody according to any one of (9) to (31).

In this embodiment, for the purpose of usage as a pharmaceutical for treating or preventing various diseases, preferable monoclonal antibody is a human monoclonal antibody included by the antibodies described above in (i) to (iv).

In this embodiment, any of the monoclonal antibodies described above in (i) to (iv) are usable for the detection, assay, separation or purification of mammalian CTGFs, which is another subject matter of the present invention.

As a more preferable embodiment, the monoclonal antibody of the present invention is exemplified by the following monoclonal antibodies described in (v) and (vi):

(v) the monoclonal antibody according to (1), wherein the monoclonal antibody comprises a property described in any of (d) to (g);

(vi) the monoclonal antibody according to any of (4) to (7), (10), and (14) to (28).

In this embodiment, for the purpose of usage as a pharmaceutical for treating or preventing various diseases, preferable monoclonal antibody is a human monoclonal antibody included in the antibodies described above in (v) and (vi).

Furthermore, in this embodiment, any of the monoclonal antibodies described above in (v) and (vi) are usable for the detection, assay, separation or purification of mammalian CTGFs which is another subject matter of the present invention.

As a particularly preferable embodiment, the monoclonal antibody of the present invention is exemplified by the following monoclonal antibodies described in (vii) and (viii):

(vii) the monoclonal antibodies described above in any of (iv) to (vii);

(viii) the monoclonal antibody according to any of (14) to (26) and (28).

In this embodiment, for the purpose of usage as a pharmaceutical for treating or preventing various diseases, preferable monoclonal antibody is the human monoclonal antibody described above in (viii).

In this embodiment, any of the monoclonal antibodies described above in (vii) and (viii)are usable for the detection, assay, separation or purification of mammalian CTGFs which is another subject matter of this invention.

As a more particularly preferable embodiment, the monoclonal antibody of the present invention is exemplified by the following monoclonal antibodies described in (ix) to (xiv):

(ix) the monoclonal antibody according to (4) or(6);

(x) the monoclonal antibody according to any of (14) to (16);

(xi) the monoclonal antibody according to (17), wherein the monoclonal antibody comprises a property described in any of (a), (c), (e), (g) and (i);

(xii) the monoclonal antibody according to (18), wherein the monoclonal antibody comprises a property described in any of (a), (c), (e), (g) and (i);

(xiii) the monoclonal antibody according to any of (19), (21) (23) and (25);

(xiv) the monoclonal antibody according to (28).

In this embodiment, for the purpose of usage as a pharmaceutical for treating or preventing various diseases, preferable monoclonal antibody is the monoclonal antibody described above in any of (x) to (xiv).

In this embodiment, any of the monoclonal antibodies described above in (ix) to (xiv) are usable for the detection, assay, separation or purification of mammalian CTGFs, which is another subject matter of the present invention. However, the monoclonal antibody described above in (ix) is particularly preferable for the purpose.

The "monoclonal antibody" of the present invention also includes a natural monoclonal antibody prepared by immunizing mammals such as mice, rats, hamsters, guinea pigs or rabbits with the above-defined connective tissue growth factor (including natural, recombinant, and chemically synthesized protein and cell culture supernatant) or a portion thereof as an antigen (immunogen); a chimeric antibody and a humanized antibody (CDR-grafted antibody) produced by recombinant technology; and a human monoclonal antibody, for example, obtained by using human antibody-producing transgenic animals.

The "monoclonal antibody" of the present invention further includes a recombinant monoclonal antibody produced by the "cells producing recombinant monoclonal antibody" described hereinafter.

The monoclonal antibody includes those having any one of the isotypes of IgG, IgM, IgA (IgA1 and IgA2), IgD, or IgE. IgG (IgG1, IgG2, IgG3, and IgG4, preferably IgG2 or IgG4) or IgM is preferable. IgG is most preferred.

The polyclonal antibody (antisera) or monoclonal antibody of the present invention can be produced by known methods. Namely, mammals (including transgenic animals generated so as to produce an antibody derived from another animal species, such as the human antibody producing transgenic mice described below), preferably, mice, rats, hamsters, guinea pigs, rabbits, cats, dogs, pigs, goats, horses, or bovine, or more preferably, mice, rats, hamsters, guinea pigs, or rabbits are immunized, for example, with an antigen mentioned above with Freund's adjuvant, if necessary. The polyclonal antibody can be obtained from the serum obtained from the animal so immunized. The monoclonal antibodies are produced as follows. Hybridomas are produced by fusing the antibody-producing cells obtained from the animal so immunized and myeloma cells incapable of producing autoantibodies. Then the hybridomas are cloned, and clones producing the monoclonal antibodies showing the specific affinity to the antigen used for immunizing the mammal are screened.

The antibodies can also be produced using "recombinant monoclonal antibody producing cells" of the present invention described below.

Specifically, the monoclonal antibody can be produced as follows. Immunizations are done by injecting or implanting once or several times the CTGF (including natural, recombinant, and synthetic proteins, and cell culture supernatant) or its fragment as mentioned above as an immunogen, if necessary, with Freund's adjuvant, subcutaneously, intramuscularly, intravenously, through the footpad, or intraperitoneally into non-human mammals, such as mice, rats, hamsters, guinea pigs, or rabbits, preferably mice, rats or hamsters (including transgenic animals generated so as to produce antibodies derived from another animal such as the transgenic mouse producing human antibody described below). Usually, immunizations are performed once to four times every one to fourteen days after the first immunization. Antibody-producing cells are obtained from the mammal so immunized in about one to five days after the last immunization. The times and interval of the immunizations can be adequately altered according to the properties of the immunogen used.

Hybridomas that secrete a monoclonal antibody can be prepared by the method of Köhler and Milstein (Nature, Vol.256, pp.495–497(1975)) and by its modified method. Namely, hybridomas are prepared by fusing antibody-producing cells contained in a spleen, lymph node, bone marrow, or tonsil obtained from the non-human mammal immunized as mentioned above, preferably a spleen, with myelomas without autoantibody-producing ability, which are derived from, preferably, a mammal such as mice, rats, guinea pigs, hamsters, rabbits, or humans, or more preferably, mice, rats, or humans.

For example, mouse-derived myeloma P3/X63-AG8.653 (653, ATCC No. CRL1580), P3/NSI/1-Ag4-1 (NS-1), P3/X63-Ag8.U1 (P3U1), SP2/0-Ag14 (Sp2/0, Sp2), PAI, F0, or BW5147; rat-derived myeloma 210RCY3-Ag.2.3.; or human-derived myeloma U-266AR1, GM1500-6TG-A1-2, UC729-6, CEM-AGR, D1R11, or CEM-T15 can be used as a myeloma used for the cell fusion.

Monoclonal antibody producing cells (e.g., hybridoma) can be screened by cultivating the cells, for example, in microtiter plates and by measuring the reactivity of the culture supernatant in the well in which hybridoma growth is observed, to the immunogen used for the immunization mentioned above, for example, by an enzyme immunoassay such as RIA and ELISA.

The monoclonal antibodies can be produced from hybridomas by cultivating the hybridomas in vitro or in vivo such as in the ascites of mice, rats, guinea pigs, hamsters, or rabbits, preferably mice or rats, more preferably mice and isolating the antibodies from the resulting culture supernatant or ascites fluid of a mammal.

Furthermore, monoclonal antibodies can be obtained in a large quantity by cloning a gene encoding a monoclonal antibody from a hybridoma or "recombinant monoclonal antibody producing cells" of the present invention described below, generating transgenic animals such as bovine, goats, sheep, or pigs in which the gene encoding the monoclonal antibody is integrated in its endogenous gene using transgenic animal generating technique, and recovering the monoclonal antibody derived from the antibody gene from milk of the transgenic animals (Nikkei Science, No.4, pp.78–84 (1997)).

Cultivating the cells in vitro can be performed depending on the property of cells to be cultured, on the object of a test study, and on various culture, by using known nutrient media or any nutrient media derived from known basal media for growing, maintaining, and storing the hybridomas to produce monoclonal antibodies in the culture supernatant.

Examples of basal media are low calcium concentration media such as Ham'F12 medium, MCDB153 medium, or low calcium concentration MEM medium, and high calcium concentration media such as MCDB104 medium, MEM medium, D-MEM medium, RPMI1640 medium, ASF104 medium, or RD medium. The basal media can contain, for example, sera, hormones, cytokines, and/or various inorganic or organic substances depending on the objective.

Monoclonal antibodies can be isolated and purified from the culture supernatant or ascites mentioned above by saturated ammonium sulfate precipitation, euglobulin precipitation method, caproic acid method, caprylic acid method, ion exchange chromatography (DEAE or DE52), affinity chromatography using anti-immunoglobulin column or protein A column.

The monoclonal antibody of the present invention also includes a monoclonal antibody comprising the heavy chain and/or the light chain in which either or both of the chains have deletions, substitutions or additions of one or several amino acids in the sequences thereof; "several amino acids" as referred to here means multiple amino acid residues, specifically means one to ten amino acid residues, preferably one to five amino acid residues.

The partial modification of amino acid sequence (deletion, substitution, insertion, and addition) described above, can be introduced into the monoclonal antibody of the present invention by partially modifying the nucleotide sequence encoding the amino acid sequence. The partial modification of the nucleotide sequence can be performed by the usual method of site-specific mutagenesis (Proc. Natl. Acad. Sci. USA, Vol. 81, p. 5662–5666, 1984).

"Human monoclonal antibody" as referred to in this invention is a human monoclonal antibody reactive to the above-defined mammalian CTGFs (preferably human CTGF). The human monoclonal antibody is exemplified by the various human monoclonal antibodies with a variety of properties described below in the examples and as indicated in the drawings.

Specifically, the monoclonal antibody is a human immunoglobulin which is encoded by the human immunoglobulin gene segments in the entire region thereof including the variable region of the heavy chain (H chain), the constant region of the H chain, the variable region of the light chain (L chain) and the constant region of the L chain. The L chain is exemplified by a human κ chain and a human λ chain.

The human monoclonal antibody of the present invention can be produced, for example, by immunizing, with the above-defined mammalian CTGFs, "non-human transgenic mammals which are capable of producing human antibodies" such as "transgenic mice which are capable of producing human antibodies" which can be produced by previously reported methods. By using the above-mentioned usual methods, it is possible to immunize non-human mammals, to prepare and screen hybridomas producing the antibodies, and to prepare the human monoclonal antibody in large quantities (Nature Genetics, Vol. 7, p. 13–21, 1994; Nature Genetics, Vol. 15, p. 146–156, 1997; Published Japanese Translation of PCT International Publication No. Hei 4-504365; Published Japanese Translation of PCT International Publication No. Hei7-509137; Nikkei Science, June edition, p.40–50, 1995; WO94/25585; Nature, Vol. 368, p. 856–859, 1994; Published Japanese Translation of PCT International Publication No. Hei 6-500233, etc.).

The human antibody-producing transgenic mice can be produced, specifically, for example, via the following processes; other human antibody-producing non-human transgenic mammals can be produced in the same manner.

(1) A process for preparing knockout mice in which endogenous immunoglobulin heavy chain gene has been functionally inactivated and the inactivation is done by substituting at least a portion of the endogenous gene locus of the mouse immunoglobulin heavy chain for a drug-resistance gene (the neomycin resistance gene, etc.) through homologous recombination;

(2) A process for preparing knockout mice in which endogenous gene of immunoglobulin light chain (a κ chain gene in particular) has been functionally inactivated and the inactivation is done by substituting at least a portion of the endogenous gene locus of the mouse immunoglobulin light chain for a drug-resistance gene (the neomycin resistance gene, etc.) through homologous recombination;

(3) A process for preparing transgenic mice in which a desired portion of the human immunoglobulin heavy chain gene locus has been integrated into a mouse chromosome, by using a vector, such as yeast artificial chromosome (YAC) vector, capable of transporting mega base genes;

(4) A process for preparing transgenic mice in which a desired portion of the human immunoglobulin light chain (a κ gene in particular) gene locus has been integrated into a mouse chromosome, by using a vector, such as YAC vector, capable of transporting mega base genes;

(5) A process for preparing transgenic mice in which both the mouse endogenous heavy chain and light chain gene loci have been functionally inactivated and both desired portions of the human immunoglobulin heavy chain and light chain genes loci have been integrated in a chromosome, of which preparation is achieved by crossbreeding, in arbitrary order, the knockout mice and the transgenic mice described above in (1) to (4).

The knockout mice mentioned above can be prepared by substituting any suitable region in the mouse endogenous immunoglobulin gene locus for a foreign marker gene (neomycin resistance gene, etc.) through homologous recombination so that the immunoglobulin gene locus can be inactivated so as not to cause a rearrangement of the gene locus.

For example, the method designated as positive-negative selection (PNS) can be used for the inactivation with homologous recombination (Nikkei Science, May edition, p. 52–62, 1994).

The functional inactivation of the immunoglobulin heavy chain locus can be achieved, for example, by introducing a lesion into a portion of the J region or a portion of the C region (the $C\mu$ region, for example). The functional inactivation of the immunoglobulin light chain locus can also be achieved, for example, by introducing a lesion into a portion of the J region, a portion of the C region, or a region extending from the J region to the C region.

The transgenic mouse can be prepared according to the method as usually used for producing a transgenic animal (for example, see "Newest Manual of Animal Cell Experiment", LIC press, Chapter 7, pp.361–408, (1990)). Specifically, for example, a transgenic mouse can be produced as follows. Hypoxanthine-guanine phosphoribosyl transferase (HPRT)-negative embryonic stem cells (ES cells) obtained from a normal mouse blastocyst is fused with a yeast cell containing an YAC vector, in which the gene encoding human immunoglobulin heavy chain locus or light chain locus, or its fragment and a HPRT gene have been inserted, by spheroplast fusion method. ES cells in which the foreign gene has been integrated into the mouse endogenous gene are screened by the HAT selection method. Then, the ES cells screened are microinjected into a fertilized egg (blastocyst) obtained from another normal mouse (Proc. Natl. Acad. Sci. USA, Vol.77, No.12, pp.7380–7384 (1980); U.S. Pat. No. 4,873,191). The blastocyst is transplanted into the uterus of another normal mouse as the foster mother. Then, chimeric transgenic mice are born from the foster mother mouse. By mating the chimeric transgenic mice with normal mice, heterozygous transgenic mice are obtained. By mating the heterozygous transgenic mice with each other, homozygous transgenic mice are obtained according to Mendel's laws.

The "chimeric monoclonal antibody" of the present invention is a monoclonal antibody prepared by genetic engineering, whose variable region is non-human mammal (e.g. mice, rats, hamsters, and so forth) immunoglobulin-derived variable region and whose constant region is human immunoglobulin-derived constant region and is exemplified by mouse/human chimeric antibody.

The constant region derived from human immunoglobulin has the amino acid sequence inherent in each isotype such as IgG (IgG1, IgG2, IgG3 and IgG4), IgM, IgA, IgD, and IgE. The constant region of the recombinant chimeric monoclonal antibody of the present invention can be that of human immunoglobulin belonging to any isotype. Preferably, it is the constant region of human IgG.

The chimeric monoclonal antibody of the present invention can be produced, for example, as follows. Needless to say, the production method is not limited thereto.

For example, mouse/human chimeric monoclonal antibody can be prepared, by referring to Experimental Medicine: SUPPLEMENT, Vol. 1.6, No.10 (1988); and Examined Published Japanese Patent Application (JP-B) No. Hei 3-73280. Namely, it can be prepared by ligating $C_H$ gene (C gene encoding the constant region of H chain) obtained from the DNA encoding human immunoglobulin to the downstream of active $V_H$ genes (rearranged VDJ gene encoding the variable region of H chain) obtained from the DNA encoding mouse monoclonal antibody isolated from the hybridoma producing the mouse monoclonal antibody, and by ligating the $C_L$ gene (C gene encoding the constant region of L chain) obtained from the DNA encoding human immunoglobulin to the downstream of active $V_L$ genes (rearranged VJ gene encoding the variable region of L chain) obtained from the DNA encoding the mouse monoclonal antibody isolated from the hybridoma, and operably inserting those into the same or different vectors in an expressible manner, followed by transformation of host cells with the expression vector, and cultivation of the transformants.

Specifically, DNAs are first extracted from mouse monoclonal antibody-producing hybridoma by the usual method, digested with appropriate restriction enzymes (for example, EcoRI and HindIII), electrophoresed (using, for example, 0.7% agarose gel), and analyzed by Southern blotting. After the electrophoresed gel is stained, for example, with ethidium bromide and photographed, the gel is given marker positions, washed twice with water, and soaked in 0.25M HCl for 15 minutes. Then, the gel is soaked in 0.4 N NaOH solution for 10 minutes with gentle stirring. The DNAs are transferred to a filter for 4 hours following the usual method. The filter is recovered and washed twice with 2×SSC. After the filter is sufficiently dried, it is baked at 75° C. for 3 hours, treated with 0.1×SSC/0.1% SDS at 65° C. for 30 minutes, and then soaked in 3×SSC/0.1% SDS. The filter obtained is treated with prehybridization solution in a plastic bag at 65° C. for 3 to 4 hours.

Next, $^{32}$P-labeled probe DNA and hybridization solution are added to the bag and reacted at 65° C. about 12 hours. After hybridization, the filter is washed under an appropriate salt concentration, reaction temperature, and time (for example, 2×SSC-0.1% SDS, room temperature, 10 minutes). The filter is put into a plastic bag with a little 2×SSC, and subjected to autoradiography after the bag is sealed. Rearranged VDJ gene and VJ gene encoding H chain and L chain of mouse monoclonal antibody respectively are identified by Southern blotting mentioned above. The region comprising the identified DNA fragment is fractionated by sucrose density gradient centrifugation and inserted into a phage vector (for example, Charon 4A, Charon 28, λEMBL3, λEMBL4, etc.). E. coli (for example, LE392, NM539, etc.) are transformed with the phage vectorto generate a genomic library. The genomic library is screened by plaque hybridization such as the Benton-Davis method (Science, Vol.196, pp.180–182 (1977)) using appropriate probes (H chain J gene, L chain (κ) J gene, etc.) to obtain positive clones comprising rearranged VDJ gene or VJ gene respectively. By making the restriction map and determining the nucleotide sequence of the clones obtained, it is confirmed that genes comprising the desired, rearranged $V_H$ (VDJ) gene or $V_L$ (VJ) gene have been obtained. Separately, human $C_H$ gene and human $C_L$ gene used for chimerization are isolated. For example, when a chimeric antibody with human IgG1 is produced, $C\gamma_1$, gene is isolated as a $C_H$ gene, and Cκ gene is also isolated as a $C_L$ gene, are isolated. These genes can be isolated from human genomic library with mouse $C\gamma_1$ gene and mouse Cκ gene, corresponding to human $C\gamma_1$ gene and human Cκ gene, respectively, as probes, taking advantage of the high homology between the nucleotide sequences of mouse immunoglobulin gene and that of human immunoglobulin gene.

Specifically, DNA fragments comprising human Cκ gene and an enhancer region are isolated from human λ Charon 4A HaeIII-AluI genomic library (Cell, Vol.15, pp.1157–1174 (1978)), for example, using a 3 kb HindIII-BamHI fragment from clone Ig146 (Proc. Natl. Acad. Sci. USA, Vol.75, pp.4709–4713 (1978)) and a 6.8 kb EcoRI fragment from clone MEP10 (Proc. Natl. Acad. Sci. USA, Vol.78, pp.474–478 (1981)) as probes. In addition, for example, after human fetal hepatocyte DNA is digested with HindIII and fractioned by agarose gel electrophoresis, a 5.9 kb fragment is inserted into λ788 and then human $C\gamma_1$ gene is isolated with the probes mentioned above.

Using mouse $V_H$ gene, mouse $V_L$ gene, human $C_H$ gene, and human $C_L$ gene so obtained, and taking promoter region and enhancer region into consideration, human $C_H$ gene is inserted downstream of mouse $V_H$ gene and human $C_L$ gene is inserted downstream of mouse $V_L$ gene in an expression vector such as pSV2gpt or pSV2neo with appropriate restriction enzymes and DNA ligase following the usual method. In this case, chimeric genes of mouse $V_H$ gene/human $C_H$ gene and mouse $V_L$ gene/human $C_L$ gene can be respectively inserted into a same or different expression vector.

Chimeric gene-inserted expression vector(s) thus prepared are introduced into myelomas (e.g., P3×63.Ag8.653 cells or SP210 cells) that do not produce antibodies by the protoplast fusion method, DEAE-dextran method, calcium phosphate method, or electroporation method. The transformants are screened by cultivating in a medium containing a drug corresponding to the drug resistance gene inserted into the expression vector and, then, cells producing desired chimeric monoclonal antibodies are obtained.

Desired chimeric monoclonal antibodies are obtained from the culture supernatant of antibody-producing cells thus screened.

The "humanized monolonal antibody (CDR-grafted antibody)" of the present invention is a monoclonal antibody prepared by genetic engineering and specifically means a humanized monoclonal antibody wherein a portion or the whole of the complementarity determining regions of the hyper-variable region are derived from the those of the hyper-variable region from non-human mammal (mouse, rat, hamster, etc.) monoclonal antibody, the framework regions of the variable region are derived from those of the variable region from human immunoglobulin, and the constant region is derived from that from human-immunoglobulin.

The complementarity determining regions of the hyper-variable region exists in the hyper-variable region in the variable region of an antibody and means three regions which directly binds, in a complementary manner, to an antigen (complementarity-determining residues, CDR1, CDR2, and CDR3). The framework regions of the variable region mean four comparatively conserved regions intervening upstream, downstream or between the three complementarity-determiningregions (frame work region, FR1, FR2, FR3, and FR4).

In other words, a humanized monoclonal antibody means that in which the whole region except a portion, or the whole region, of the complementarity determining regions of the hyper-variable region of a nonhuman mammal-derived monoclonal antibody have been replaced with their corresponding regions derived from human immunoglobulin.

The constant region derived from human immunoglobulin has the amino acid sequence inherent in each isotype such as IgG (IgG1, IgG2, IgG3, IgG4), IgM, IgA, IgD, and IgE. The constant region of a humanized monoclonal antibody in the present invention can be that from human immunoglobulin belonging to any isotype. Preferably, it is the constant region of human IgG. The framework regions of the constant region derived from human immunoglobulin are not particularly limited.

The humanized monoclonal antibody of the present invention can be produced, for example, as follows. Needless to say, the production method is not limited thereto.

For example, a recombinant humanized monoclonal antibody derived from mouse monoclonal antibody can be prepared by genetic engineering, referring to Published Japanese Translations of PCT International Publication No. Hei 4-506458 and Unexamined Published Japanese Patent Application (JP-A) No. Sho 62-296890. Namely, at least one mouse H chain CDR gene and at least one mouse L chain CDR gene corresponding to the mouse H chain CDR gene are isolated from hybridomas producing mouse monoclonal antibody, and human H chain gene encoding the whole region except human H chain CDR corresponding to mouse H chain CDR mentioned above and human L chain gene encoding the whole region except human L chain CDR corresponding to mouse L chain CDR mentioned above are isolated from human immunoglobulin genes.

The mouse H chain CDR gene(s) and the human H chain gene(s) so isolated are inserted, in an expressible manner, into an appropriate vector so that they can be expressed. Similarly, the mouse L chain CDR gene(s) and the human L chain gene(s) are inserted, in an expressible manner, into another appropriate vector so that they can be expressed. Alternatively, the mouse H chain CDR gene(s)/human H chain gene(s) and mouse L chain CDR gene(s)/human L chain gene(s) can be inserted, in an expressible manner, into the same expression vector so that they can be expressed. Host cells are transformed with the expression vector thus prepared to obtain transformants producing humanized monoclonal antibody. By cultivating the transformants, desired humanized monoclonal antibody is obtained from culture supernatant.

The "monoclonal antibody" of the invention includes "a portion" of the monoclonal antibody as well. The "portion of an antibody" used in the present invention means a partial region of the antibody, preferably monoclonal antibody of the present invention as mentioned above, and specifically, means $F(ab')_2$, Fab', Fab, Fv (variable fragment of antibody), sFv, dsFv (disulfide stabilized Fv), or dAb (single domain antibody) (Exp. opin. Ther. Patents, Vol.6, No.5, pp.441–456 (1996)).

"$F(ab')_2$" and "Fab'" can be produced by treating immunoglobulin (monoclonal antibody) with a protease such as pepsin and papain, and means an antibody fragment generated by digesting immunoglobulin near the disulfide bonds existing between the hinge regions in each of the two H chains. For example, papain cleaves IgG upstream of the disulfide bonds existing between the hinge regions in each of the two H chains to generate two homologous antibody fragments in which an L chain composed of $V_L$ (L chain variable region) and $C_L$ (L chain constant region), and an H chain fragment composed of $V_H$ (H chain variable region) and $C_H\gamma 1$ ($\gamma 1$ region in the constant region of H chain) are connected at their C terminal regions through a disulfide bond. Each of these two homologous antibody fragments is called Fab'. Pepsin also cleaves IgG downstream of the disulfide bonds existing between the hinge regions in each of the two H chains to generate an antibody fragment slightly larger than the fragment in which the two above-mentioned Fab' are connected at the hinge region. This antibody fragment is called $F(ab')_2$.

The "monoclonal antibody producing cells" or "recombinant monoclonal antibody producing cells" of this invention mean any cells producing the above-described monoclonal antibody of this invention. Specific examples include the cells described in (1) to (3) below.

(1) monoclonal antibody-producing B cells that are obtainable from the above-described non-human mammal or human antibody producing transgenic mouse (or other transgenic non-human mammals) that produces a monoclonal antibody reactive with CTGF, which animal can be produced by immunizing the animal with the above-defined mammalian CTGF (preferably human CTGF) or a portion thereof or cells secreting the CTGF, etc.;

(2) the above-described hybridomas prepared by fusing antibody producing B cells obtained described above with myelomas derived from mammals; and (3) monoclonal antibody producing transformants (recombinant cells) obtained by transforming other cells than the monoclonal antibody producing B cells and hybridomas (e.g. Chinese hamster ovarian (CHO) cells, Baby hamster kidney (BHK) cells, etc.) with genes (either the heavy chain-encoding gene or the light chain encoding gene, or both) encoding the monoclonal antibody isolated from the monoclonal antibody producing B cells or hybridomas.

The monoclonal antibody producing transformants (recombinant cells) of (3) mean recombinant cells producing a recombinant product of the monoclonal antibody produced by B cells of (1) or hybridomas of (2). These antibody producing transformants can be produced using known recombinant technology as used for the above-described chimeric monoclonal antibody and humanized monoclonal antibody.

The term "monoclonal antibody comprising a property substantially equivalent to" as referred to in the present invention indicates that, when biological properties of two monoclonal antibodies are compared with each other, one monoclonal antibody is not significantly different from the other in at least the following biological properties:

(1) the reactivity to CTGF derived from a particular animal, which is used as an immunogen for immunizing a non-human mammal to prepare the monoclonal antibody;

(2) the reactivity to any CTGF derived from animals other than the particular animal (namely, crossreactivity);

(3) the properties measured by a variety of experiments described below in the examples.

The term "mammalian antiserum" as referred to in the present invention indicates a serum containing antibody reactive to the monoclonal antibody of the present invention or a portion thereof. The antiserum can be produced, according to the above-described method described in the production of monoclonal antibody, by immunizing mammals such as mice, rats, guineapigs, rabbits, goats, pigs orbovine, preferably rats, guinea pigs, rabbits or goats, with the above-mentioned monoclonal antibody or a portion thereof as an immunogen.

The term "insoluble carrier" as referred to in the present invention indicates a supporting material thereon used for immobilizing the monoclonal antibbdy or a portion thereof (antibody fragment) of the present invention, or CTGF in samples (for example, body fluids such as plasma, culture supernatant, supernatant fluids obtained by centrifugation, etc.) by physical adsorption or chemical bonding.

The insoluble carrier is exemplified below in (A) and (B):

(A) plates, containers having internal spaces such as test tubes or tubes, beads (microbeads in particular), balls, filters or membranes, made of water-insoluble materials, for example, glass or plastics such as polystyrene resin, polycarbonate resin, silicone resin or nylon resin;

(B) insoluble carriers, used for affinity chromatography, such as cellulose carriers, agarose carriers, polyacrylamide carriers, dextran carriers, polystyrene carriers, polyvinyl alcohol carriers, poly(amino acid) carriers or porous silica carriers.

The term "antibody-immobilized insoluble carrier" as referred to in the present invention indicates the above-defined insoluble carrier on which the monoclonal antibody (or a portion of the antibody, namely an antibody fragment) of this invention is immobilized by physical adsorption or chemical bonding. These insoluble carriers with immobilized antibodies are usable for the detection, assay, separation or purification of CTGF in samples (for example, body fluids such as serum and plasma; culture supernatant; the supernatant fluids obtained by centrifugation, etc.).

The insoluble carriers shown above in (A) can be used for the detection and the assay; from the standpoint of the simplicity of operation and the simultaneous processing of many samples, in particular, the multi-well microtiter plates, which are made of plastics and have many wells, such as 96-well microtiter plates or 48-well microtiter plates, are used preferably as the insoluble carrier in the assay for assaying CTGF. The filters or membranes shown above in (A), or the insoluble carriers shown above in (B), are usable for the separation or the purification.

A "labeling agent capable of providing a detectable signal through the reaction with the labeling agent alone or together with other substances" as referred to in this invention means a substance used for converting the monoclonal antibody or a portion thereof (antibody fragment) described above, or a CTGF standard into detectable forms; the conversion can be performed by the physical binding or chemical bonding between the labeling agent and the monoclonal antibody or a portion thereof, or between the labeling agent and the CTGF standard material.

Specifically, the labeling agent includes enzymes, fluorescent materials, chemiluminescent materials, biotin, avidin or radioisotopes, etc., more specifically, enzymes such as peroxidase (for example, horseradish peroxidase), alkaline phosphatase, β-D-galactosidase, glucose oxidase, glucose-6-phosphate dehydrogenase, alcohol dehydrogenase, malate dehydrogenase, penicillinase, catalase, apo-glucose oxidase, urease, luciferase or acetylcholinesterase; fluorescent materials such as fluorescein isothiocyanate, phycobiliprotein, chelating compounds of rare-earth metals, dansyl chloride or tetramethylrhodamine isothiocyanate; radioisotopes such as $^3H$, $^{14}C$, $^{125}I$ or $^{131}I$; biotin; avidin; or chemiluminescent materials.

Radioisotopes and fluorescent materials, even when used alone, give a detectable signal. On the other hand, enzymes, chemiluminescent materials, biotin, and avidin give no detectable signals, when used alone. In these cases, one or more substances are needed with the substances in order to give a detectable signal. For example, when the substance is an enzyme, at least a substrate for the enzyme is necessary to give a detectable signal. Various types of substrates are selectable depending on the methods for measuring the enzyme activity (colorimetry, immunofluorescence method, bioluminescence method or chemiluminescence method, etc.). For example, hydrogen peroxide is used as a substrate for peroxidase. When biotin is selected, avidin or enzyme-conjugated avidin is used for the reaction with biotin generally but not always. According to needs, various coloring agents are further used for the reaction depending on the type of the substrate.

The terminologies, "labeled antibody" and "labeled mammalian CTGF standard" as referred to in the present invention indicate, respectively, monoclonal antibody (or antibody fragment) and CTGF labeled with the above-mentioned various labeling agents. The labeled antibody and labeled standard can be used to detect, assay, separate or purify CTGFs in samples (for example, body fluid samples such as serum and plasma; culture supernatants; or the supernatant fluids obtained by centrifugation, etc.). In the present invention, any of the above-mentioned labeling agents are usable. However, biotin or enzymes such as peroxidase are used favorably for the labeling from the standpoint of the high detection sensitivity or high assay sensitivity and the simplicity of operation.

Being different from a CTGF of an unknown concentration (amount) in a sample, the "CTGF standard" is a CTGF isolated previously and the standard adjustable to any desired concentration thereof to suit the purpose of each assay. For example, the standard substance can be used for the preparation of calibration curves.

The term "immunoassay" as referred to in the present invention means the method of detecting or assaying the antigens in samples (for example, body fluid samples such as plasma; culture supernatants; or the supernatant fluids obtained by centrifugation) based on the principle of antigen-antibody reaction. In the present invention, for the immunoassay, one or more monoclonal antibodies (or antibody fragment(s)) to be used as the antibody in the antigen-antibody reaction are selected from the above-mentioned monoclonal antibodies (or antibody fragment) reactive to the mammalian CTGF of the present invention, the above-mentioned antibody-immobilized insoluble carrier (or antibody fragment-immobilized insoluble carrier) and the above-mentioned labeled antibody (or labeled antibody fragment) as well as the antigen is the mammalian CTGF, but otherwise previously known immunoassay methods are applicable in the assay.

Specifically, the immunoassay is exemplified by single antibody solid phase method, two-antibodies liquid phase method, two-antibodies solid phase method, sandwich method, enzyme multiplied immunoassay technique (EMIT method), enzyme channeling immunoassay, enzyme modulator mediated enzyme immunoassay (EMMIA), enzyme inhibitor immunoassay, immuno enzymometric assay, enzyme enhanced immunoassay or proximal linkage immunoassay all of which are described in "Enzyme Immunoassay (3rd Ed., eds., Eiji Ishikawa et al., Igakushoin, 1987); or the one-pot method which is described in JP-B Hei 2-39747.

In this invention, any of these immunoassays can be selected appropriately to suit each assay purpose. However, from the standpoint of the simplicity of operation and/or the economical advantage, and especially when considering the clinical applicability, the sandwich method, the one pot method, the single antibody solid phase method and the two-antibodies solid phase method are preferably used in this invention; more preferable are the sandwich method and the one pot method. Particularly preferable is the sandwich method using a labeled antibody prepared by labeling the monoclonal antibody of the present invention with an enzyme or biotin as well as using an antibody-immobilized insoluble carrier prepared by immobilizing the monoclonal antibody on a multi-well microplate having many wells thereon, such as a 96-well microplate; another particularly preferable method is the one-pot method using a labeled antibody prepared by labeling the monoclonal antibody of the present invention with an enzyme or biotin as well as using an antibody-immobilized insoluble carrier prepared by immobilizing the monoclonal antibody on beads, such as microbeads, or small balls.

A specific example of a particularly preferable embodiment is the sandwich method or the one-pot method using a labeled antibody prepared by labeling the monoclonal antibody "8-86-2," as indicated in FIG. 1, with an enzyme or biotin, as well as using an antibody-immobilized insoluble carrier prepared by immobilizing the monoclonal antibody "8-64-6" or "13-51-2," as indicated in FIG. 1, on the microplate or the microbeads.

Human and mouse CTGFs can be detected or quantified in high sensitivity by immunoassays using the monoclonal antibody "8-64-6"-immobilized insoluble carrier, in combination with the monoclonal antibody "8-86-2" labeled with an enzyme or biotin. Rat CTGF (first disclosed in the present application) and mouse CTGF can be detected or assayed in high sensitivity by the immunoassay using the monoclonal antibody "13-51-2"-immobilized insoluble carrier, in combination with the monoclonal antibody "8-86-2" labeled with an enzyme or biotin.

The sandwich method, the one-pot method, the single antibody solid phase method, and the two-antibodies liquid phase method are described in detail herein below.

The sandwich method corresponds to the method described above in (50) of the present invention, and specifically, is an immunoassay that comprises at least the following steps (a) and (b):

(a) reacting a sample with the antibody-immobilized insoluble carrier of the present invention; and (b) reacting a labeled antibody of the present invention with the antigen-antibody complex formed by the binding between the antibody-immobilized insoluble carrier and mammalian CTGF in the sample.

According to the present invention, a specific example of the method of assaying human or mouse CTGF is indicated below, in which the "antibody-immobilized insoluble carrier" is an "antibody-immobilized microplate" prepared by immobilizing the monoclonal antibody 8-64-6" as indicated in FIG. 1 on a microplate, and the "labeled antibody" is the monoclonal antibody "8-86-2", as indicated in FIG. 1, labeled with biotin or an enzyme such as peroxidase; the method comprises, for example, the steps described below, but the method is not to be construed as being restricted thereto.

Not only mouse CTGF but also rat CTGF (first disclosed in the present application) can be assayed by the same procedures as indicated below, when the "antibody-immobilized insoluble carrier" is an "antibody-immobilized microplate" prepared by immobilizing the monoclonal antibody "13-51-2" as indicated in FIG. 1 on a microplate and the "labeled antibody" is the monoclonal antibody "8-86-2", as indicated in FIG. 1, labeled with biotin or an enzyme such as peroxidase.

(Step 1) preparing an antibody-immobilized microplate by immobilizing the monoclonal antibody "18-64-6" of the present invention on a microplate;

(Step 2) reacting a sample such as a human or mouse serum with the monoclonal antibody immobilized on the antibody-immobilized microplate by adding the sample to the microplate;

(Step 3) washing the microplate to remove the unreacted sample from the microplate;

(Step 4) preparing a labeled antibody by labeling the monoclonal antibody "8-86-2" of the present invention with biotin or an enzyme such as peroxidase;

(Step 5) reacting the labeled antibody with the antigen-antibody complex formed through the reaction between human or mouse CTGF in the sample and the monoclonal antibody immobilized on the microplate, by adding the labeled antibody to the microplate washed in Step 3;

(Step 6) washing out the unreacted labeled antibody from the microplate;

(Step 7) reacting the labeling agent moiety of the labeled antibody with a substrate selected depending on the type of the enzyme used (when the labeled antibody used in Step 5 is labeled with an enzyme such as peroxidase), avidin or enzyme-conjugated avidin avidin (when the labeled antibody used in Step 5 is labeled with biotin), by adding, if necessary together with a coloring agent, the substrate, or avidin or enzyme-conjugated avidin to the microplate;

(Step 8) reacting a substrate for the enzyme selected depending on the type of the enzyme conjugated with avidin, with the enzyme conjugated with avidin, by adding the substrate, when enzyme-conjugated avidin is used in Step 7;

(Step 9) stopping the enzyme reaction and the coloring reaction by adding a reaction stop solution into the reaction mixture of step 7 or 8; and (Step 10) measuring the calorimetric intensity, fluorescence intensity or luminescence intensity.

The one-pot method corresponds to each of the methods described above in (50), (51) and (52) of the present invention.

Specifically, the first is the immunoassay method comprising at least the following steps (a) and (b);

(a) reacting a sample with an antibody-immobilized insoluble carrier of the present invention; and (b) reacting a labeled antibody of the present invention with the antigen-antibody complex formed by the binding between the antibody-immobilized insoluble carrier and mammalian CTGF in the sample.

The second is the immunoassay method comprising at least the following steps (a) and (b);

(a) reacting a sample with a labeled antibody of the present invention; and (b) reacting an antibody-immobilized insoluble carrier of the present invention with the antigen-antibody complex formed by the binding between the labeled antibody and mammalian CTGF in the sample.

The third is the immunoassay method comprising at least the following step (a);

(a) reacting a mixture of an antibody-immobilized insoluble carrier of the present invention, a labeled antibody of the present invention and a sample.

According to the present invention, a specific example of the method of assaying human or mouse CTGF is indicated below, in which the "antibody-immobilized insoluble carrier" is "antibody-immobilized microbeads" prepared by immobilizing the monoclonal antibody "8-64-6" as indicated in FIG. 1 on microbeads, and the "labeled antibody" is the monoclonal antibody "8-86-2", as indicated in FIG. 1, labeled with biotin or an enzyme such as peroxidase; the method comprises, for example, the steps described below, but the method is not to be construed as being restricted thereto.

Not only mouse CTGF but also rat CTGF (first disclosed in the application) can be assayed by the same procedures as indicated below, when the "antibody-immobilized insoluble carrier" is "antibody-immobilized microbeads" prepared by immobilizing the monoclonal antibody "13-51-2" as indicated in FIG. 1 on microbeads and the "labeled antibody" is the monoclonal antibody "8-86-2", as indicated in FIG. 1, labeled with biotin or an enzyme such as peroxidase.

The first method comprises the following steps:

(Step 1) preparing antibody-immobilized microbeads by immobilizing the monoclonal antibody "8-64-6", of the present invention on microbeads;

(Step 2) reacting a sample such as a human or mouse serum with the monoclonal antibody immobilized on the microbeads by adding the sample and the antibody-immobilized microbeads together with a buffer solution into a container having internal spaces such as a test tube, microplate, or tube;

(Step 3) washing the beads to remove the liquid content from the container;

(Step 4) preparing a labeled antibody by labeling the monoclonal antibody "8-86-2" with biotin or an enzyme such as peroxidase;

(Step 5) reacting the labeled antibody with the antigen-antibody complex formed through the reaction between the human or mouse CTGF in the sample and the monoclonal antibody immobilized on the beads by adding the labeled antibody into the container containing the beads washed in Step 3;

(Step 6) removing the unreacted labeled antibody by removing the liquid content from the container and washing the beads;

(Step 7) reacting the labeling agent moiety of the labeled antibody with a substrate selected depending on the type of the enzyme used (when the labeled antibody used in Step 5 is labeled with an enzyme such as peroxidase), avidin or the enzyme-conjugated avidin (when the labeled antibody used in Step 5 is labeled with biotin) by adding, if necessary together with a coloring agent, the substrate, or avidin or enzyme-conjugated avidin into the container containing the beads washed in Step 6;

(Step 8) reacting a substrate for the enzyme selected depending on the type of the enzyme conjugated with avidin, with the enzyme conjugated with avidin by adding the substrate, when enzyme-conjugated avidin is used in Step 7;

(Step 9) stopping the enzyme reaction and the coloring reaction by adding a reaction stop solution into the reaction mixture of Step 7 or Step 8; and (Step 10) measuring the calorimetric intensity, fluorescence intensity or luminescence intensity.

The second method comprises the following steps:

(Step 1) preparing a labeled antibody by labeling the monoclonal antibody "8-86-2", of the present invention with biotin or an enzyme such as peroxidase;

(Step 2) reacting a sample such as a human or mouse serum with the labeled antibody by adding the sample and the labeled antibody together with a buffer solution into a container having internal spaces such as a test tube, microplate or tube;

(Step 3) preparing antibody-immobilized microbeads by immobilizing the monoclonal antibody "8-64-6" of the present invention on microbeads;

(Step 4) reacting the monoclonal antibody immobilized on the beads with the antigen-antibody complex formed through the reaction between the labeled antibody and human CTGF or mouse CTGF in the sample by adding the beads into the reaction system in Step 3;

(Step 5) removing the unreacted labeled antibody by removing the liquid content from the container and washing the beads;

(Step 6) reacting the labeling agent moiety of the labeled antibody with a substrate selected depending on the type of the enzyme used (when the labeled antibody used in Step 2 is labeled with an enzyme such as peroxidase), avidin or the enzyme-conjugated avidin (when the labeled antibody used in Step 2 is labeled with biotin) by adding, if necessary together with a coloring agent, the substrate, or avidin or enzyme-conjugated avidin into the container containing the beads washed in Step 5;

(Step 7) reacting a substrate selected depending on the type of the enzyme conjugated with avidin, with the enzyme conjugated with avidin by adding the substrate, when enzyme-conjugated avidin is used in Step 6;

(Step 8) stopping the enzyme reaction and the coloring reaction by adding a stop solution to the reaction system in Step 6 or 7; and (Step 9) measuring the colorimetric intensity, fluorescence intensity or luminescence intensity.

The third method comprises the following steps:

(Step 1) preparing antibody-immobilized microbeads by immobilizing the monoclonal antibody "8-64-6", of the present invention on the microbeads;

(Step 2) preparing a labeled antibody by labeling the monoclonal antibody "8-86-2" of the present invention with biotin or an enzyme such as peroxidase;

(Step 3) reacting the labeled antibody and a sample such as a human or mouse serum simultaneously with the monoclonal antibody immobilized on microbeads by adding the sample and the antibody-immobilized microbeads prepared in Step 1 and the labeled antibody prepared in Step 2 together with a buffer solution into a container having internal spaces such as a test tube, plate, or tube.

(Step 4) removing the unreacted labeled antibody by removing the liquid content from the container and washing the beads;

(Step 5) reacting the labeling agent moiety of the labeled antibody with a substrate selected depending on the type of the enzyme used (when the labeled antibody used in Step 3 is labeled with an enzyme such as peroxidase), avidin or the enzyme-conjugated avidin (when the labeled antibody used in Step 3 is labeled with biotin) by adding, if necessary together with a coloring agent, the substrate, or avidin or enzyme-conjugated avidin into the container containing the beads washed in Step 4;

(Step 6) reacting a substrate selected depending on the type of the enzyme conjugated with avidin, with the enzyme conjugated with avidin by adding the substrate, when enzyme-conjugated avidin is used in Step 5;

(Step 7) stopping the enzyme reaction and the coloring reaction by adding a stop solution to the reaction system in Step 5 or 6; and (Step 8) measuring the colorimetric intensity, fluorescence intensity or luminescence intensity.

The single antibody solid phase method corresponds to the method described above in (53) of the present invention, and specifically, the immunoassay method that comprises at least the following step (a):

(a) reacting a sample and mammalian CTGF standard labeled with a labeling agent capable of providing a detectable signal by itself or by reacting with other substances, with an antibody-immobilized insoluble carrier of the present invention.

A specific example of the method of assaying human or mouse CTGF according to the present invention is indicated below, in which the "antibody-immobilized insoluble carrier" is an "antibody-immobilized microplate" prepared by immobilizing the monoclonal antibody "8-64-6" as indicated in FIG. 1 on a microplate and widely used biotin or enzyme such as peroxidase is used here as a "labeling agent"; the method comprises, for example, the steps described below, but the method is not to be construed as being restricted thereto. Not only mouse CTGF but also rat CTGF (first disclosed in the application) can be assayed by the same procedures as indicated below, when the "antibody-immobilized insoluble carrier" is an "antibody-immobilized microplate" prepared by immobilizing the monoclonal antibody "13-51-2" as indicated in FIG. 1 on a microplate and widely used biotin or an enzyme such as peroxidase is use as the "labeling agent."

(Step 1) preparing an antibody-immobilized microplate by immobilizing the monoclonal antibody "8-64-6" on a microplate;

(Step 2) preparing a labeled CTGF standard by labeling the standard with biotin or an enzyme such as peroxidase;

(Step 3) reacting a sample such as a human or mouse serum and the labeled CTGF standard competitively with the monoclonal antibody immobilized on the microplate by adding the sample and the labeled standard to the microplate;

(Step 4) washing out the unreacted labeled standard from the microplate;

(Step 5) reacting the labeling agent moiety of the labeled standard with a substrate selected from depending on the type of the enzyme used (when the labeled standard used in Step 3 is labeled with an enzyme such as peroxidase), avidin or enzyme-conjugated avidin (when the labeled standard in Step 3 is labeled with biotin) by adding, if necessary together with a coloring agent, the substrate, or avidin or enzyme-conjugated avidin to the microplate washed in Step 4;

(Step 6) reacting a substrate selected depending on the type of the enzyme conjugated with avidin, with the enzyme conjugated with avidin by adding the substrate, when enzyme-conjugated avidin is used in Step 5;

(Step 7) stopping the enzyme reaction and the coloring reaction by adding a stop solution to the microplate; and (Step 8) measuring the colorimetric intensity, fluorescence intensity or luminescence intensity.

The two antibodies solid phase method corresponds to the methods described above in (54) and (55) of the present invention.

Specifically, the first is the immunoassay method comprising at least the following steps (a) and (b):

(a) reacting the monoclonal antibody of the present invention with a mixture comprising a sample and a mammalian CTGF standard labeled with a labeling agent capable of providing a detectable signal by itself or by reacting with other substances; and, (b) reacting a mammalian antiserum reactive to the monoclonal antibody with the antigen-antibody complex formed through binding of the monoclonal antibody and the mammalian CTGF in the sample or the labeled mammalian CTGF standard.

The second is the immunoassay method comprising at least the following steps (a) to (c):

(a) reacting a monoclonal antibody of the present invention with a sample;

(b) reacting a mammalian CTGF standard labeled with a labeling agent capable of providing a detectable signal by itself or by reacting other substances, with the reaction mixture in Step (a); and, (c) reacting a mammalian antiserum reactive to the monoclonal antibody with the antigen-antibody complex formed through the binding of the monoclonal antibody and the mammalian CTGF in the sample or the labeled mammalian CTGF standard.

A specific example of the method of assaying human or mouse CTGF according to the present invention is indicated below, in which the "monoclonal antibody" is the monoclonal antibody "8-64-6" or the monoclonal antibody "8-86-2", as indicated in FIG. 1 and widely used biotin or an enzyme such as peroxidase is used as the "labeling agent"; the method comprises, for example, the steps described below, but the method is not to be construed as being restricted thereto.

Not only mouse CTGF but also rat CTGF (first disclosed in the application) can be assayed by the same procedures as indicated below, when the "monoclonal antibody" is the monoclonal antibody "13-51-2" as indicated in FIG. 1 and widely used biotin or an enzyme such as peroxidase is used as the "labeling agent."

The first method comprises the following steps:

(Step 1) preparing the labeled CTGF standard by labeling a human or mouse CTGF standard with biotin or an enzyme such as peroxidase;

(Step 2) reacting a sample such as a human or mouse serum and the labeled CTGF standard prepared in Step 1 competitively with the monoclonal antibody "18-64-6" or "8-86-2" of the present invention by adding a mixture comprising the sample and the labeled CTGF standard into a container having internal spaces such as a test tube, plate or tube and by subsequently adding thereto the monoclonal antibody;

(Step 3) reacting an antiserum, derived from mammals except mice, reactive to the mouse monoclonal antibody, such as a goat anti-mouse γ-globulin antiserum, with the antigen-antibody complex, formed in Step 2, consisting of the monoclonal antibody and the mammalian CTGF in the sample or the labeled mammalian CTGF standard, to give the resulting precipitated immune-complex;

(Step 4) separating the precipitated complex by the centrifugation of the reaction mixture of Step 3;

(Step 5) reacting the labeling agent moiety of the labeled standard with a substrate selected depending on the type of the enzyme used (when the labeled standard used in Step 2 is labeled with an enzyme such as peroxidase), avidin or the enzyme-conjugated avidin (when the labeled standard used in Step 2 is labeled with the biotin) by adding, if necessary together with a coloring agent, the substrate, or avidin or enzyme-conjugated avidin to the precipitated complex separated in Step 4;

(Step 6) reacting a substrate selected depending on the type of the enzyme conjugated with avidin, with the enzyme conjugated with avidin by adding the substrate, when enzyme-conjugated avidin is used in Step 5;

(Step 7) stopping the enzyme reaction and the coloring reaction by adding a stop solution to the reaction system in Step 5 or 6; and, (Step 8) measuring the colorimetric intensity, fluorescence intensity or luminescence intensity.

The second method comprises the following steps:

(Step 1) preparing a labeled CTGF standard by labeling a human or mouse CTGF standard with biotin or an enzyme such as peroxidase;

(Step 2) reacting a sample such as a human or mouse serum with the monoclonal antibody "8-64-6" or "8-86-2" of the present invention by adding the sample into a container having internal spaces such as a test tube, plate or tube and by subsequently adding thereto the monoclonal antibody;

(Step 3) reacting the labeled CTGF standard prepared in Step 1 with the remaining unreacted monoclonal antibody, by adding the labeled CTGF standard to the reaction mixture in Step 2;

(Step 4) reacting an antiserum, derived from mammals except mice, reactive to the mouse monoclonal antibody, such as a goat anti-mouse γ-globulin antiserum, with the antigen-antibody complex, formed in Step 2, consisting of the monoclonal antibody and the mammalian CTGF in the sample and/or the antigen-antibody complex, formed in Step 3, consisting of the monoclonal antibody and the labeled mammalian CTGF standard, to give the precipitated immune-complex consisting of the antiserum and the antigen-antibody complex;

(Step 5) separating the precipitated complex by the centrifugation of the reaction mixture of Step 4;

(Step 6) reacting the labeling agent moiety of the labeled standard with a substrate selected depending on the type of the enzyme used (when the labeled standard used in Step 3 is labeled with an enzyme such as peroxidase), avidin or the enzyme-conjugated avidin (when the labeled standard used in Step 3 is labeled with biotin) by adding, if necessary together with a coloring agent, the substrate, or avidin or enzyme-conjugated avidin to the precipitated complex separated in Step 5;

(Step 7) reacting a substrate selected depending on the type of the enzyme conjugated with avidin, with the enzyme conjugated with avidin by adding the substrate, when enzyme-conjugated avidin is used in Step 6;

(Step 8) stopping the enzyme reaction and the coloring reaction are stopped by adding a stop solution to the reaction system in Step 6 or 7, and;

(Step 9) measuring the colorimetric intensity, fluorescence intensity or luminescence intensity.

The "affinity chromatography" as referred to in the present invention indicates the method of separating or purifying the materials of interest in samples (for example, the body fluid samples such as a serum and plasma; culture supernatants; or the supernatant fluids obtained by centrifugation, etc.) by utilizing the interaction (affinity) between a pair of materials, for example, antigen and antibody, enzyme and substrate, or receptor and ligand.

The method of the present invention relates to the method for separating or purifying the mammalian CTGFs in samples (for example, the body fluid samples such as a serum and plasma; culture supernatants; or the supernatant fluids obtained by centrifugation, etc.) by utilizing the antigen-antibody interaction, specifically, the affinity of the monoclonal antibody of the present invention for mammalian CTGFs as antigens; specifically includes, (1) a method for separating CTGF in samples by immobilizing the monoclonal antibody (or antibody fragment) reactive to mammlian CTGF on the above-defined insoluble carriers, such as a filter or a membrane and contacting the sample with the filter or membrane; and (2) a method for separating or purifying CTGF in the samples, by immobilizing, in a usual manner (immobilization by physical adsorption, cross-linking to the carrier polymer, trapping in the carrier matrix or non-covalent bonding, etc.), the inventive monoclonal antibody (or the antibody fragment) reactive to mammalian CTGF on insoluble carriers such as cellulose carriers, agarose carriers, polyacrylamide carriers, dextran carriers, and polystyrene carriers, polyvinyl alcohol carriers, poly(amino acid) carriers or porous silica carriers; by filling a column made of glass, plastics, or stainless, with the insoluble carriers; and by loading and eluting samples (for example, the body fluid samples such as a serum and plasma; culture supernatants; or the supernatant fluids obtained by centrifugation, etc.) through the column (for example, the cylindrical column). The method described above in (2) is in particular designated as affinity column chromatography.

Any of the insoluble carriers are usable as insoluble carriers for affinity column chromatography, as long as the monoclonal antibody (or antibody fragment) of the present invention can be immobilized on the carriers. Such carriers include, for example, commercially available carriers such as SEPHAROSE 2B, SEPHAROSE 4B, SEPHAROSE 6B, CNBR-ACTIVATED SEPHAROSE 4B, AH-SEPHAROSE 4B, CH-SEPHAROSE 4B, ACTIVATED CH-SEPHAROSE 4B, EPOXY-ACTIVATED SEPHAROSE 6B, ACTIVATED THIOL-SEPHAROSE 4B, SEPHADEX, CM-SEPHADEX, ECH-SEPHAROSE 4B, EAH-SEPHAROSE 4B, NHS-ACTIVATED SEPHAROSE or THIOPROPYL SEPHAROSE 6B, etc., all of which are supplied by Pharmacia; BIO-GEL A, CELLEX, CELLEX AE, CELLEX-CM, CELLEX PAB, BIO-GEL P, HYDRAZIDE BIO-GEL P, AMINOETHYL BIO-GEL P, BIO-GEL CM, AFFI-GEL 10, AFFI-GEL 15, AFFI-PREP10, AFFI-GEL HZ, AFFI-PREP HZ, AFFI-GEL 102, CM BIO-GEL A, AFFI-GEL HEPARIN, AFFI-GEL 501 OR AFFI-GEL 601, etc., all of which are supplied by Bio-Rad; CHROMAGEL A, CHROMAGEL P, ENZAFIX P-HZ, ENZAFIX P-SH OR ENZAFIX P-AB, etc., all of which are supplied by Wako Pure Chemical Industries Ltd.; AE-CELLUROSE, CM-CELLUROSE or PAB CELLUROSE etc., all of which are supplied by Serva.

The term "pharmaceutical composition" as referred to in the present invention means a composition useful as a pharmaceutical comprising as an active ingredient the monoclonal antibody of the present invention or a portion thereof, or any of the after-mentioned "CTGF inhibitor", "CTGF production inhibitor" and "substance with the activity to inhibit the CTGF-stimulated proliferation of cells having the capability of proliferating by CTGF stimulation", as well as comprising a "pharmaceutically acceptable carrier."

The "pharmaceutically acceptable carrier" includes an excipient, a diluent, an expander, a disintegrating agent, a stabilizer, a preservative, a buffer, an emulsifier, an aromatic, a colorant, a sweetener, a viscosity increasing agent, a flavor, a dissolving agent, or other additives.

Using one or more of such carriers, a pharmaceutical composition can be formulated into tablets, pills, powders, granules, injections, solutions, capsules, troches, elixirs, suspensions, emulsions, or syrups.

The pharmaceutical composition can be administered orally or parenterally. Other forms for parenteral administration include a solution for external application, suppository for rectal administration, and pessary, prescribed by the usual method, which comprises one or more active ingredient.

The dosage can vary depending on the age, sex, weight, and symptoms of a patient, effect of treatment, administration route, period of treatment, or the kind of active ingredient (protein or antibody mentioned above) contained in the pharmaceutical composition. Usually, the pharmaceutical composition can be administered to an adult in a dose of 10 μg to 1000 mg (or 10 μg to 500 mg) per one administration. Depending on various conditions, the lower dosage may be sufficient in some cases, and a higher dosage may be necessary in other cases.

In particular, the injection can be produced by dissolving or suspending the antibody in a non-toxic, pharmaceutically acceptable carrier such as physiological saline or commercially available distilled water for injections by adjusting the concentration to 0.1 μg antibody/ml carrier to 10 mg antibody/ml carrier.

The injection thus produced can be administered to a human patient in need of treatment in a dose of 1 μg to 100 mg/kg body weight, preferably 50 μg to 50 mg/kg body weight, once or more times a day. Examples of administration routes are medically appropriate administration routes such as intravenous injection, subcutaneous injection, intradermal injection, intramuscular injection, or intraperitoneal injection, preferably intravenous injection.

The injection can also be prepared into a non-aqueous diluent (for example, propylene glycol, polyethylene glycol, vegetable oil such as olive oil, and alcohols such as ethanol), suspension, or emulsion.

The injection can be sterilized by filtration with a bacteria-non-penetratable filter, by mixing bacteriocide, or by irradiation. The injection can be prepared at the time of use. Namely, it is freeze-dried to make a sterile solid composition, and can be dissolved in sterile distilled water for injection or another solvent before use.

The pharmaceutical composition of the present invention is useful for inhibiting the proliferation of various cells having the capability of proliferating (for example, various fibroblast cells, various vascular endothelial cells, and others, etc.) in response to the stimulation of CTGFs from a variety of tissues. Examples of the tissues are, the brain, neck, lung, heart, liver, pancreas, kidney, stomach, large intestine, small intestine, duodenum, bone marrow, uterus, ovary, testis, prostate, skin, mouth, tongue, and blood vessels, and preferably, the lung, liver, kidney or skin.

As described hereinabove, the pharmaceutical composition of the present invention can inhibit the proliferation of cells having the capability of proliferating in response to the stimulation of CTGF. Therefore, the pharmaceutical composition of the present invention is also useful as a pharmaceutical for treating or preventing a variety of diseases associated with the cell proliferation in various tissues mentioned above. Examples of such tissues are the brain, neck, lung, heart, liver, pancreas, kidney, stomach, large intestine, small intestine, duodenum, bone marrow, uterus, ovary, testis, prostate, skin, mouth, tongue, and blood vessels, and preferably, the lung, liver, kidney or skin.

The diseases, to which the pharmaceutical composition of the present invention is applicable for the treatment or prevention, are, for example, fibrotic diseases in various tissues (kidney fibrosis, pulmonary fibrosis, hepatic fibrosis, fibrosis in the skin, etc.), kidney diseases (for example, kidney fibrosis, nephritis, renal failure, etc.), lung diseases (for example, pulmonary fibrosis, pneumonia, etc.), skin diseases (for example, psoriasis, scleroderma, atopy, keloid, etc.), liver diseases (for example, hepatic fibrosis, hepatitis, cirrhosis, etc.), arthritis (for example, rheumatoid arthritis), various cancers, or arteriosclerosis.

Preferable examples of the diseases are kidney diseases (for example, kidney fibrosis, nephritis, renal failure, etc.), lung diseases (for example, pulmonary fibrosis, pneumonia, etc.), skin diseases (for example, psoriasis, scleroderma, atopy, keloid, etc.), liver diseases (for example, hepatic fibrosis, hepatitis, cirrhosis, etc.).

More preferable are kidney diseases (for example, kidney fibrosis, nephritis, renal failure, etc.).

The pharmaceutical composition of the present invention includes the pharmaceutical composition comprising a "CTGF inhibitor," a "CTGF production inhibitor" or a "substance with the activity to inhibit the CTGF-stimulated proliferation of the cells having the capability of proliferating by CTGF stimulation."

Each of the "CTGF inhibitor," the "CTGF production inhibitor," and the "substance" means a substance having the activity of suppressing or inhibiting the biological function of CTGF, or a substance having the activity of suppressing or inhibiting the production of CTGF in a variety of cells. Such substances are exemplified by a substance having any of the following activities:

(1) the activity of suppressing or inhibiting the binding of human kidney-derived fibroblast cells (for example, cell line 293-T (ATCC CRL1573)) to human CTGF, or the binding of the cells to mouse CTGF;

(2) the activity of suppressing or inhibiting the binding of human CTGF with rat kidney-derived fibroblast cells (for example, cell line NRK-49F (ATCC CRL-1570)), human osteosarcoma cell line MG-63 (ATCC CRL-1427), or human lung-derived fibroblast cells;

(3) the activity of suppressing or inhibiting the proliferation of rat kidney-derived fibroblast cells (for example, cell line NRK-49F (ATCC CRL-1570)) in response to the stimulation of human CTGF or mouse CTGF;

(4) the activity of suppressing or inhibiting an increase of hydroxyproline in the kidney where the synthesis of hydroxyproline level tends to be increased.

Specifically, the above-mentioned "substance" is exemplified by the following substances:

(a) the above-mentioned monoclonal antibody of the present invention (which is not restricted to the wild-type antibody and the recombinant antibody) or a portion thereof;

(b) antisense DNA;

(c) antisense RNA;

(d) low molecular weight chemical substances (chemically synthesized compounds or naturally-occurring substances) other than the substances indicated in (a) to (c).

The antisense DNA as referred to in the present invention includes a DNA comprising a partial nucleotide sequence of a DNA encoding the mammalian (preferably human) CTGF protein or a DNA corresponding to the above DNA that is chemically modified in part, or a DNA comprising a complementary sequence to the partial nucleotide sequence, or a DNA corresponding to this DNA that is chemically modified in part.

The "partial nucleotide sequence" as referred to here indicates a partial nucleotide sequence comprising an arbitrary number of nucleotides contained in an arbitrary region of the DNA sequence encoding the mammalian (preferably human) CTGF protein.

The DNA, hybridizing to a DNA or an RNA encoding the CTGF protein, can inhibit the CTGF production by suppressing transcription of the DNA to mRNA or suppressing the translation of the mRNA into the protein.

The partial nucleotide sequence consists of 5 to 100 consecutive nucleotides, preferably 5 to 70 consecutive nucleotides, more preferably 5 to 50 consecutive nucleotides, and still more preferably 5 to 30 consecutive nucleotides.

When the DNA is used as an antisense DNA pharmaceutical, the DNA sequence can be modified chemically in part for extending the half-life (stability) of the blood concentration of the DNA administered to patients, for increasing the intracytoplasmic-membrane permeability of the DNA, or for increasing the degradation resistance or the absorption of the orally administered DNA in the digestive organs. The chemical modification includes, for example, the modification of the phosphate bonds, the riboses, the nucleotide bases, the sugar moiety, the 3' end and/or the 5' end in the structure of the oligonucleotide DNA.

The modification of phosphate bond includes, for example, the conversion of one or more of the bonds to phosphodiester bonds (D-oligo), phosphorothioate bonds, phosphorodithioate bonds (S-oligo), methyl phosphonate (MP-oligo), phosphoroamidate bonds, non-phosphate bonds or methyl phosphonothioate bonds, or combinations thereof. The modification of the ribose includes, for example, the conversion to 2'-fluororibose or 2'-O-methylribose. The modification of the nucleotide base includes, for example, the conversion to 5-propynyluracil or 2-aminoadenine.

The antisense RNA as referred to in the present invention includes an RNA comprising a partial nucleotide sequence of an RNA encoding mammalian (preferably human) CTGF protein or an RNA corresponding to the RNA which is chemically modified in part, or an RNA comprising a complementary sequence to the partial nucleotide sequence or an RNA corresponding to this RNA which is chemically modified in part.

The "partial nucleotide sequence" as referred to here indicates a partial nucleotide sequence comprising an arbitrary number of nucleotides contained in an arbitrary region of the RNA sequence encoding mammalian (preferably human) CTGF protein.

The RNA, hybridizing to a DNA or an RNA encoding the CTGF protein, can inhibit the CTGF production by inhibiting the transcription of the DNA to mRNA or inhibiting the translation of the mRNA into the protein.

The partial nucleotide sequence consists of 5 to 100 consecutive nucleotides, preferably 5 to 70 consecutive nucleotides, more preferably 5 to 50 consecutive nucleotides, and still more preferably 5 to 30 consecutive nucleotides.

When the RNA is used as an antisense RNA pharmaceutical, the RNA sequence can be modified chemically in part for extending the half-life (stability) of the blood concentration of the RNA administered to patients, for increasing the intracytoplasmic-membrane permeability of the RNA, or for increasing the degradation resistance or the absorption of the orally administered RNA in the digestive organ. The chemical modification includes, for example, the modification of the phosphate bonds, the riboses, the nucleotide bases, the sugar moiety, the 3' end and/or the 5' end in the structure of the oligonucleotide RNA.

The modification of phosphate bonds includes, for example, the conversion of one or more of the bonds to phosphodiester bonds (D-oligo), phosphorothioate bond, phosphorodithioate bonds (S-oligo), methyl phosphonate (MP-oligo), phosphoroamidate bonds, non-phosphate bonds or methyl phosphonothioate bonds, or combinations thereof. The modification of the ribose includes, for example, the conversion to 2'-fluororibose or 2'-O-methylribose. The modification of the nucleotide base includes, for example, the conversion to 5-propynyluracil or 2-aminoadenine.

The therapeutic effects of the pharmaceutical composition of the present invention on various diseases can be examined and evaluated according to a usual method by administering the composition to known animals as disease models.

For example, evaluation of the therapeutic effect on kidney fibrosis, which is a tissue fibrosis as well as a kidney disease, can be performed by a method using a renal failure model mouse (unilateral ureteral obstruction (UUO) model), in which unilateral ureteral ligation obstructs renal blood filtration in the kidney and results in renal failure in the mouse. After administration of the inventive pharmaceutical composition to the mouse, the examination is achieved by measuring the degree of inhibition of an increase of hydroxyproline production, which is an index of the onset of nephritis and kidney fibrosis induced by the renal failure. A decrease in the hydroxyproline concentration indicates the efficacy of the pharmaceutical composition for the treatment of the kidney disease.

By using the model animals described in detail in a previous report ("Preparation of animals as disease models: Testing and experimental methods for the development of new drugs" p. 34–46, 1993, Technological Information Society), the evaluation can be performed for kidney diseases including, for example, minimal change glomerular disease (for example, minimal change nephrotic syndrome (MCNS)), focal glomerular sclerosis (FGS), membraneous glomerulonephritis (membranous nephropathy (MN)), IgA nephropathy, mesangial proliferative glomerulonephritis, acute post-streptococcal glomerulonephritis(APSGN, crescentic (extracapillary) glomerulonephritis, interstitial nephritis, or acute renal failure.

By using the model animals described in detail in the previous report ("Preparation of animals as disease models: Testing and experimental methods for the development of new drugs" p. 229–235, 1993, Technological Information Society), the evaluation can be performed for skin diseases including, for example, injuries, keloid, atopy, dermatitis, scleroderma or psoriasis.

By using the model animals described in detail in the previous report ("Preparation of animals as disease models: Testing and experimental methods for the development of new drugs" p. 349–358, 1993, Technological Information Society), the evaluation can be performed for liver diseases including, for example, hepatitis (for example, viral hepatitis (type A, type B, type C, type E, etc.)), cirrhosis or drug induced hepatic injuries.

For example, the effect on arteriosclerosis and restenosis can be evaluated by using a restenosis model rat, in which the pseudo-restenosis is caused by percutaneous transluminal coronary angioplasty(PTCA) with balloon catheter inserted in the aorta.

For example, the effect on tumor growth and metastasis can be confirmed by using mice as cancer metastasis models. The model mice are prepared by transplanting cancer cells into the subcutaneous tissue, caudal vein, spleen, tissues under the renicapsule, peritoneal cavity or cecum wall tissue, of commercially available mice including normal mice such as Balb/c mouse, or model mice such as nude mouse and SCID mouse.

The "rat CTGF" of the present invention (specifically, having an amino acid sequence of, or substantially equivalent to that of SEQ ID NO: 2) and the "DNA encoding rat CTGF" (specifically, comprising the nucleotide sequence spanning from nucleotide position 213 to 1256 of the nucleotide sequence of SEQ ID NO: 1) are defined below, and can be prepared according to a usual method as shown below.

Here, the terminology "substantially equivalent" has the meaning defined above.

The "rat CTGF" of the present invention can be produced by suitably using a method known in this technical field, such as chemical synthesis and cell culture as well as the recombinant technique described below, or by using a modified method thereof.

The "DNA" of the present invention indicates the DNA encoding rat CTGF, and includes any nucleotide sequences as long as the nucleotide sequence encodes rat CTGF of the present invention. Specifically, the DNA includes any DNAs encoding the polypeptide with the amino acid sequence of SEQ ID NO:2. In a preferred embodiment, the DNA comprises the nucleotide sequence spanning from nucleotide position 213 to 1256 in the nucleotide sequence of SEQ ID NO: 1 (for example, the DNA having the nucleotide sequence of SEQ ID NO: 1).

The DNA of the present invention includes both cDNA and genomic DNA encoding rat CTGF.

The DNA of the present invention also includes the DNAs consisting of any codons as long as the codons encodeidentical amino acids.

The DNA of the present invention can be a DNA obtained by any method. For example, the DNA includes complementary DNA (cDNA) prepared from mRNA, DNA prepared from genomic DNA, DNA prepared by chemical synthesis, DNA obtained by PCR amplification with RNA or DNA as a template, and DNA constructed by appropriately combining these methods.

The DNA encoding the rat CTGF of the present invention can be prepared by the usual methods: cloning cDNA from MRNA encoding rat CTGF, isolating genomic DNA and splicing it, PCR using the cDNA or mRNA sequence as a template, chemical synthesis, and so on.

The DNA encoding the rat CTGF can be prepared by cleaving (digesting) each DNA encoding the rat CTGF as prepared above with an appropriate restriction enzyme, and linking the obtained DNA fragments, in combination with linker DNA or Tag if necessary, using an appropriate DNA polymerase and such.

cDNA encoding rat CTGF (hereinafter referred to as the desired protein) can be cloned from mRNA by, for example, the method described below.

First, the mRNA encoding the desired protein is prepared from tissues or cells (for example, rat fibroblasts, etc.) expressing and producing the desired protein. mRNA can be prepared by isolating total RNA by a known method such as quanidine-thiocyanate method (Chirgwin et al., Biochemistry, Vol.18, p5294, 1979), hot phenol method, or AGPC method, and subjecting it to affinity chromatography using oligo-dT cellulose or poly-U Sepharose.

Then, with the MRNA obtained as a template, cDNA is synthesized, for example, by a well-known method using reverse transcriptase, such as the method of Okayama et al (Mol. Cell. Biol. Vol.2, p.161 (1982); ibid. Vol.3, p.280 (1983)) or the method of Hoffman et al. (Gene Vol.25, p.263 (1983)), and converted into double-stranded cDNA. A cDNA library is prepared by transforming *E. coli* with plasmid vectors, phage vectors, or cosmid vectors having this cDNA or by transfecting *E. coli* after in vitro packaging.

The plasmid vectors used in this invention are not limited as long as they are replicated and maintained in hosts. Any phage vector that can be replicated in hosts can also be used. Examples of usually used cloning vectors are pUC19, λgt10, λgt11, and so on. When the vector is applied to immunological screening as mentioned below, a vector having a promoter that can express a gene encoding the desired protein in a host is preferably used.

cDNA can be inserted into a plasmid by, for example, the method of Maniatis et al. (Molecular Cloning, A Laboratory Manual, second edition, Cold Spring Harbor Laboratory, p.1.53, 1989). cDNA can be inserted into a phage vector by, for example, the method of Hyunh et al. (DNA cloning, a practical approach, Vol.1, p.49 (1985)). These methods can be simply performed by using a commercially available cloning kit (for example, a product from Takara Shuzo). The recombinant plasmid or phage vector thus obtained is introduced into an appropriate host cell such as a prokaryote (for example, *E. coli*: HB101, DH5α, Y1090, DH10B, MC1061/P3, etc).

Examples of a method for introducing a plasmid into a host are, calcium chloride method, calcium chloride/rubidium chloride method and electroporation method, described in Molecular Cloning, A Laboratory Manual (second edition, Cold Spring Harbor Laboratory, p.1.74 (1989)). Phage vectors can be introduced into host cells by, for example, a method in which the phage DNAs are introduced into grown hosts after in vitro packaging. In vitro packaging can be easily performed with a commercially available in vitro packaging kit (for example, a product from Stratagene or Amersham).

The cDNA encoding the desired protein can be isolated from the cDNA library so prepared according to the method mentioned above by combining general cDNA screening methods.

For example, a clone comprising the desired cDNA can be screened by a known colony hybridization method (Crunstein et al. Proc. Natl. Acad. Sci. USA, Vol.72, p.3961 (1975)) or plaque hybridization method (Molecular Cloning, A Laboratory Manual, second edition, Cold Spring Harbor Laboratory, p.2.108 (1989)) using $^{32}$P-labeled chemically synthesized oligonucleotides as probes, which correspond to the amino acid sequence of the desired protein. Alternatively, a clone having a DNA fragment encoding a specific region within the desired protein can be screened by amplifying the region by PCR with synthetic PCR primers.

When a cDNA library prepared using a cDNA expression vector (for example, kgt11 phage vector) is used, the desired clone can be screened by the antigen-antibody reaction using an antibody against the desired protein. A screening method using PCR method is preferably used when many clones are subjected to screening.

The nucleotide sequence of the DNA thus obtained can be determined by Maxam-Gilbert method (Maxam et al. Proc. Natl. Acad. Sci. USA, Vol.74, p.560 (1977)) or the dideoxynucleotide synthetic chain termination method using phage M13 (Sanger et al. Proc. Natl. Acad. Sci. USA, Vol.74, pp.5463–5467 (1977)). The whole or a part of the gene encoding the desired protein can be obtained by excising the clone obtained as mentioned above with restriction enzymes and so on.

Also, the DNA encoding the desired protein can be isolated from the genomic DNA derived from the cells expressing the desired protein as mentioned above by the following methods.

Such cells are solubilized preferably by SDS or proteinase K, and the DNAs are deproteinized by repeating phenol extraction. DNAs are digested preferably with ribonuclease. The DNAs obtained are partially digested with appropriate restriction enzymes, and the DNA fragments obtained are amplified with appropriate phage or cosmid to generate a library. Then, clones having the desired sequence are detected, for example, by using radioactively labeled DNA probes, and the whole or a portion of the gene encoding the desired protein is obtained from the clones by excision with restriction enzymes etc.

A DNA encoding a desired protein can be prepared by following standard methods using known mRNA or cDNA of the desired protein as a template by means of PCR (Gene Amplification PCR method, Basics and Novel Development, Kyoritsu Publishers, 1992, etc).

A DNA encoding a desired protein can also be produced by chemical synthesis according to a usual method based on the nucleotide sequence encoding the protein.

The rat CTGF of the present invention can be prepared as a recombinant protein according to the frequently used recombinant technology by using DNA obtained by digesting the rat CTGF-encoding DNA (the cDNA or the genomic DNA comprising introns) prepared by the method indicated above with appropriate restriction enzymes; linking the resulting DNA fragment encoding the rat CTGF, according to need, with a linker DNA or Tag by using an appropriate DNA polymerase or other enzymes.

Specifically, the preparation of the protein is illustrated as follows: the DNA construct as prepared above is inserted into a vector, described below in detail, to obtain an expression vector; a host cell, which will be described hereinafter, is transformed with the expression vector to obtain a transformant; the resulting transformant cells are cultured for the production and accumulation of the desired protein in the culture supernatant; the protein accumulated in the culture supernatant can be purified easily by using column chromatography, etc.

The present invention also relates to an expression vector comprising the DNA encoding the rat CTGF of the present invention. As an expression vector of the present invention, any vector can be used as long as it is capable of retaining replication or self-multiplication in each host cell of prokaryotic and/or eukaryotic cells, including plasmid vectors and phage vectors (Cloning Vectors: A laboratory Manual, Elsevier, N.Y., 1985).

The recombinant vector can easily be prepared by ligating the DNA encoding rat CTGF of the present invention with a vector for recombination available in the art (plasmid DNA and bacteriophage DNA) by the usual method. Specific examples of the vectors for recombination used are *E. coli*-derived plasmids such as pBR322, pBR325, pUC12, pUC13, and pUC19, yeast-derived plasmids such as pSH19 and pSH15, and Bacillus subtilis-derived plasmids such as pUB110, pTP5, and pC194. Examples of phages are a bacteriophages such as λ phage, and an animal or insect virus (pVL1393, Invitrogen) such as a retrovirus, vaccinia virus, and nuclear polyhedrosis virus.

A plasmid vector is useful for expressing the DNA encoding rat CTGF and for producing rat CTGF. The plasmid vector is not limited as long as it expresses the gene encoding the rat CTGF in various prokaryotic and/or eukaryotic host cells and produces this polypeptide. Examples thereof are pMAL C2, pcDNA3.1(−), pEF-BOS (Nucleic Acids Res. Vol.18, p.5322 (1990) and so on), pME18S (Experimental Medicine: SUPPLEMENT, "Handbook of Genetic Engineering" (1992) and so on), etc.

When bacteria, particularly *E. coli* are used as host cells, an expression vector is generally comprised of, at least, a promoter/operator region, an initiation codon, the DNA encoding the protein of the present invention, termination codon, terminator region, and replicon.

When yeast, animal cells, or insect cells are used as hosts, an expression vector is preferably comprised of, at least, a promoter, an initiation codon, the DNA encoding the rat CTGF of the present invention, and a termination codon. It may also comprise the DNA encoding a signal peptide, enhancer sequence, 5'- and 3'-untranslated region of the gene encoding the rat CTGF of the present invention, splicing junctions, polyadenylation site, selectable marker region, and replicon. The expression vector may also contain, if required, a gene for gene amplification (marker) that is usually used.

A promoter/operator region to express the fusion polypeptide of the present invention in bacteria comprises a promoter, an operator, and a Shine-Dalgarno (SD) sequence (for example, AAGG). For example, when the host is Escherichia, it preferably comprises Trp promoter, lac promoter, recA promoter, λPL promoter, 1pp promoter, tac promoter, or the like.

Examples of a promoter to express the rat CTGF of the present invention in yeast are PH05 promoter, PGK promoter, GAP promoter, ADH promoter, and so on. When the host is Bacillus, examples thereof are SL01 promoter, SP02 promoter, penP promoter and so on.

When the host is a eukaryotic cell such as a mammalian cell, examples thereof are SV40-derived promoter, retrovirus promoter, heat shock promoter, and soon, and preferably SV-40 and retrovirus-derived one. As a matter of course, the promoter is not limited to the above examples. In addition, using an enhancer is effective for expression.

A preferable initiation codon is, for example, a methionine codon (ATG).

A commonly used termination codon (for example, TAG, TAA, TGA) is exemplified as a termination codon.

Usually, used natural or synthetic terminators are used as a terminator region.

A replicon means a DNA capable of replicating the whole DNA sequence in host cells, and includes a natural plasmid, an artificially modified plasmid (DNA fragment prepared from a natural plasmid), a synthetic plasmid, and so on. Examples of preferable plasmids are pBR322 or its artificial derivatives (DNA fragment obtained by treating pBR322 with appropriate restriction enzymes) for *E. coli*, yeast 2µ plasmid or yeast chromosomal DNA for yeast, and pRSV-neo ATCC 37198, pSV2dhfr ATCC 37145, pdBPV-MMTneo ATCC 37224, pSV2neo ATCC 37149, pSV2bsr, and such for mammalian cells.

An enhancer sequence, polyadenylation site, and splicing junction that are usually used in the art, such as those derived from SV40 can also be used.

A selectable marker usually employed can be used according to the usual method. Examples thereof are resistance genes for antibiotics, such as tetracycline, ampicillin, or kanamycin.

Examples of genes for gene amplification are dihydrofolate reductase (DHFR) gene, thymidine kinase gene, neomycin resistance gene, glutamate synthase gene, adenosine deaminase gene, ornithine decarboxylase gene, hygromycin-B-phophotransferase gene, aspartate transcarbamylase gene, etc.

The expression vector of the present invention can be prepared by continuously and circularly linking at least the above-mentioned promoter, initiation codon, DNA encoding the protein of the present invention, termination codon, and terminator region, to an appropriate replicon. If desired, appropriate DNA fragments (for example, linkers, restriction sites generated with other restriction enzyme), can be used by the usual method such as digestion with a restriction enzyme or ligation using T4 DNA ligase.

Transformants of the present invention can be prepared by introducing the expression vector mentioned above into host cells.

Host cells used in the present invention are not limited as long as they are compatible with an expression vector mentioned above and can be transformed. Examples thereof are various cells such as wild-type cells or artificially established recombinant cells usually used in technical field of the present invention (for example, bacteria (Escherichia and Bacillus), yeast (Saccharomyces, Pichia, and such), animal cells, or insect cells).

*E. coli* or animal cells are preferably used. Specific examples are *E. coli* (DH5 α, DH10B, TB1, HB101, XL-2Blue, and such), mouse-derived cells (COP, L, C127, Sp2/0, NS-1, NIH 3T3, and such), rat-derived cells, hamster-derived cells (BHK, CHO, and such), monkey-derived cells (COS1, COS3, COS7, CV1, Velo, and such), and human-derived cells (Hela, diploid fibroblast-derived cells, myeloma, Namalwa, and such).

An expression vector can be introduced (transformed (transduced)) into host cells by known methods.

Transformation can be performed, for example, according to the method of Cohen et al. (Proc. Natl. Acad. Sci. USA, Vol.69, p.2110 (1972)), protoplast method (Mol. Gen. Genet., Vol.168, p.111 (1979)), or competent method (J. Mol. Biol., Vol.56, p.209 (1971)) when the hosts are bacteria (*E. coli, Bacillus subtilis*, and such), the method of Hinnen et al. (Proc. Natl. Acad. Sci. USA, Vol.75, p.1927 (1978)), or lithium method (J. Bacteriol., Vol.153, p.163 (1983)) when the host is Saccharomyces cerevisiae, the method of Graham (Virology, Vol.52, p.456 (1973)) when the hosts are animal cells, and the method of Summers et al. (Mol. Cell. Biol., Vol.3, pp.2156–2165 (1983)) when the hosts are insect cells.

Rat CTGF of the present invention can be produced by cultivating transformants (in the following this term includes transductants) comprising an expression vector prepared as mentioned above in nutrient media.

The nutrient media preferably comprise carbon source, inorganic nitrogen source, or organic nitrogen source necessary for the growth of host cells (transformants). Examples of the carbon source are glucose, dextran, soluble starch, and sucrose, and examples of the inorganic or organic nitrogen source are ammonium salts, nitrates, amino acids, corn steep liquor, peptone, casein, meet extract, soy bean cake, and potato extract. If desired, they may comprise other nutrients (for example, an inorganic salt (for example, calcium chloride, sodium dihydrogenphosphate, and magnesium chloride), vitamins, antibiotics (for example, tetracycline, neomycin, ampicillin, kanamycin, and so on).

Cultivation is performed by a method known in the art. Cultivation conditions such as temperature, pH of the media, and cultivation time are selected appropriately so that the protein of the present invention is produced in large quantities.

Specific media and cultivation conditions used depending on host cells are illustrated below, but are not limited thereto.

When the hosts are bacteria, actinomycetes, yeasts, filamentous fungi, liquid media comprising the nutrient source mentioned above are appropriate. The media with pH 5 to 8 are preferably used. When the host is E. coli, examples of preferable media are LB media, M9media (Milleretal. Exp. Mol. Genet., Cold Spring Harbor Laboratory, p.431 (1972)), YT medium, and so on. Using these media, cultivation can be performed usually at 14 to 43° C. for about 3 to 24 hours with aeration and stirring, if necessary.

When the host is Bacillus, cultivation can be performed usually at 30 to 40° C. for about 16 to 96 hours with aeration and stirring, if necessary.

When the host is yeast, an example of media is Burkholder minimal media (Bostian, Proc. Natl. Acad. Sci. USA, Vol.77, p.4505 (1980)). The pH of the media is preferably 5 to 8. Cultivation can be performed usually at 20 to 35° C. for about 14 to 144 hours with aeration and stirring, if necessary.

When the host is an animal cell, examples of media are MEM media containing about 5 to 20% fetal bovine serum (Science, Vol.122, p.501 (1952)), DMEM media (Virology, Vol.8, p.396 (1959)), RPMI1640 media (J. Am. Med. Assoc., Vol.199, p.519 (1967)), 199 media (Proc. Soc. Exp. Biol. Med., Vol.73, p.1 (1950)), HamF12 media, and so on. The pH of the media is preferably about 6 to 8. Cultivation can be performed usually at about 30 to 40° C. for about 15 to 72 hours with aeration and stirring, if necessary.

When the host is an insect cell, an example of media is Grace's media containing fetal bovine serum (Proc. Natl. Acad. Sci. USA, Vol.82, p.8404 (1985)). The pH thereof is preferably about 5 to 8. Cultivation can be performed usually at about 20 to 40° C. for 15 to 100 hours with aeration and stirring, if necessary.

Rat CTGF of the present invention can be produced by cultivating transformants as mentioned above (in particular animal cells or E. coli) and allowing them to secrete the protein into the culture supernatant. Namely, a culture filtrate (supernatant) is obtained by a method such as filtration or centrifugation of the obtained culture, and the rat CTGF of the present invention is purified and isolated from the culture filtrate by methods commonly used in order to purify and isolate a natural or synthetic protein.

Examples of the isolation and purification method are a method utilizing affinity, such as affinity column chromatography; a method utilizing solubility, such as salting out and solvent precipitation method; a method utilizing the difference in molecular weight, such as dialysis, ultrafiltration, gel filtration, and sodium dodecyl sulfate-polyacrylamide gel electrophoresis; a method utilizing charges, such as ion exchange chromatography and hydroxylapatite chromatography; a method utilizing the difference in hydrophobicity, such as reverse phase high performance liquid chromatography; and a method utilizing the difference in isoelectric point, such as isoelectric focusing.

When the rat CTGF of the present invention exists in the periplasm or cytoplasm of cultured transformants, first, the cells are harvested by a usual method such as filtration or centrifugation and suspended in appropriate buffer. After the cell wall and/or cell membrane of the cells and such are disrupted by the method such as lysis with sonication, lysozyme, and freeze-thawing, the membrane fraction comprising the rat CTGF of the present invention is obtained by the method such as centrifugation or filtration. The membrane fraction is solubilized with a detergent such as Triton-X100 to obtain the crude extract. Finally, the protein is isolated and purified from the crude extract by the usual method as illustrated above.

The "transgenic mouse" of the present is a transgenic mouse in which the above human CTGF encoding DNA (cDNA or genomic DNA) prepared by the method mentioned above has been integrated into the endogenous gene locus of the mouse. This transgenic mouse expresses and secretes the human CTGF in vivo.

The transgenic mouse can be prepared according to the method usually used for producing a transgenic animal (for example, see "Newest Manual of Animal Cell Experiment", LIC press, Chapter 7, pp.361–408, (1990)). Specifically, for example, a transgenic mouse can be produced as follows. Embryonic stem cells (ES cells) obtained from normal mouse blastocysts are transformed with an expression vector in which the gene encoding the human CTGF has been inserted in an expressible manner. ES cells in which the gene encoding the human CTGF has been integrated into the endogenous gene are screened by a usual method. Then, the ES cells screened are microinjected into a fertilized egg (blastocyst) obtained from another normal mouse (Proc. Natl. Acad. Sci. USA, Vol.77, No.12, pp.7380–7384 (1980); U.S. Pat. No. 4,873,191). The blastocyst is transplanted into the uterus of another normal mouse as the foster mother and chimeric transgenic mice are born. By mating the chimeric transgenic mice with normal mice, heterozygous transgenic mice are obtained. By mating the heterozygous transgenic mice with each other, homozygous transgenic mice are obtained according to Mendel's laws.

BRIEF DESCRIPTION OF THE DRAWINGS

FIG. 1 shows the properties of various monoclonal antibodies prepared by immunizing a variety of mammals with human CTGF or mouse CTGF.

FIG. 2 shows the properties of various human monoclonal antibodies prepared by immunizing human antibody-producing transgenic mice with human CTGF.

The ordinate indicates the [$^3$H]-thymidine uptake of the cells as an index of the growth promoting activity; the abscissa indicates the concentrations of the respective recombinant CTGFs used.

Figure 5:
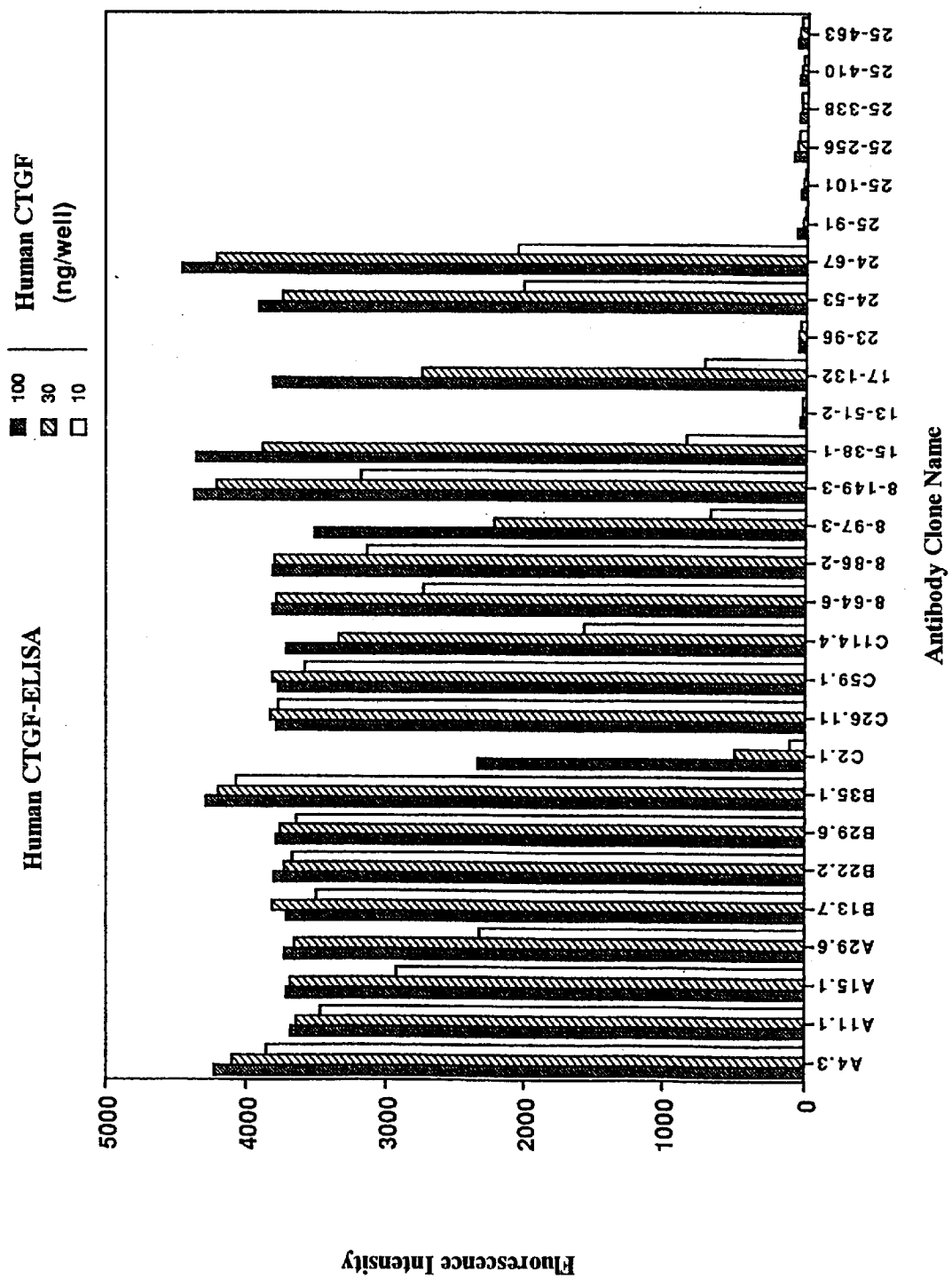

FIG. 5 shows the reactivity of various monoclonal antibodies to human CTGF. The monoclonal antibodies were prepared by immunizing a variety of mammals with human or mouse CTGF.

The ordinate indicates the fluorescence intensity as an index of the reactivity of the monoclonal; the abscissa indicates clone names of the monoclonal antibodies tested by ELISA with different concentrations of the human CTGF.

Figure 6:
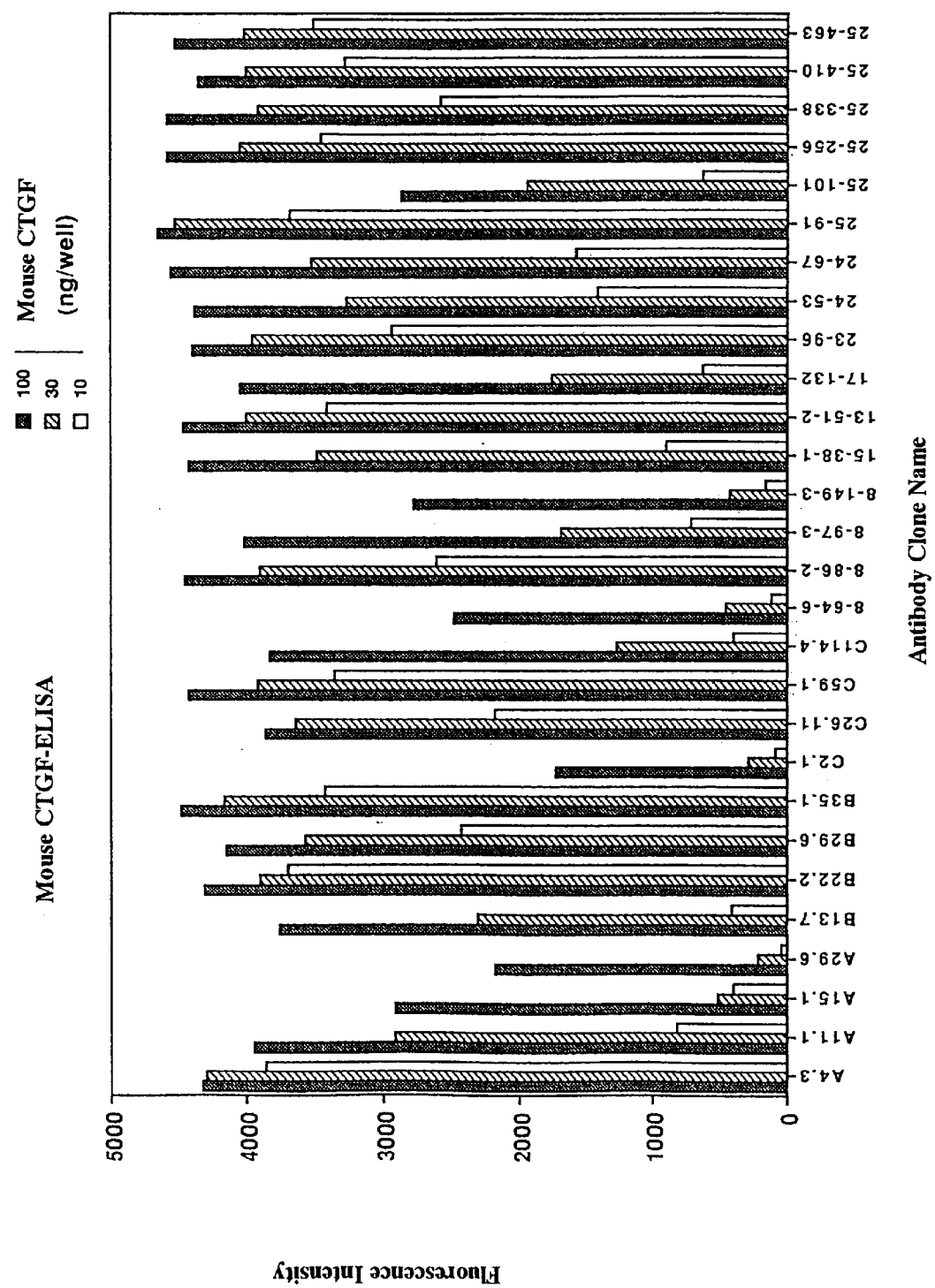

FIG. 6 shows the reactivity of various monoclonal antibodies to the mouse CTGF. The monoclonal antibodies were prepared by immunizing a variety of mammals with human or mouse CTGF.

The ordinate indicates the fluorescence intensity as an index of the reactivity of the monoclonal antibody; the abscissa indicates clone names of the monoclonal antibodies tested by ELISA with different concentrations of mouse CTGF.

Figure 7:
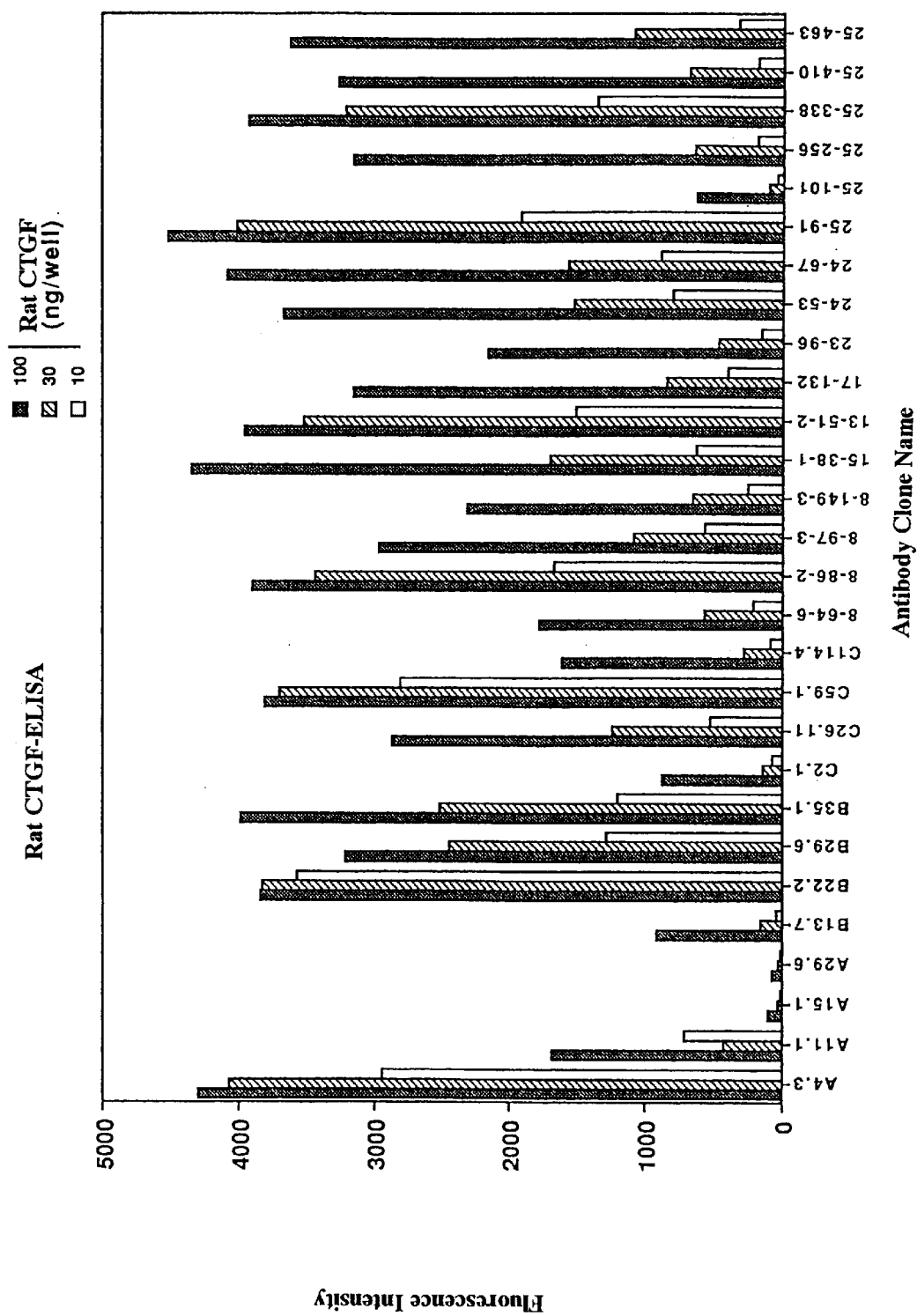

FIG. 7 shows the reactivity of various monoclonal antibodies to rat CTGF. The monoclonal antibodies were prepared by immunizing a variety of mammals with human or mouse CTGF.

The ordinate indicates the fluorescence intensity as an index of the reactivity of the monoclonal antibody; the abscissa indicates clone names of the monoclonal antibodies tested by ELISA with different concentrations of rat CTGF.

Figure 8:
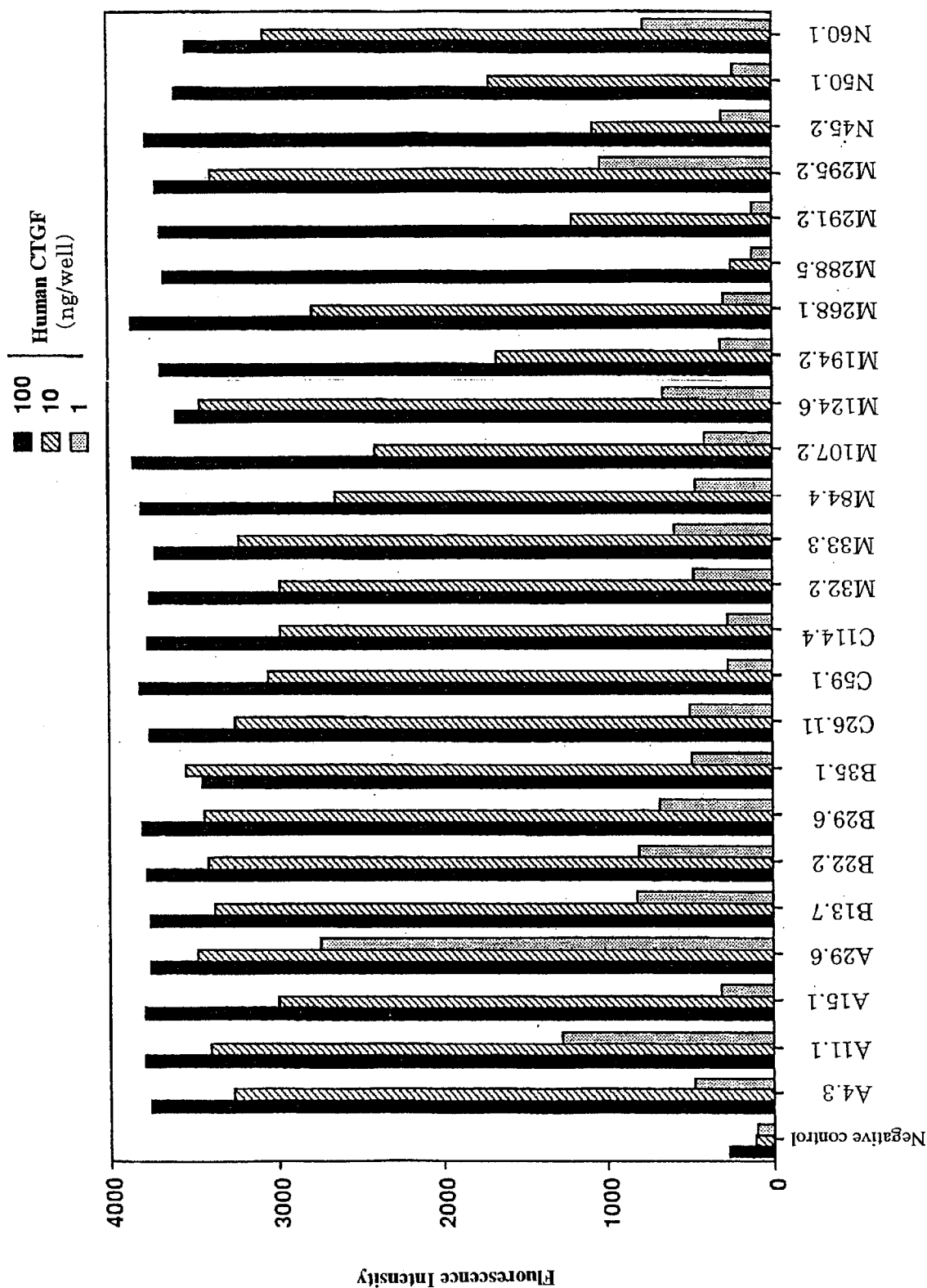

FIG. 8 shows the reactivity of various human monoclonal antibodies to human CTGF. The antibodies were prepared by immunizing the human antibody-producing transgenic mice with human CTGF.

The ordinate indicates the fluorescence intensity as an index of the reactivity of the monoclonal antibody; the abscissa indicates clone names of the human monoclonal antibodies tested by ELISA with different concentrations of human CTGF.

Figure 9:
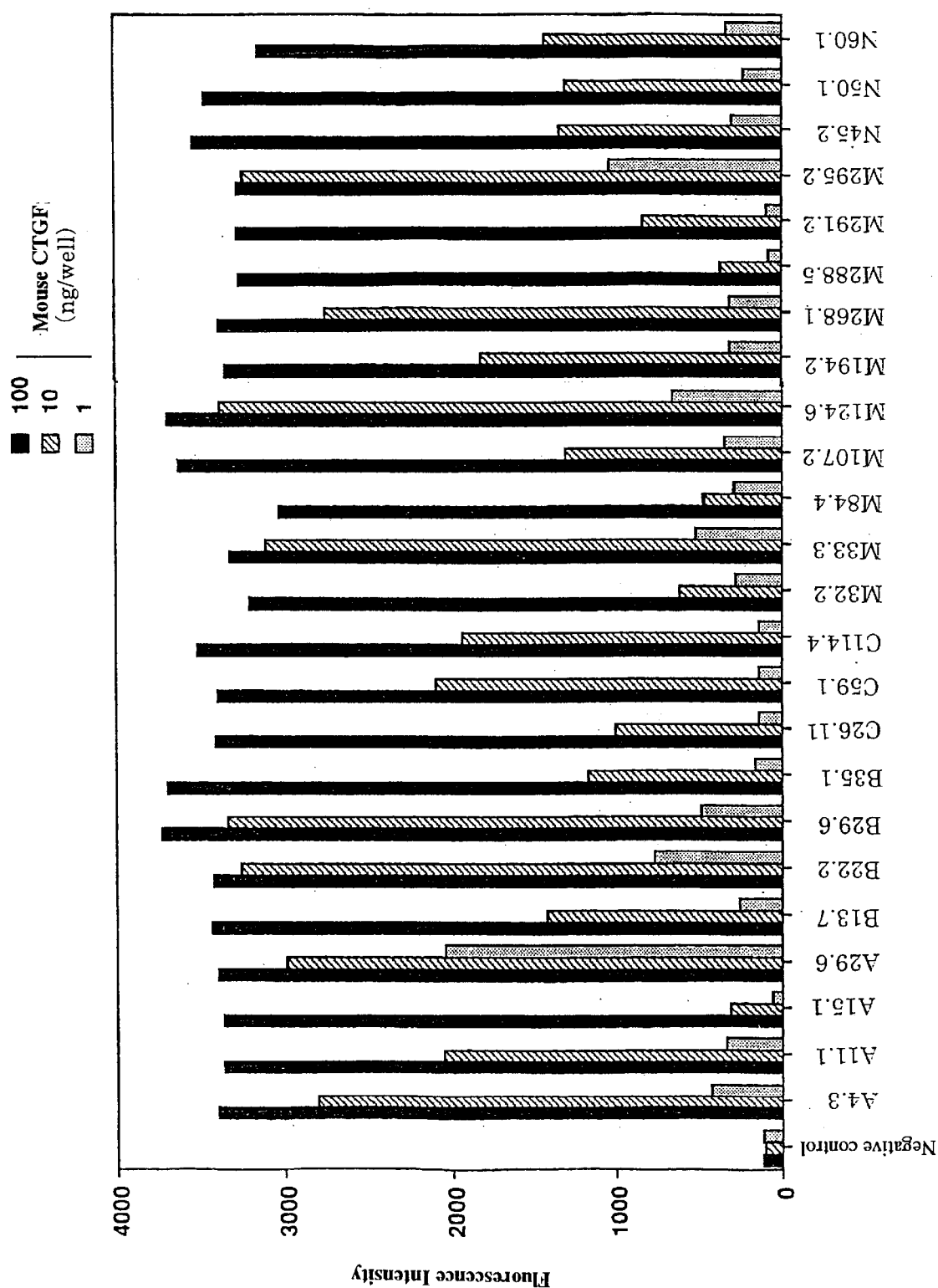

FIG. 9 shows the reactivity of various human monoclonal antibodies to mouse CTGF. The antibodies were prepared by immunizing the human antibody-producing transgenic mice with human CTGF.

The ordinate indicates the fluorescence intensity as an index of the reactivity of the monoclonal antibody; the abscissa indicates clone names of the human monoclonal antibodies tested by ELISA with different concentrations of mouse CTGF.

Figure 10:
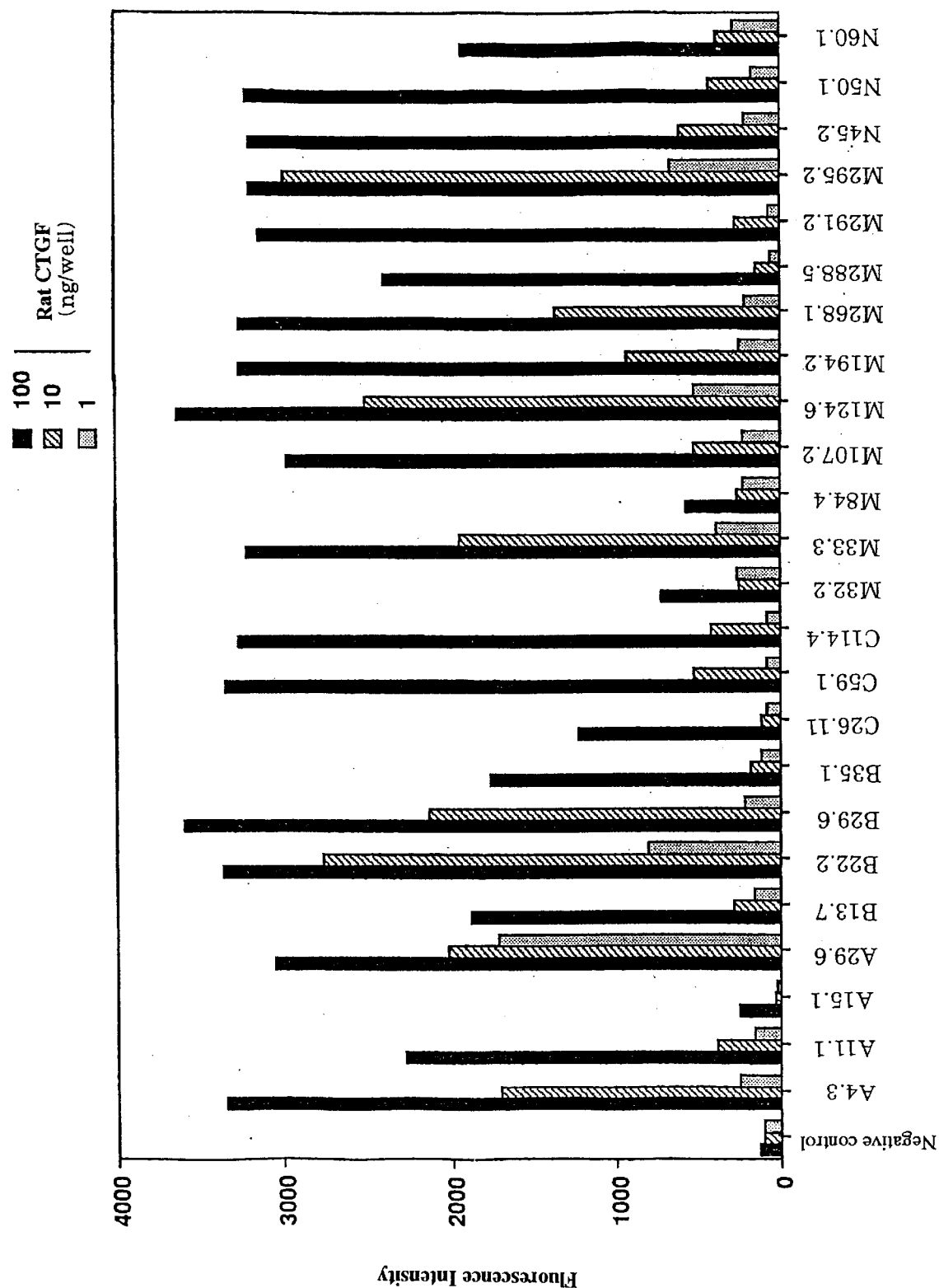

FIG. 10 shows the reactivity of various human monoclonal antibodies to rat CTGF. The antibodies were prepared by immunizing the human antibody-producing transgenic mice with human CTGF.

The ordinate indicates the fluorescence intensity as an index of the reactivity of the monoclonal antibody; the abscissa indicates clone names of the human monoclonal antibodies tested by ELISA with different concentrations of rat CTGF.

Figure 11:
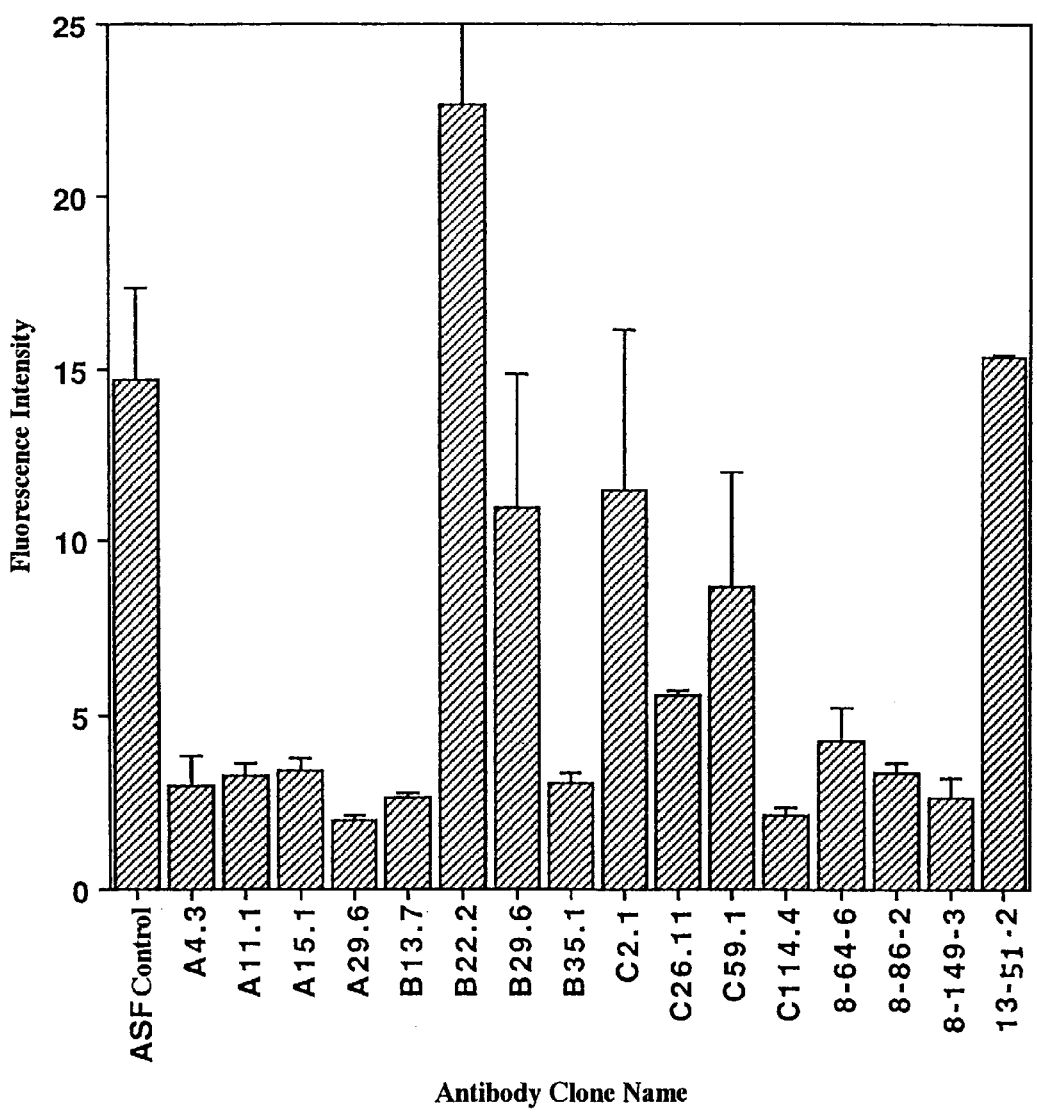

FIG. 11 shows the inhibiting activity of various monoclonal antibodies for the binding of human or mouse CTGF to the human kidney-derived fibroblast cell line 293-T. The monoclonal antibodies were prepared by immunizing a variety of mammals with human or mouse CTGF.

The ordinate indicates that fluorescence intensity as an index of the inhibiting activity; the abscissa indicates clone names of various monoclonal antibodies tested.

Figure 12:
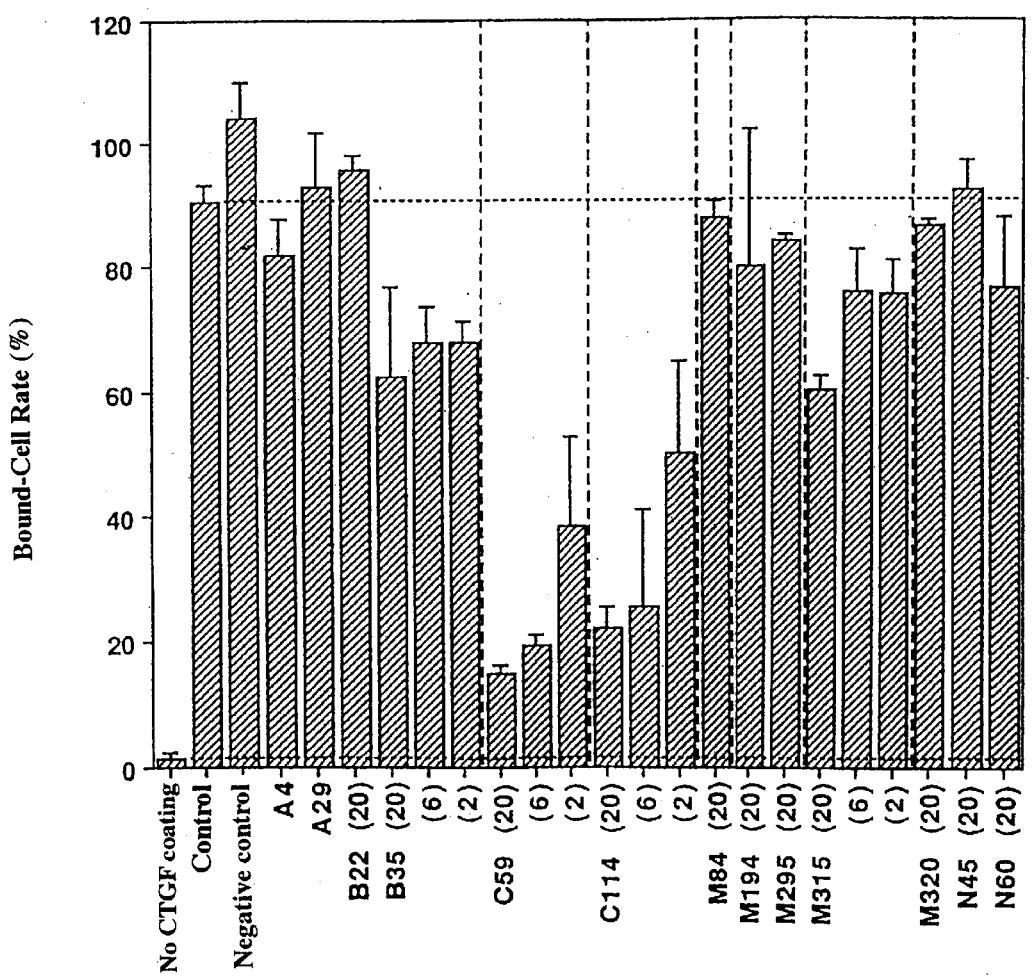

FIG. 12 shows the inhibiting activity of various human monoclonal antibodies for the binding of human CTGF to the rat kidney-derived fibroblast cell line NRK-49F. The antibodies were prepared by immunizing human antibody-producing transgenic mice with human CTGF.

The ordinate indicates the rate of bound cells (%); the abscissa indicates clone names of the various monoclonal antibodies tested. The total number of cells added is taken as 100%.

Figure 13:
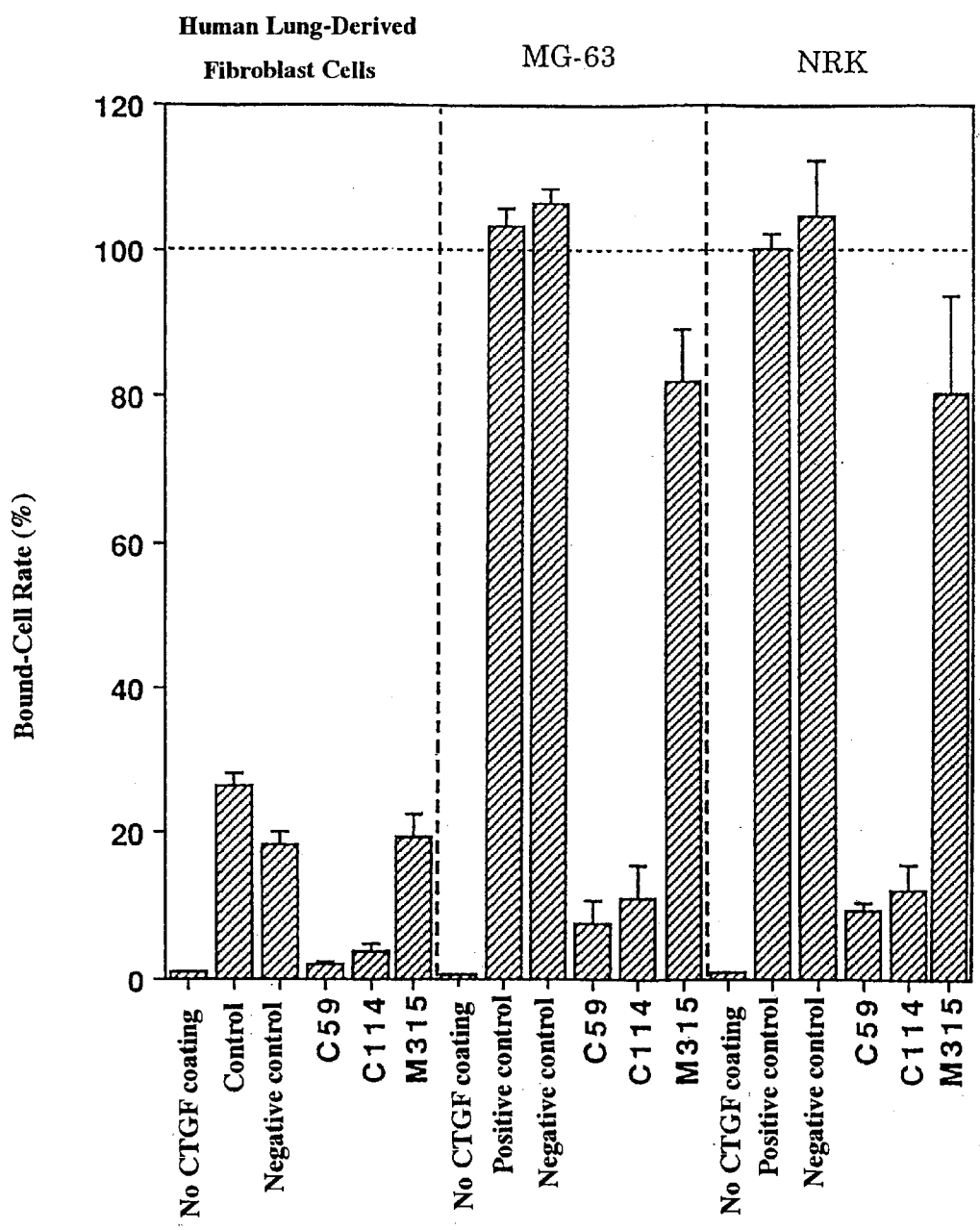

FIG. 13 shows the inhibiting activity of various human monoclonal antibodies for the binding of human CTGF to the rat kidney-derived fibroblast cell line NRK-49F, the human osteosarcoma-derived cell line MG-63, or human lung-derived fibroblast cells. The antibodies were prepared by immunizing the human antibody-producing transgenic mice with human CTGF.

The ordinate indicates the rate of bound cells (%); the abscissa indicates clone names of the various monoclonal antibodies tested. The total number of cells added is taken as 100%.

Figure 14:
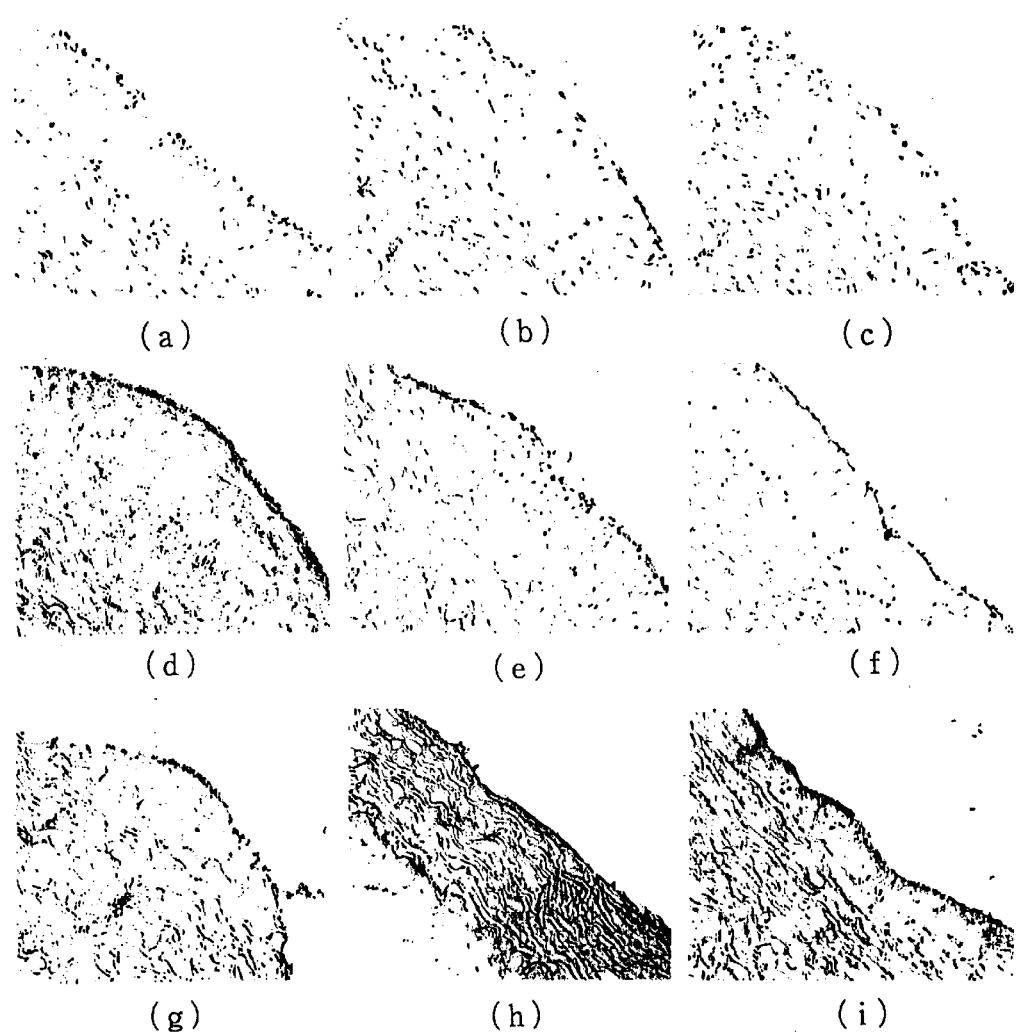

FIG. 14 shows immunological staining patterns of tissue sections from arteriosclerotic lesions of a rabbit as an arteriosclerosis model rabbit. By using various monoclonal antibodies prepared by immunizing a variety of mammals with human or mouse CTGF, the sections were stained and the reactivity of the antibodies to the lesions was assessed.

The panel (a) shows a control stain; (b) shows the stain with the monoclonal antibody B35.1; (c) shows the stain with the monoclonal antibody B29.6; (d) shows the stain with the monoclonal antibody 13-51-2; (e) shows the stain with the monoclonal antibody A4.3; (f) shows the stain with the monoclonal antibody C114.4; (g) shows the stain with the monoclonal antibody A11.1; (h) shows the stain with the monoclonal antibody A29.6; and (1) shows the stain with the monoclonal antibody C26.11.

Figure 15:
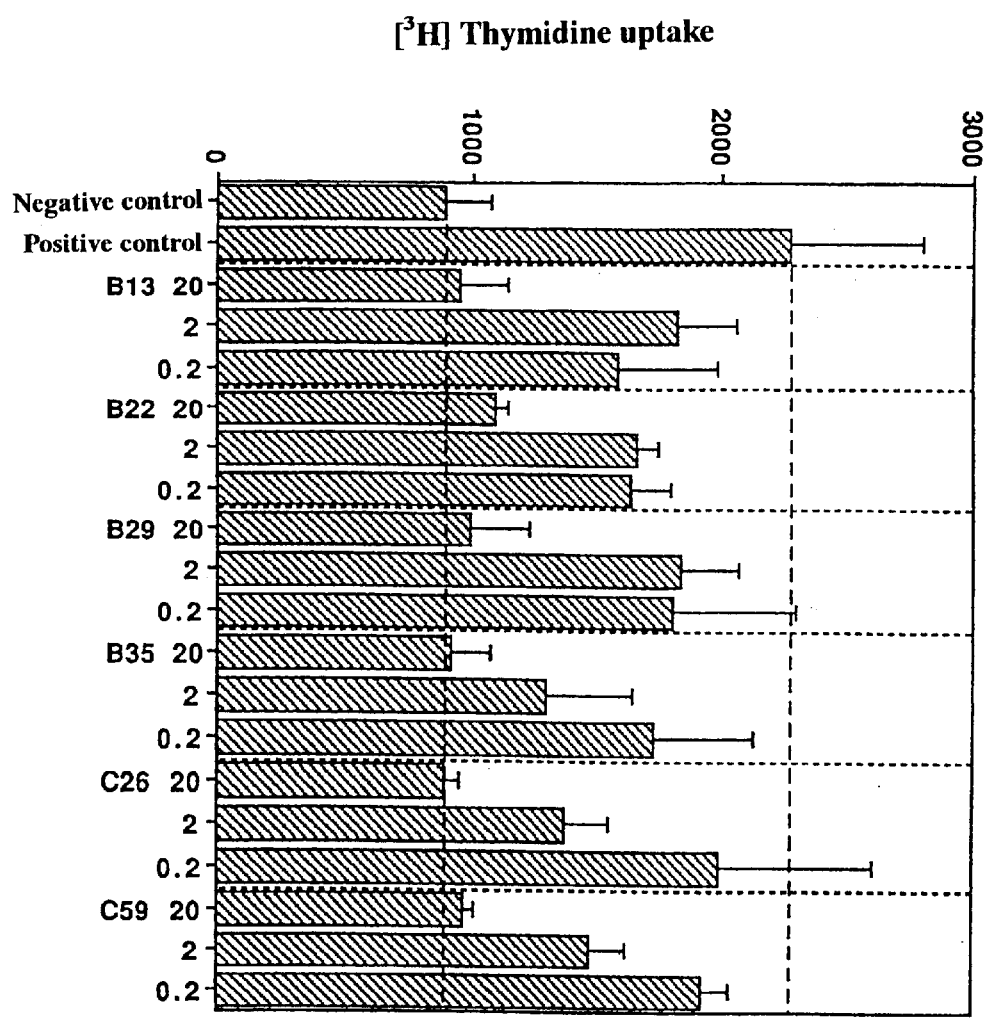

FIG. 15 shows the inhibiting activity of various human monoclonal antibodies towards for the proliferation of the rat kidney-derived fibroblast cells NRK-49F stimulated by the purified human CTGF. The antibodies were prepared by immunizing the human antibody-producing transgenic mice with human CTGF.

The ordinate indicates the [$^3$H]-thymidine uptake of the cells as an index of the growth promoting activity; the abscissa indicates clone names of the human monoclonal antibodies tested by using the purified human CTGF of different concentrations.

Figure 16:
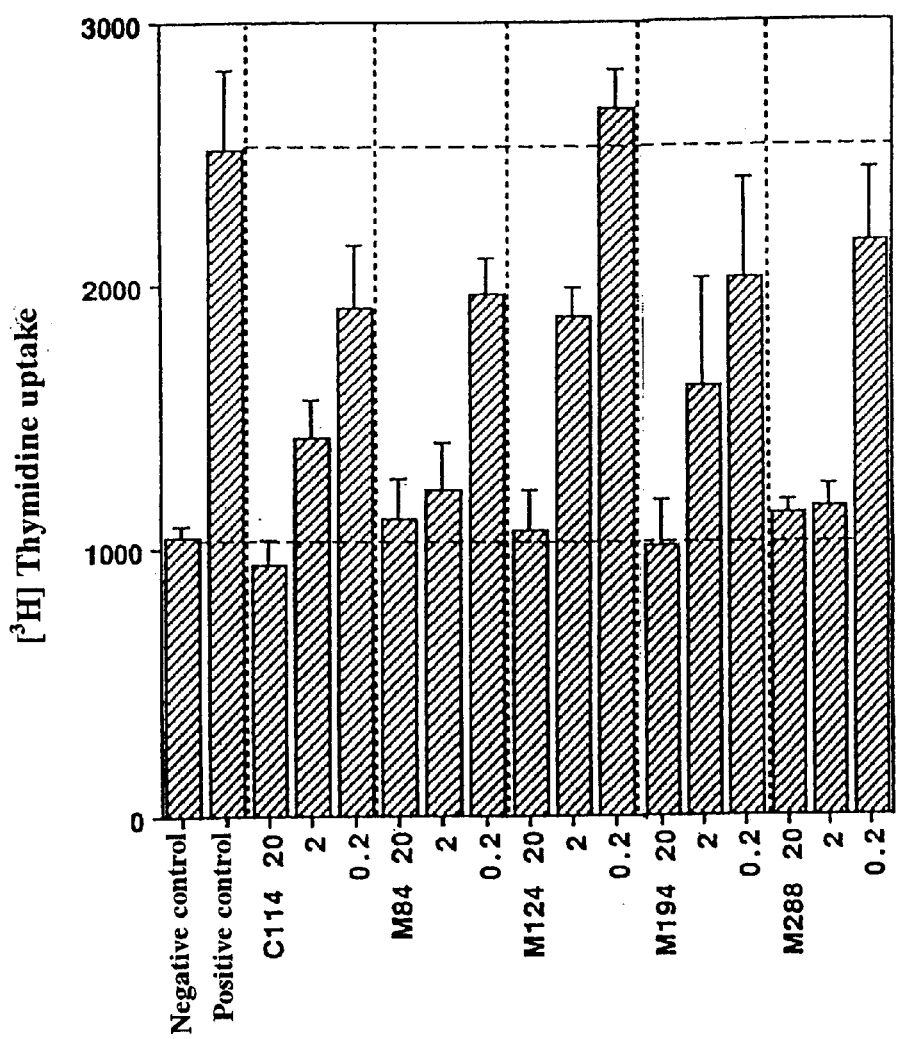

FIG. 16 shows the inhibiting activity of various human monoclonal antibodies towards the proliferation of the rat kidney-derived fibroblast cells NRK-49F stimulated by the purified human CTGF. The antibodies were prepared by immunizing the human antibody-producing transgenic mice with human CTGF.

The ordinate indicates the [$^3$H]-thymidine uptake of the cells as an index of the growth promoting activity; the abscissa indicates clone names of the human monoclonal antibodies tested by using purified human CTGF of different concentrations.

Figure 17:
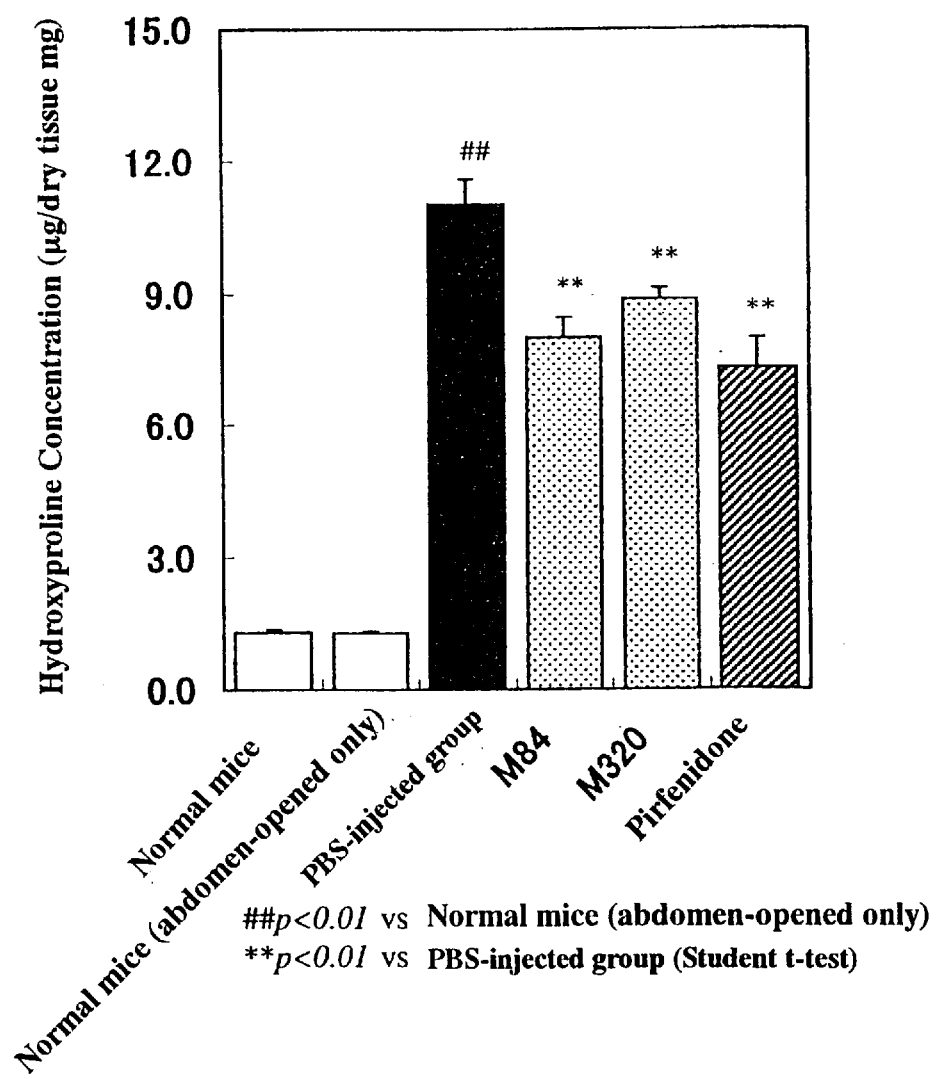

FIG. 17 shows the therapeutic effect of various human monoclonal antibodies on kidney diseases and fibrotic diseases in tissues. The antibodies were prepared by immunizing the human antibody-producing transgenic mice with human CTGF.

The ordinate indicates the concentration of hydroxyproline which is an index of advancement of the disease; the abscissa indicates clone names of the human monoclonal antibodies administered.

Figure 18:
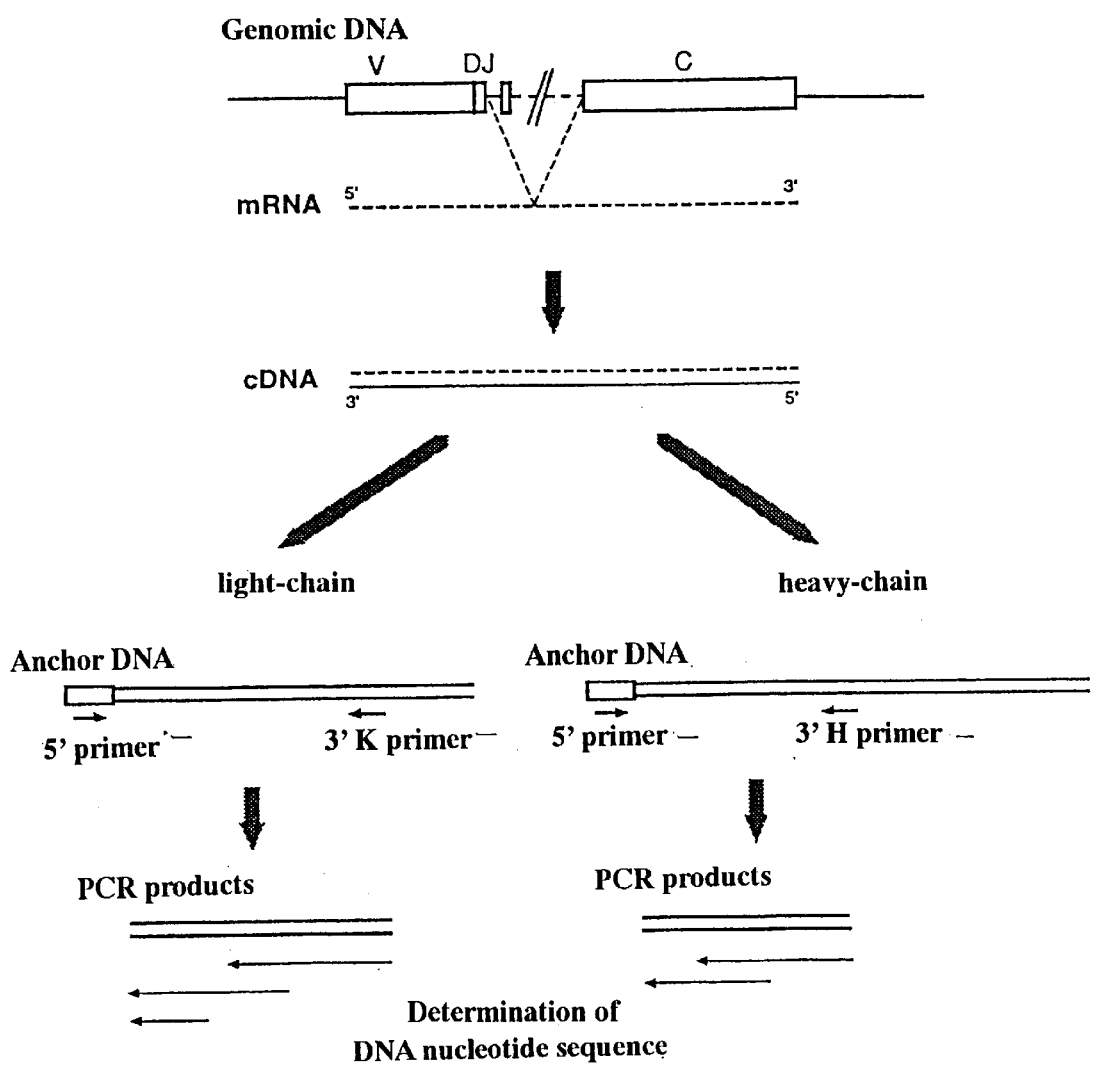

FIG. 18 schematically shows the procedure for the sequence determination of the DNAs encoding the heavy chain and the light chain of the human anti-human CTGF monoclonal antibody.

Figure 19:
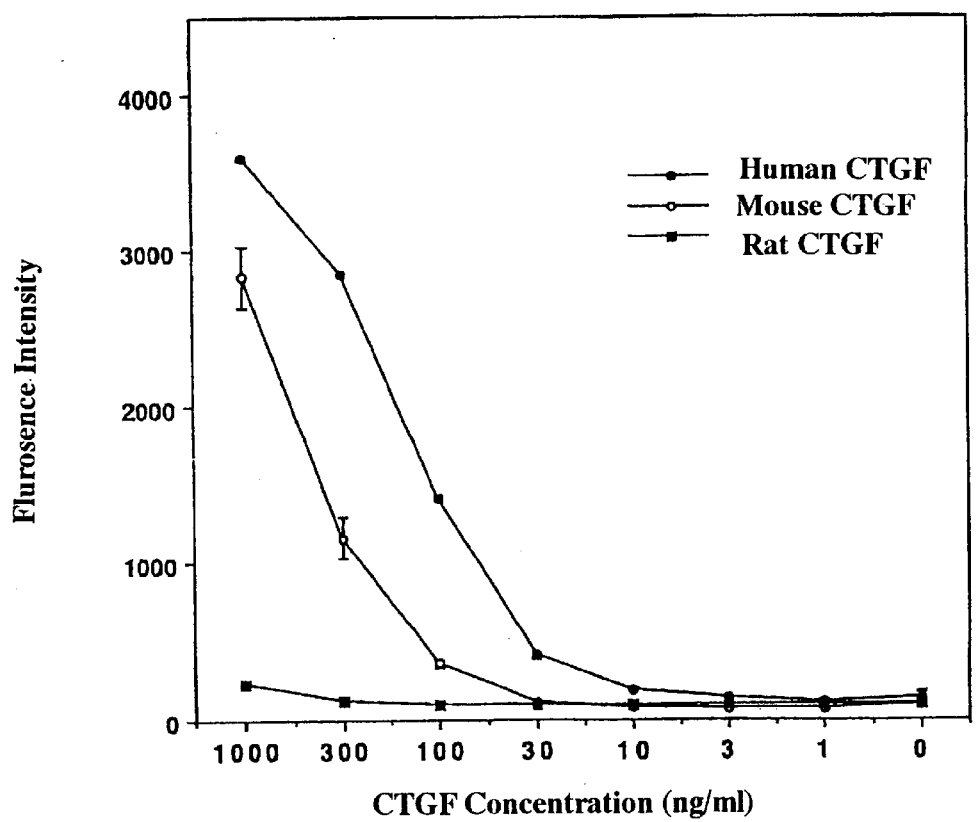

FIG. 19 shows the calibration curves of the human CTGF standard, mouse CTGF standard, and rat CTGF standard. The curves were obtained by sandwich ELISA using the monoclonal antibodies 8-64-6 and 8-86-2.

The ordinate indicates the fluorescence intensity; the abscissa indicates the concentration of the standards of CTGF.

Figure 20:
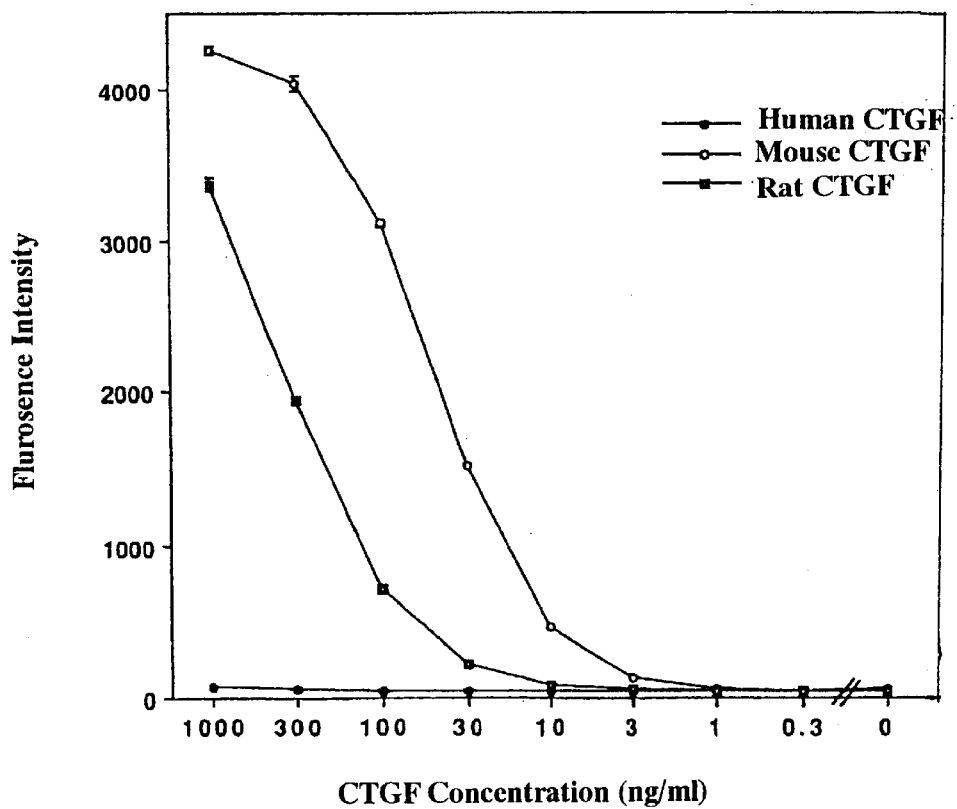

FIG. 20 shows the calibration curves of the human CTGF standard, mouse CTGF standard, and rat CTGF standard. The curves were obtained by sandwich ELISA using the monoclonal antibodies 13-51-2 and 8-86-2.

The ordinate indicates the fluorescence intensity; the abscissa indicates the concentration of the standards of CTGF.

Figure 21:
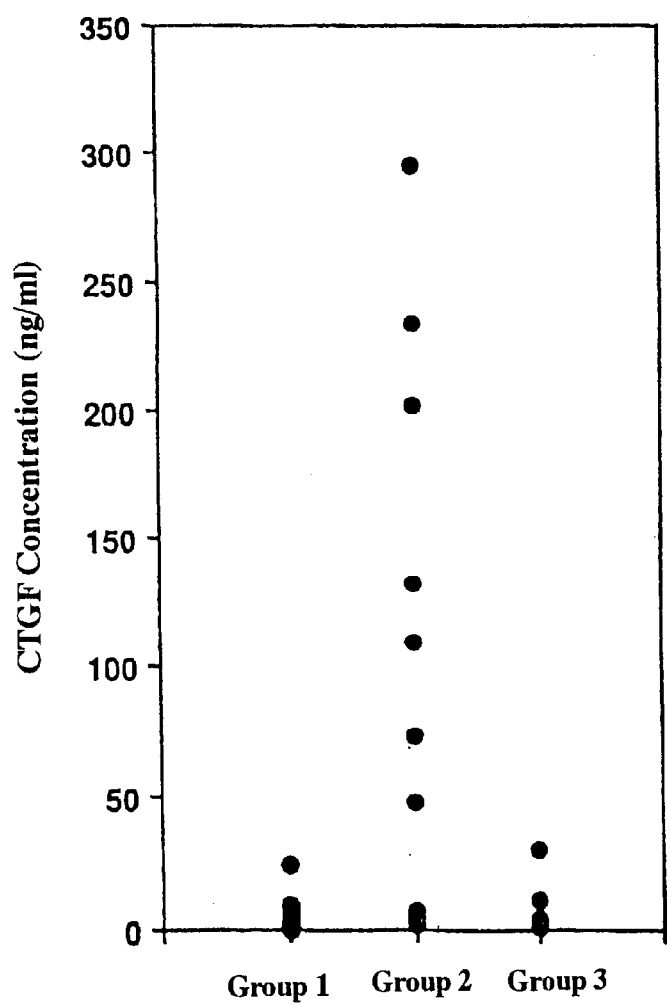

FIG. 21 shows CTGF concentrations in various serum samples from patients affected with biliary atresia. The concentration was determined by sandwich ELISA with the monoclonal antibodies 8-64-6 and 8-86-2.

The ordinate indicates the concentrations (CTGF content) determined; the abscissa indicates the subject groups tested. The samples were obtained from three groups; Group 1 (I) consisting of patients with normal clinical findings; Group 2 (II) consisting of patients with symptoms progressing; and Group 3 (III) consisting of patients with severe symptoms in need of liver transplantation.

Figure 22:
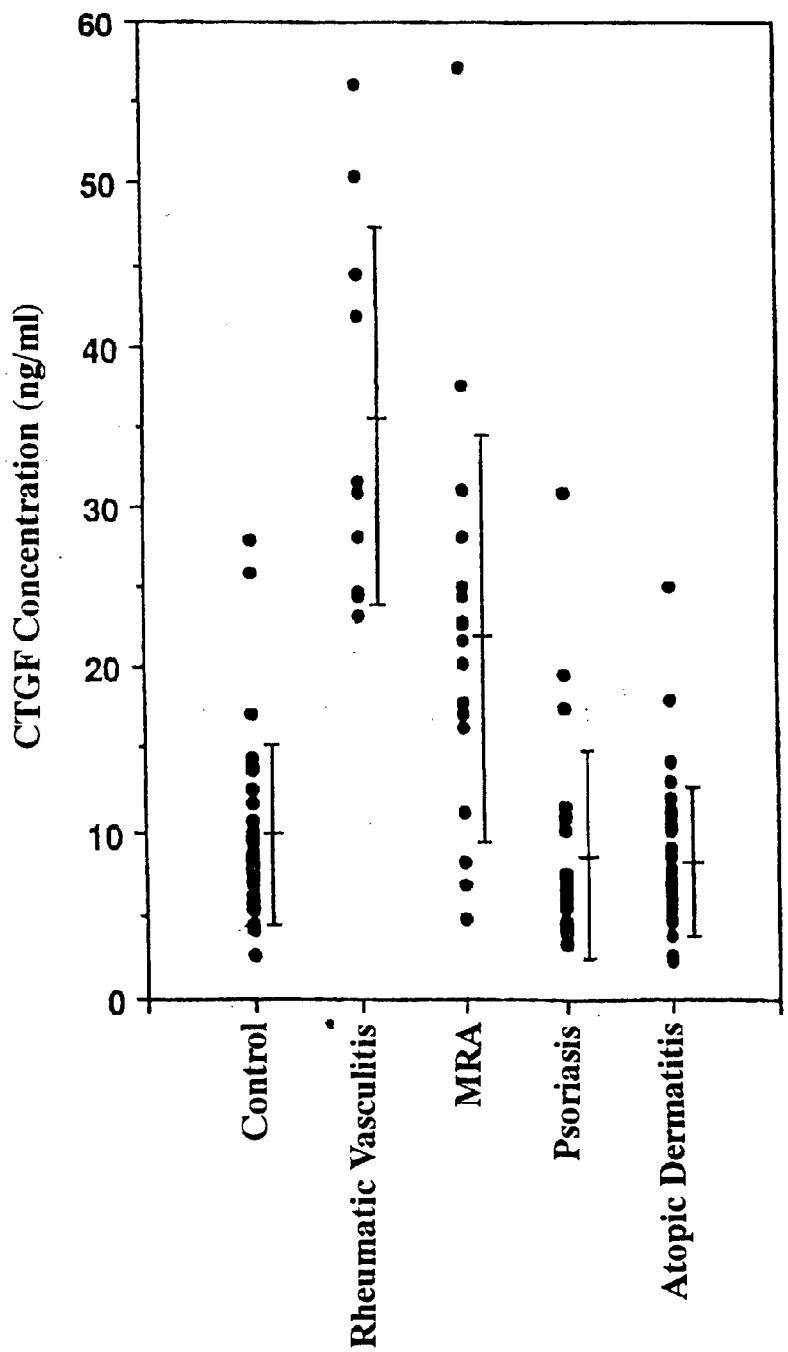

FIG. 22 shows CTGF concentrations in various serum samples from patients affected various diseases. The concentration was determined by sandwich ELISA with the monoclonal antibodies 8-64-6 and 8-86-2.

The ordinate indicates the concentrations (CTGF content) determined; the abscissa indicates the diseases with which the patients affected.

Figure 23:
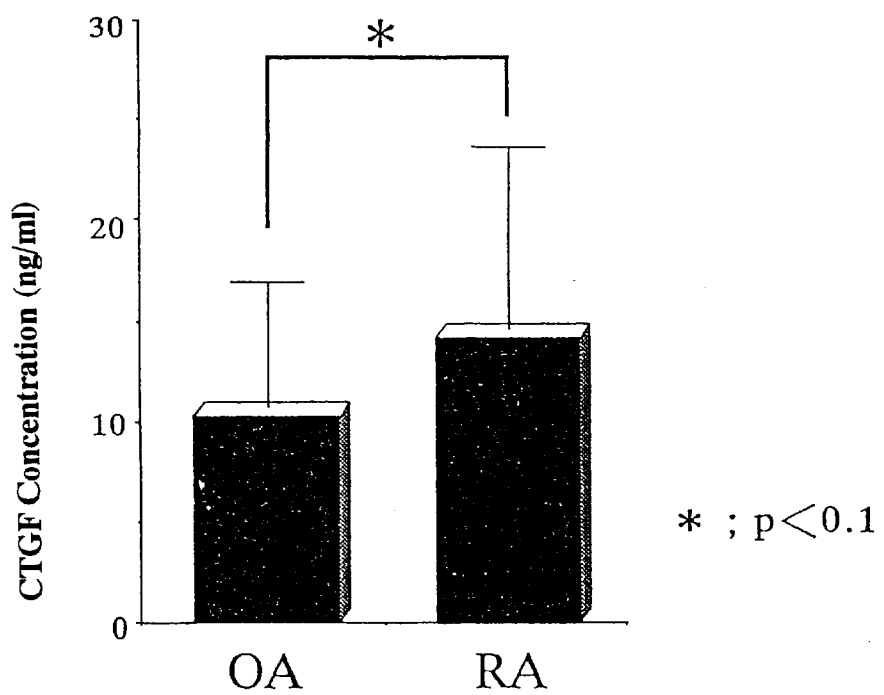

FIG. 23 shows CTGF concentrations in the synovial fluid samples from patients affected with rheumatoid arthritis or osteoarthritis. The concentration was determined by sandwich ELISA with the monoclonal antibodies 8-64-6 and 8-86-2.

The ordinate indicates the concentrations (CTGF content) determined; the abscissa indicates the diseases with which the patients affected.

Figure 24:
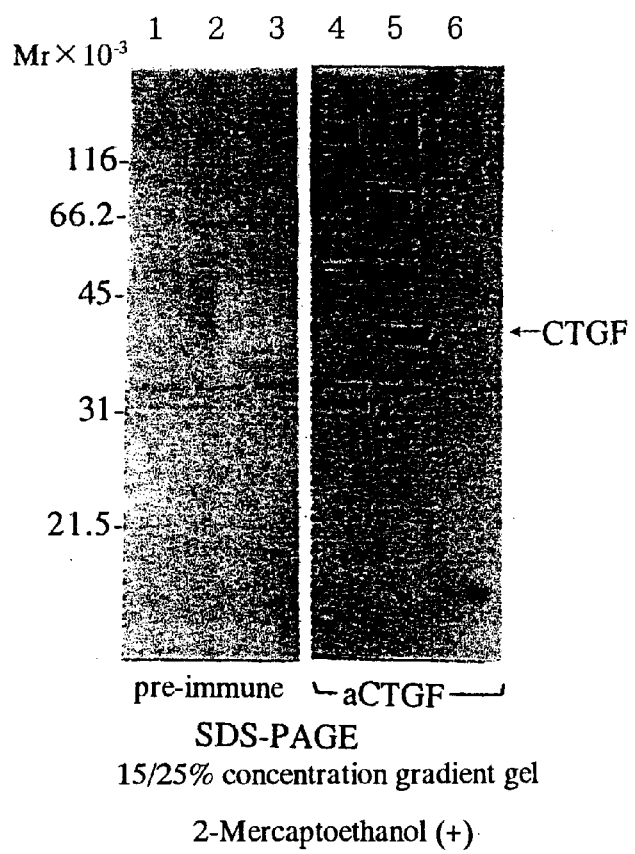

FIG. 24 are SDS-polyacrylamide gel patterns showing the result of Western blotting of human CTGF fractions purified from human fetal 25 skin-derived fibroblast cells by using a heparin column.

Lanes 1, 2, and 3 contain fractions eluted with 0.2 M, 0.6 M, and 2.0M NaCl, respectively, and the samples were treated with pre-immune antibody (pre-immune serum from normal rabbit). Lanes 4, 5, and 6 contain the fractions eluted with 0.2 M, 0.6 M, and 2.0M NaCl, respectively, and the samples were treated with an anti-human CTGF polyclonal antibody.

Figure 25:
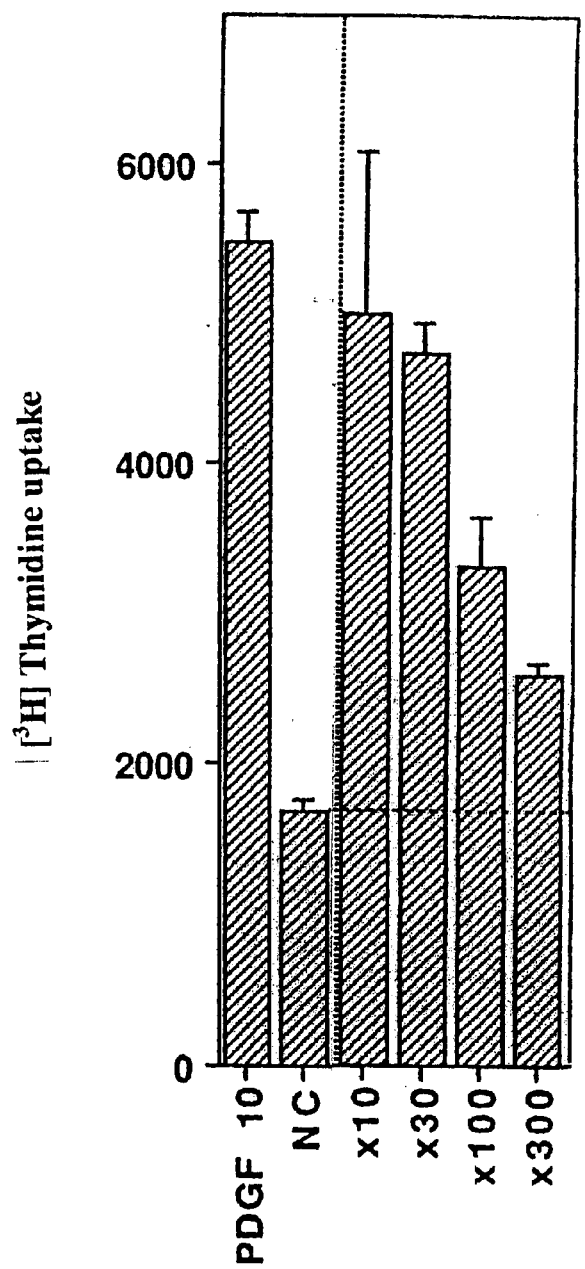

FIG. 25 shows the growth-promoting activity of human CTGF for rat kidney-derived fibroblast cells NRK-49F. The human CTGF is purified from human fetal skin-derived fibroblast cells by using a heparin column. The fraction eluted with 0.6M NaCl was used after diluting 10-, 30-, 100-, or 300 times.

"PDGF" denotes the PDGF used as a positive control in this assay; "NC" indicates negative control where the CTGF was omitted in the assay.

REST MODE FOR CARRYING OUT THE INVENTION

The present inventions are further described in detail by referring to Examples herein below, but are not to be construed as being restricted thereto.

EXAMPLE 1

Preparation of a Polyclonal Antibody to Human CTGF

The peptide corresponding to amino acid residues in the positions of 242 to 252 of human CTGF was synthesized with a peptide synthesizer (Applied Biosystems) according to a usual method. The peptide emulsified with Freund's complete adjuvant was used as an immunogen. The peptide (0.32 mg/kg) was given subcutaneously to a New Zealand white rabbit (NZW; Simunek, Inc.). The dose and the interval were: 0.8 mg of the peptide on day 1; 0.8 mg on day 14; 0.8 mg on day 35; and 0.8 mg on day 49. The antibody titer in the serum was assayed from time to time by using the peptide. The serum was then collected according to a usual method. The polyclonal antibody (IgG) against human CTGF was purified from the serum by affinity chromatography using agarose on which the peptide was immobilized. The reactivity to human CTGF was verified by Enzyme-linked immunosorbent assay (ELISA) and Western blotting.

EXAMPLE 2

Preparation of Recombinant Human CTGF

<2-1> The transient Expression of Human Recombinant CTGF in Human Kidney-derived Fibroblast Cell Line 293

Complementary DNA encoding human CTGF was prepared according to a usual method by PCR. Specifically, the cDNA was prepared by using, as a template, heterogeneous cDNAs derived from a human chondroma cell line, HCS2/8, and by using primers designed based on the human CTGF cDNA sequence (The Journal of Cell Biology, Vol. 114, No. 6, p. 1287–1294, 1991). The human CTGF cDNA so obtained comprising the coding region was inserted into a plasmid, pcDNA3.1 (−) (Invitrogen Co.) to construct the expression vector. The human kidney-derived fibroblast cell line 293-T (ATCC CRT1573) was transformed with the prepared vector by electroporation. The transformant was cultured in a serum-free medium, ASF104 (Ajinomoto Co. Inc.), for three days, for the transient expression of the recombinant human CTGF. The human CTGF expression was confirmed by Western blotting using the polyclonal antibody prepared in Example 1.

The collected culture supernatant was subjected to salting-out with ammonium sulfate, and then to heparin-column chromatography. The column was washed with 0.3M NaCl/PBS and the human CTGF fraction was eluted with 0.5M NaCl/PBS. Thus, the partially purified human CTGF was obtained.

<2-2> Stable Expression of Human Recombinant CTGF in a Human Epithelioid Cell Line, Hela Cell Complementary DNA encoding human CTGF was prepared according to a usual method by PCR in the same manner as described in Example <2–1>. The human CTGF cDNA so obtained comprising the coding region was inserted into a plasmid, pcDNA3.1 (−) (Invitrogen Co.) to construct the expression vector. The human epithelioid cell line, Hela cell (ATCC CCL-2), was transformed with the prepared vector by electroporation. The transformants were cultured in a RPMI1640 medium containing GENETICIN (0.8 mg/ml; GIBCO-BRL) and 10% fetal calf serum for about two weeks, in order to select GENETICIN-resistant clones of the transformant. The transformant selected was cultured in the serum-free medium ASF104 (Ajinomoto Co. Inc.) for the expression of the recombinant human CTGF. The expression of the human CTGF was verified by Western blotting using the polyclonal antibody prepared in Example 1.

The collected culture supernatant was subjected to salting-out 30 with ammonium sulfate, and then to heparin-column chromatography. The column was washed with 0.3M NaCl/PBS and the human CTGF fraction was eluted with 0.5M NaCl/PBS. Thus, the partially purified human CTGF was obtained.

EXAMPLE 3

Preparation of Recombinant Mouse CTGF

Partially purified recombinant mouse CTGF was prepared by the same method described in Example 2, based on the cDNA sequence of mouse CTGF reported previously (Unexamined Published Japanese Patent Application (JP-A) No. Hei 5-255397; Cell Growth Differ., Vol. 2, No. 5, p. 225–233, 1991; FEBS Letters, Vol. 327, No. 2, p. 125–130, 1993; DNA Cell Biol., Vol. 10, No. 4, p. 293–300, 1991).

EXAMPLE 4

Preparation of Anti-human CTGF Monoclonal Antibody and Anti-mouse CTGF Monoclonal Antibody Preparation of the monoclonal antibodies in this example was performed by the conventional method described in "Experimental Medicine (supplement): Handbook for Cellular Engineering Technology, eds., T. Kuroki et al., Yodosha, page 66–74, 1992)," and "Introductory Manual for Monoclonal Antibody Experiment (T. Ando et al., Kodansha, 1991)."

Here in this example, either of the recombinant human CTGF preparations obtained by either of the two methods described in Example 2, or a mixture thereof, was used as an immunogen. The mouse CTGF used was the recombinant mouse CTGF prepared in Example 3.

The immune animals used were: (1) normal mouse (Balb/c mouse, female, 4- to 5-week old; Shizuoka experimental animal center); (2) normal rat (Wistar rat, female, 4- to 5-week old; Shizuoka experimental animal center); (3) normal hamster (Armenian hamster, male, 4- to 5-week-old; Oriental Yeast Co., Ltd.); and (4) the human antibody-producing transgenic mouse created by using the method described above (refer the following reports: Nature Genetics, Vol. 7, p. 13–21, 1994; Nature Genetics, Vol. 15, p. 146–156, 1997; Published Japanese Translation of PCT International Application No. Hei 4-504365; Published Japanese Translation of PCT International Application No. Hei 7-509137; Nikkei Science, June edition, page 40–50, 1995).

Unless otherwise stated, the same method was used for the preparation of monoclonal antibodies derived from any animal. Multi-well microplates were used for culturing cells.

<4-1> Preparation of Hybridomas Producing Anti-human CTGF Monoclonal Antibody

The above-mentioned normal mouse and the human-antibody producing transgenic mouse were immunized with the partially purified recombinant human CTGF (1 µg/animal) prepared in Example 2. The immunogen, together with complete Freund's adjuvant, was given to the mice by footpad injection for primary immunization (day 0). The recombinant human CTGF was given to the mice by footpad injection every week after the primary immunization. The booster immunization was performed four times or more in total. The final immunization was carried out by the same procedure two days before the collection of lymph node cells described hereinafter.

The lymph node cells collected from each animal and mouse myeloma cells were mixed at a ratio of 5:1. Hybridomas were prepared by cell fusion using polyethylene glycol 4000 or polyethylene glycol 1500 (GIBCO) as a fusing agent. The lymph node cells of the normal mouse were fused with mouse myeloma PAI cells (JCR No. B0113; Res. Disclosure Vol. 217, p. 155, 1982), and the lymph node cells of human antibody producing-transgenic mouse were fused with mouse myeloma P3/X63-AG8.653 cells (ATCC No. CRL 1580).

The resulting hybridomas were selected by culturing the fused cells in an ASF104 medium (Ajinomoto Co. Inc.) containing HAT supplemented with 10% fetal calf serum (FCS) and aminopterin.

The reactivity of the culture supernatant of each hybridoma clone to the recombinant human CTGF used as the immunogen was measured by ELISA described hereinafter. Many antibody producing-hybridomas were thus obtained from each animal species.

The clones named 8-64-6, 8-86-2, 8-97-3, 8-149-3, and 15-38-1 (FIG. 1) were obtained from normal mice (mouse anti-human CTGF monoclonal antibodies).

The hybridoma clones, 8-86-2 and 8-64-6, both have been deposited internationally since Dec. 18, 1997 at The National Institute of Bioscience and Human-Technology, The Agency of Industrial Science and Technology, The Ministry of International Trade and Industry (1-1-3Higashi, Tsukuba, Ibaraki, Japan) (clone 8-86-2: international deposit accession No. FERM BP-6208; clone 8-64-6: international deposit accession No. FERM BP-6209).

The clones (producing the human anti-human CTGF monoclonal antibodies) named A4.3, A11.1, A15.1, A29.6, B13.7, B22.2, B29.6, B35.1, C2.1, C26.11, C59.1, C114.4, M32.2, M33.3, M84.4, M107.2, M122, M124.6, M194.2, M244, M255, M268.1, M288.5, M291.2, M295.2, M315, M320.2, N45.2, N50.1, and N60.1 (FIGS. 1 and 2) were obtained from the human antibody-producing transgenic mice.

The hybridoma clone A11.1 has been deposited internationally since Sep. 25, 1998 at The National Institute of Bioscience and Human-Technology, The Agency of Industrial Science and Technology, The Ministry of International Trade and Industry (1-1-3 Higashi, Tsukuba, Ibaraki, Japan)(international deposit accession No. FERM BP-6535).

The hybridoma clones, B22.2, M84.4, and M320.2 have been deposited internationally since Dec. 15, 1998 at The National Institute of Bioscience and Human-Technology, The Agency of Industrial Science and Technology, The Ministry of International Trade and Industry (1-1-3 Higashi, Tsukuba, Ibaraki, Japan) (clone B22.2: international deposit accession No. FERM BP-6598; clone M84.4: international deposit accession No. FERM BP-6599; clone M320.2: international deposit accession No. FERM BP-6600).

Described above, the hybridoma clones producing the human monoclonal antibodies of the present invention are indicated by symbols all through the examples including the present example and the drawings or the tables showing the experimental results obtained in each example.

The alphabet followed by numerals up to the dot mark of each symbol corresponds to the name of parental clone. The numerals after the dot mark of the symbol means a subclone obtained from the parental clone by subcloning.

The numerals indicating the subclones may occasionally be abbreviated in any of the examples including the present example and the drawings or the tables showing the experimental results obtained in each example. However, it should be noted that the abbreviated symbols indicate the same clones as those indicated by the non-abbreviated symbols in FIGS. 1 and 2.

<4-2> Preparation of Hybridomas Producing Anti-mouse CTGF Monoclonal Antibody

The above-mentioned normal rat and normal hamster were immunized with partially purified recombinant mouse CTGF (2 µg/animal) prepared in Example 3, together with complete Freund's adjuvant, by footpad injection for primary immunization (day 0). The booster immunization was performed by footpad injection every week after the primary immunization four times or more in total. The final immunization was carried out by the same procedure two days before the collection of lymph node cells. The collection of lymph node cells is described below.

Popliteal lymph node cells were collected from each immunized animals according to a usual method by a surgical operation.

The lymph node cells collected from each animal and myeloma cells PAI (JCR No.B0113; Res. Disclosure Vol. 217, p. 155, 1982) were mixed at a ratio of 5:1. The hybridomas were prepared by cell fusion using polyethylene glycol 4000 or polyethylene glycol 1500 (GIBCO) as a fusing agent.

The hybridomas were selected by culturing the fused cells in an ASF104 medium (Ajinomoto Co. Inc.) containing HAT supplemented with 10% fetal calf serum (FCS) and aminopterin.

The reactivity of the culture supernatant of each hybridoma to the recombinant mouse CTGF used as the immunogen was measured by ELISA described hereinafter. Many antibody producing-hybridomas were, thus, obtained from each animal.

The clones (producing rat anti-mouse CTGF monoclonal antibodies) named 13-51-2, 17-132, 23-96, 24-53, 24-67, 25-91, 25-101, 25-256, 25-338, 25-410, and 25-463 (FIG. 1) were obtained from normal rats.

The clone (producing hamster anti-mouse CTGF monoclonal antibody) named 2-228-1 (FIG. 1) was obtained from normal hamster.

<4-3> Screening of Hybridomas Producing Monoclonal Antibodies by ELISA

ELISA performed in Examples <4-1> and <4-2> is as follows.

The recombinant human CTGF (0.2 μg/well) prepared in Example 2 or the recombinant mouse CTGF (0.2 μg/well) prepared in Example 3 was added into each well of a 96-well ELISA microplate (Corning Costar Co.). The plate was incubated at room temperature for 2 hours for the adsorption of the recombinant human CTGF or the recombinant mouse CTGF onto the microplate. The supernatants were discarded and then the blocking reagent (200 μl; phosphate buffer containing 3% BSA) was added into each well. The plate was incubated at room temperature for 2 hours for the blocking of CTGF-free sites on the microplate.

Each well was washed three times with 200 μl of phosphate buffer containing 0.1% Tween 20. Thus, each well of the microplate was coated with the recombinant human CTGF or recombinant mouse CTGF.

Culture supernatant (100 μl) of each hybridoma was added into each well of the plate, and the reaction was allowed to proceed for 40 minutes. Each well was then washed three times with 200 μl of phosphate buffer containing 0.1% Tween 20.

In the next step, biotin-labeled sheep anti-mouse immunoglobulin antibody (50 μl; Amersham) was added to the wells where the culture supernatant of the monoclonal antibody-producing hybridoma derived from normal mouse had been placed; biotin-labeled sheep anti-rat immunoglobulin antibody (50 μl; Amersham) was added to the wells where the culture supernatant of the monoclonal antibody-producing hybridoma derived from normal rat had been placed; biotin-labeled goat anti-hamster immunoglobulin antibody (50 μl; Cedarlane) was added to the wells where the culture supernatant of the monoclonal antibody-producing hybridoma derived from normal hamster had been placed; biotin-labeled goat anti-human immunoglobulin antibody (50 μl; American Qualex International Inc.) was added to the wells where the culture supernatant of the monoclonal antibody-producing hybridoma derived from the human antibody-producing transgenic mouse had been placed. The plates were incubated at room temperature for 1 hour.

The microplate was washed with phosphate buffer containing 0.1% Tween 20. A solution of streptavidin-β-galactosidase (50 μl; Gibco-BRL), diluted 1000 times with a solution (pH7.0) containing 20 mM HEPES, 0.5M NaCl and bovine serum albumin (BSA, 1 mg/ml), was added into each well. The plate was incubated at room temperature for 30 minutes.

Subsequently, the microplate was washed with phosphate buffer containing 0.1% Tween 20. A solution of 1% 4-Methyl-umbelliferyl-β-D-galactoside (50 μl; Sigma) in a phosphate buffer (pH7.0) containing 100 mM NaCl, 1 mM $MgCl_2$ and 1 mg/ml BSA, was added into each well. The plate was incubated at room temperature for 10 minutes. 1M $Na_2CO_3$ (100 μl) was added into each well to stop the reaction. The fluorescence intensity was measured in a FlUOROSCAN II MICROPLATE FLUOROMETER (Flow Laboratories Inc.) at a wavelength of 460 nm (excitation wavelength: 355 nm).

<4-4> Large-scale Preparation of Monoclonal Antibodies

Each hybridoma clone ($10^6$–$10^7$ cells/0.5 ml/each mouse) described above was injected intraperitoneally to ICR nude mice (female, 7- to 8-week old; Charles River). Ten to twenty days after the injection, the ascitic fluids were collected from the mice according to a usual method by opening the abdomen under anesthesia. The monoclonal antibodies were prepared from the ascitic fluids in a large quantity.

<4-5> Purification of Monoclonal Antibodies

Each monoclonal antibody-containing ascitic fluid obtained in <4-4> was centrifuged, and the resulting supernatant was diluted 3 times with 0.06M acetate buffer (pH 4.0). The pH of the dilute was adjusted to 4.8 by adding IN hydrochloric acid. Subsequently, 0.033 ml of caprylic acid (Wako Pure Chemical Industries. Ltd.) was added little by little to every 1 ml of the ascitic fluid, while stirring the mixture at room temperature. The mixture was allowed to react for 30 minutes, while being stirred. The proteins, except the antibody, were removed by centrifugation (10,000 rpm, for 20 minutes). The supernatant obtained by centrifugation was filtered by using a filter (Millipore Co.), the white precipitate was discarded. The filtrate obtained was dialyzed with phosphate buffer (for 2 hours).

After the dialysis, ammonium sulfate (26.2 g/100 ml) was added thereto little by little, while stirring the mixture at room temperature. The reaction of the mixture was carried out at 4° C. for 120 minutes, while being stirred. The resulting precipitate was then recovered by centrifugation (10,000 rpm, for 20 minutes). The recovered precipitate was dissolved with phosphate buffer and dialyzed with phosphate buffer (at 4° C., for 24 hours). Each monoclonal antibody was thus purified. <4-6> Determination of the isotype Each isotype of the above-mentioned anti-human CTGF monoclonal antibody derived from normal mouse (8-64-6, 8-86-2, 8-97-3, 8-149-3, and 15-38-1) was determined by using an isotype-determining kit for mouse monoclonal antibody (Amersham). The determination was performed according to the supplier's protocol attached to the kit. All the antibodies were determined to be IgG1/κ (FIG. 1).

Each isotype of the above-mentioned anti-human CTGF monoclonal antibody derived from the human antibody-producing transgenic mouse (A4.3, A11.1, A15.1, A29.6, B13.7, B22.2, B29.6, B35.1, C2.1, C26.11, C59.1, C114.4, M32.2, M33.3, M84.4, M107.2, M122, M124.6, M194.2, M244, M255, M268.1, M288.5, M291.2, M295.2, M315, M320.2, N45.2, N50.1, and N60.1) was determined by using an isotype-determining kit for human monoclonal antibody (American Qualex International Inc.). The determination was performed according to the supplier's protocol attached to the kit. All the antibodies were determined to be IgG2/κ (FIGS. 1 and 2).

<4-7> Preparation of the Affinity Column

An affinity column was prepared by using NHS-activated HiTrap column (HITRAP-NHS-ACTIVATED SEPHAROSE HP; 5 ml; Pharmacia Biotec.) according to the protocol attached to the product. Specifically, the preparation was done as follows:

The monoclonal antibody 8-86-2 (10 mg/ml SEPHAROSE) prepared in Example <4-5> was dissolved in a 0.2M sodium hydrogen carbonate solution (pH8.3) containing 0.5M NaCl. The solution (10 mg/ml SEPHAROSE) was loaded onto the NHS-ACTIVATED HITRAP COLUMN. The monoclonal antibody 8-86-2 was allowed to react with the NHS-ACTIVATED SEPHAROSE at 20° C. for 45 minutes, to immobilize the antibody on the SEPHAROSE.

Because of the high reactivity of the monoclonal antibody 8-86-2 to human, mouse and rat CTGFs, the affinity column prepared with the antibody can be used for purifying any human CTGF, mouse CTGF, and rat CTGF.

<4-8> Purification of Mammalian CTGF by Affinity Chromatography

Culture supernatant was collected from each culture of the HeLa transformant cells expressing human CTGF (Example <2-2>), the HeLa transformant cells expressing mouse CTGF (Example 3) and the HeLa transformant cells expressing rat CTGF (Example <11-2>). The supernatant was fractionated by heparin-column chromatography. The column was washed with 0.3M NaCl/PBS, and then the protein fraction of interest was eluted with 0.7M NaCl/PBS. Thus, the crude fractions of human, mouse and rat CTGFs were obtained.

Each crude fraction was loaded onto the affinity column, prepared in Example <4-7>, in which the anti-CTGF antibody 8-86-2 had been immobilized. The column was washed with phosphate buffer. The fraction of interest was then eluted with 0.1M glycine buffer (pH2.5) and then was neutralized with 0.75M Tris-HCl buffer (pH9.0). The eluted fractions were dialyzed against phosphate buffer. Thus, highly purified recombinant CTGFs derived from human, mouse and rat were obtained.

Figure 3:
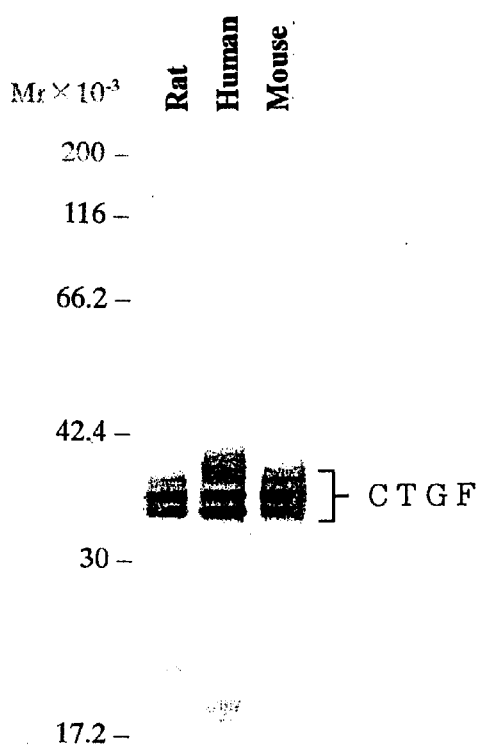
FIG. 3 is an SDS-polyacrylamide gel electrophoretic pattern of human, mouse, and rat recombinant CTGFs. The proteins were affinity purified by using a column coupled with the monoclonal antibody "8-86-2" reactive to all of human, mouse and rat CTGFS.

The purified recombinant CTGFs were electrophoresed on a sodium dodecylsulfate polyacrylamide gel with a concentration gradient of 10 to 20% polyacrylamide. The separated bands on the gel were silver-stained, and bands of about 38-kDa corresponding to human, mouse and rat CTGFs were found on the stained gel (FIG. 3).

<4-9> Examination of the Stimulatory Activity of Purified CTGF for Cell Proliferation To verify whether or not each of the CTGFs purified in Example <4-8> has a biological activity, the stimulatory activity of purified CTGF for cell proliferation was tested.

The cells of rat kidney fibroblast cells NRK-49F (ATCC CRL-1570; $2 \times 10^3$ cells/well) were cultured in a DMEM medium containing 10% fetal calf serum (FCS) in a 96-well microplate for three days. The culture supernatant was removed and the cells were washed once with the DMEM medium. Then the cells were cultured in a fresh DMEM medium for one day. Subsequently, the purified recombinant CTGF was added in various concentrations (100, 50, 25, 12.5, 6.3, and 3.1 ng/ml) into each cell culture. The culture was continued for 2 days and then [$^3$H]-thymidine (3.7kBq/ well) was added thereto. After a 6-hour culture, the cells were harvested for the measurement of [$^3$H]-thymidine uptake by the cells. The measurement was carried out in a liquid scintillation counter (Beckman). The cells were cultured in the same manner but in the absence of CTGF, and [$^3$H]-thymidine uptake by the cells was measured as a control.

Figure 4:
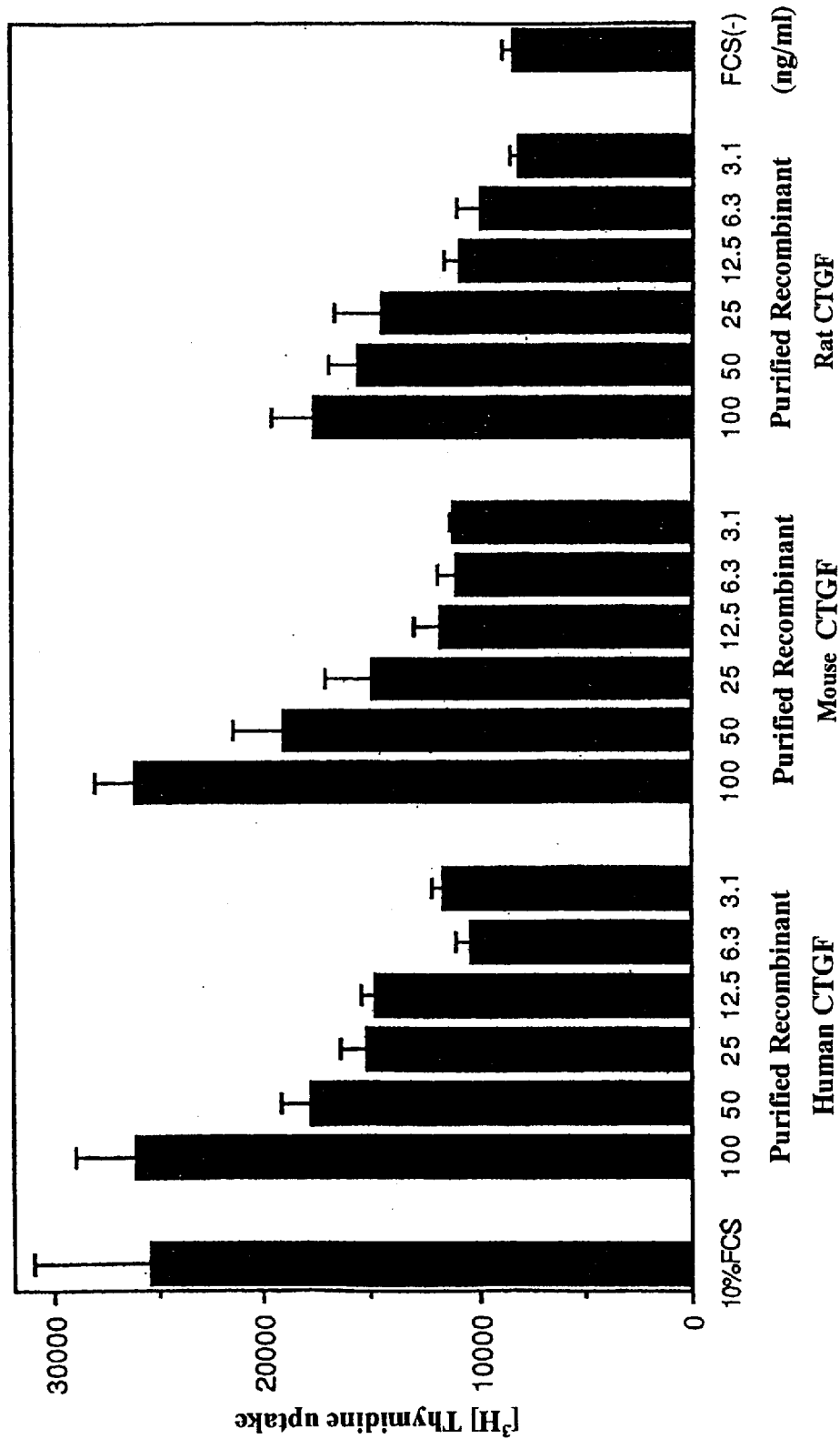
FIG. 4 shows the growth-promoting activities of human, mouse, and rat CTGFs for the rat kidney-derived fibroblast cell line NRK-49F. The proteins were affinity purified by using a column coupled with the monoclonal antibody "8-86-2" reactive to all of human, mouse, and rat CTGFs.

The result is shown in FIG. 4. It was evidenced that each of the purified recombinant CTGFS derived from human, mouse, and rat exhibited a concentration-dependent stimulatory activity for the cell proliferation and accordingly all the recombinant CTGFs possessed a biological function.

<4-10> Crossreactivity

The reactivities of various anti-human CTGF monoclonal antibodies (10 μg/ml) and anti-mouse CTGF monoclonal antibodies (10 μg/ml) to each of human CTGF, mouse CTGF and rat CTGF were tested by ELISA in the same manner described in Example <4-3>.

The microplates used in this assay were coated with each of the recombinant human, mouse and rat CTGFs purified by using affinity column prepared in Example <4-7>. The coating was performed with the proteins in the concentrations of (A) 100, 30, and 10 ng/well or (B) 100, 10, and 1 ng/well.

In the assay of (B), negative control assay was carried out by using a human monoclonal antibody against KLH (keyhole limpet hemocyanin; Pierce Chemical Co.) in the same manner described above. The anti-KLH antibody was prepared by immunizing the above-described human antibody-producing transgenic mice with KLH as an immunogen.

The assay results obtained with the concentration series (A) are shown in FIGS. 5–7; the assay results obtained with the concentration series (B) are shown in FIGS. 8–10.

The results shown in FIGS. 5–10 are also summarized in the column of "crossreactivity" in FIGS. 1 and 2.

Within the column of "crossreactivity" of FIG. 1, the results are shown in the order of 100, 30 and 10 ng/well of the coating concentration from the left. In each coating concentration, the reactivity represented by the fluorescence intensity of 1000 or more is marked with "○"; 500 or more and less than 1000, "Δ"; less than 500, "X."

Within the column of "crossreactivity" of FIG. 2, the results are shown in the order of 100, 10 and 1 ng/well of the coating concentration from the left. In each coating concentration, the reactivity represented by the fluorescence intensity of 1000 or more is marked with "○"; 500 or more and less than 1000, "Δ"; less than 500, "X."

Thus, it was revealed that the monoclonal antibodies of the present invention had a variety of characteristics in terms of the crossreactivity.

<4-11> Activity of Inhibiting the Binding of CTGF to Various Cells

A recent study has revealed that CTGF is involved in cell adhesion (Exp. Cell. Res., Vol. 233, p. 63–77, 1997). The inhibiting effect of the various monoclonal antibodies prepared above on the CTGF-mediated cell adhesion was investigated as an index of judging whether or not the antibodies have the activity (neutralizing activity) of inhibiting the CTGF functions. The test was performed by using the three distinct methods described below in <4-11-1> to <4-11-3>.

<4-11-1> Inhibition of the Binding of CTGF with Human Kidney-derived Fibroblast Cell Line 293-T The above-prepared various monoclonal antibodies (0.5 µg/well) reactive to human CTGF were added into the wells of a microplate coated with the recombinant human CTGF (the coating concentration: 0.5 µg/well). The immobilization of the human CTGF on the plate was performed by the same procedure described in Example <4-3>. The above-prepared various monoclonal antibodies (0.5 µg/well) reactive to mouse CTGF were added into the wells of a microplate coated with the recombinant mouse CTGF (the coating concentration: 0.5 µg/well). The immobilization of the mouse CTGF on the plate was performed by the same procedure described in Example <4-3>.

The supernatants were removed from each plate, and then the cells of human kidney-derived fibroblast cell line 293-T (ATCC CRL1573) labeled with 2',7'-bis(2-carboxyethyl)-5 (6)-carboxyfluorescein tetraacetoxymethyl ester (BCECF; Molecular Probes Inc.) were added into each well ($5 \times 10^4$ cells/well). The plates were allowed to stand at 4° C. for 1 hour.

The floating cells were removed and then the cells adhering to the plates were solubilized by adding phosphate buffer (100 µl) containing 1% NP-40 thereto. The release of BCECF into the culture supernatant was caused by cytolysis. The intensity of fluorescence emitted by BCECF was measured by the FLUOROSCAN II MICROPLATE FLUOROMETER (Flow Laboratories Inc.).

Control assay was carried out in the same manner described above but without any antibodies added.

The results are shown in FIG. 11. The results shown in FIG. 11 are also summarized in the column of "Activity of inhibiting the binding of 293 cells" in FIG. 1. In the column of FIG. 1, the mark "◯" indicates that the cell adhesion was inhibited significantly by the antibody, and the mark "X" indicates that the antibody exhibited no inhibiting activity.

<4-11-2> Inhibition of the Binding of CTGF with Rat Kidney-derived Broblast Cell Line NRK-49F The above-prepared various monoclonal antibodies (the final concentration: 20 µg/well, 6 µg/well or 2 µg/well) reactive to the human CTGF were added into the wells of a microplate coated with the recombinant human CTGF (the coating concentration: 1 µg/well) prepared by the same procedure described in Example <4-3>.

The cells of rat kidney-derived fibroblast cell line NRK-49F (ATCC CRL1570) labeled with 2',7'-bis(2-carboxyethyl)-5(6)-carboxyfluorescein tetraacetoxymethyl ester (BCECF; Molecular Probes Inc.) were added into each well ($1 \times 10^4$ cells/well). The plates were allowed to stand at 4° C. for 1 hour.

The floating cells were removed and then the cells adhering to the plates were solubilized by adding phosphate buffer (100 µl) containing 1% NP-40 thereto. The release of BCECF into the culture supernatant was caused by cytolysis. The intensity of fluorescence emitted by BCECF was measured by the FLUOROSCAN II MICROPLATE FLUOROMETER (Flow Laboratories Inc.).

Control assay was carried out in the same manner described above but without any antibodies added. Negative control assay was carried out by using human monoclonal antibody against KLH (keyhole limpet hemocyanin; Pierce Chemical Co.) in the same manner described above.

The anti-KLH antibody was prepared by immunizing the above-described human antibody-producing transgenic mice with KLH.

Another control assay was performed in the same manner described above but without any antibodies added and by using a microplate on which no CTGF was immobilized.

The results are shown in FIG. 12. The result is shown as a rate (%) of bound cells, which is calculated based on the value of fluorescence intensity determined.

The results shown in FIG. 12 are also summarized in the column of "Activity of Inhibiting the Binding of NRK Cells" in FIG. 2. In the column of FIG. 2, the mark "◯" indicates that the cell adhesion was significantly inhibited by the antibody, and the mark "X" indicates that the antibody exhibited weak inhibiting activity or no activity.

<4-11-3> Inhibition of the Binding of CTGF with Various Cells

The above-prepared various monoclonal antibodies (the final concentration: 20 µg/well) reactive to human CTGF were added into the wells of microplate coated with the recombinant human CTGF (the coating concentration: 1 µg/well) prepared by the same procedure described in Example <4-3>.

After the plates were allowed to stand for 60 minutes and the supernatants were removed from each plate, the cells ($1 \times 10^4$ cells/well) indicated below labeled with 2',7'-bis(2-carboxyethyl )-5(6)-carboxyfluorescein tetraacetoxymethyl ester (BCECF; Molecular Probes Inc.) were added into each well. The plates were allowed to stand at 4° C. for 1 hour. The following cells were used in this assay:

(1) human lung-derived fibroblast cell (NHLF2837; Clonetics);

(2) human osteosarcoma-derived cell line MG-63 (ATCC CRL1427); and (3) rat kidney-derived fibroblast cell line NRK-49F (ATCC CRL1570).

The floating cells were removed and then the cells adhering to the plates were solubilized by adding phosphate buffer (100 µl) containing 1% NP-40 thereto. The release of BCECF into the culture supernatant was caused by cytolysis. The intensity of fluorescence emitted by BCECF was measured in the FLUOROSCAN II MICROPLATE FLUOROMETER (Flow Laboratories Inc.).

Control assay was carried out in the same manner described above but without any antibodies added. Negative control assay was carried out by using human monoclonal antibody against KLH (keyhole limpet hemocyanin; Pierce Chemical Co.) in the same manner described above. The anti-KLH antibody was prepared by immunizing the above-described human antibody-producing transgenic mice with KLH.

Another control assay was performed in the same manner described above but without any antibodies added and by using a microplate on which no CTGF was immobilized.

The results are shown in FIG. 13. The result is shown as a rate (%) of bound cells, which is calculated based on the value of fluorescence intensity determined.

<4-12> Crossreactivity to Rabbit Tissues

Arteriosclerotic lesions were obtained from the hyperlipidemia model rabbit WHHL (Oriental Yeast Co., Ltd.) by a surgical operation.

Frozen sections were prepared from the arteriosclerotic lesions according to a usual method.

Each section was stained by using a Vectastain Elite ABC kit (Funakoshi Ltd.) according to the procedure described below.

After being fixed with acetone for 1–2 minutes and dried, the sections were moistened with a diluted serum (10 ml PBS/150 µl serum) for 30 minutes. The sections were washed with PBS, and then primary antibodies (10 µg/ml or culture supernatant of hybridoma) were added. The primary antibodies used are the above-mentioned anti-human CTGF monoclonal antibodies (clone: 8-86-2 and 8-149–3) derived from normal mouse; anti-mouse CTGF monoclonal antibody derived from normal rat (clone: 13-51-2); and anti-human CTGF monoclonal antibodies derived from the human antibody-producing transgenic mouse (clone: A4.3, A11.1, A29.6, B29.6, B35.1, C26.11, and C114.4). The sections were allowed to stand for 40 minutes.

Subsequently, each section was washed with PBS, and then a solution of biotinylated secondary antibody (100 μl) was added. The sections were allowed to stand for 30 minutes. Biotin-labeled horse anti-mouse immunoglobulin antibody was used as the secondary antibody when the primary antibody added was the anti-human CTGF monoclonal antibody derived from normal mouse; biotin-labeled rabbit anti-rat immunoglobulin antibody was used as the secondary antibody when the primary antibody added was the anti-mouse CTGF monoclonal antibody derived from normal rat; biotin-labeled goat anti-human immunoglobulin antibody was used as the secondary antibody when the primary antibody added was the anti-human CTGF monoclonal antibody derived from the human antibody-producing transgenic mouse.

Each section was allowed to stand in a methanol solution containing 3% hydrogen peroxide for 10 minutes and then washed with PBS. Then 100 μl of an avidin-peroxidase solution (PBS (5 ml)/peroxidase-labeled avidin DH (100 μl)/biotinylated hydrogen peroxide H (100 μl) was added to the sections. The sections were allowed to stand for 30 minutes.

After washing with PBS, a diaminobenzidine tetra hydrochloride solution (DAB)(Water (5 ml)/buffer solution (100 μl)/DAB solution (200 μl)/hydrogen peroxide solution (100 μl)) was added to the sections. The sections were allowed to stand for 2–10 minutes.

After washing with cold water for 5 minutes, the sections were subjected by Giemsa staining method and mounted. Control staining was carried out in the same manner by using as a primary antibody a monoclonal antibody, which is non-reactive to CTGF and is identical in isotype to the corresponding monoclonal antibody to be tested. The stained and mounted sections were observed under a microscope with magnifications of X100 and X200. The results are shown in FIG. 14. The results shown in FIG. 14 are also summarized in the column of "Reactivity to Tissues from Arteriosclerotic Lesions of WHHL rabbit" in FIG. 1. In the column of FIG. 1, the mark "○" indicates that the tissue was stained with the antibody, and the mark "X" indicates that the tissues was weakly stained or not stained with the antibody.

Anti-human CTGF monoclonal antibody clones derived from the human antibody-producing transgenic mouse, A4.3, A11.1, A29.6, C26.11 and C114.4, and a clone of anti-mouse CTGF monoclonal antibody derived from normal rat, 13-51-2, exhibited the reactivity to the tissues from arteriosclerotic lesions of rabbit.

<4-13> Activity of Inhibiting Cell Proliferation by a Stimulus with CTGF

As shown above in Example <4-9>, CTGF induces proliferation of a variety of cells (for example, fibroblast cells derived from various tissues such as the kidney and lung, a variety of tumor cells, and vascular endothelial cells).

In the present experiment, the inhibiting effect of the monoclonal antibodies of the present invention on the CTGF-stimulated cell proliferation was examined described below.

<4-13-1> Preparation of Cell Culture Medium Containing CTGF

Neonatal human dermal fibroblast cells (NHDF; Becton Dickinson) were cultured in a dish. The cells were washed twice with a fetal calf serum (FCS)-free DMEM medium and then further cultured with a fresh DMEM medium containing human transforming growth factor-β (TGF-β; 1 ng/ml; R&D Systems) for 1 day.

The culture supernatant was recovered, and loaded onto to a heparin column (HITRAP; Pharmacia Biotech). The column was washed with 0.2M NaCl/PBS, and then the factor trapped in the column was eluted with 0.6M NaCl/PBS. The eluate was dialyzed with PBS and was used for the cell proliferation assay described below.

Because CTGF is a heparin-binding protein, CTGF can be partially purified by using a heparin column. The presence of CTGF in the sample obtained above was confirmed according to a usual method by Western blotting using the rabbit anti-human CTGF polyclonal antibody prepared in Example 1.

Control assay was carried out by using pre-immune serum prepared from the rabbit (the same rabbit described in Example 1) prior to the immunization with human CTGF.

The results are shown in FIG. 24.

<4-13-2> Cell Proliferation by a Stimulus with Purified CTGF

The cells of rat kidney-derived fibroblast cell line NRK-49F (ATCC CRL-1570; $1 \times 10^4$ cells/well) were placed in the wells of a 96-well microtiter plate, and cultured for 1 day. The plate was washed twice with a FCS-free DMEM medium. Then the cells were further cultured for 1 day. Subsequently, the CTGF sample prepared above in <4-13-1> (diluted 10, 30, 100 and 300 times with a DMEM medium) was added into each well, the culture was continued for 18 hour. [$^3$H]-thymidine (3.7 kBq/well) was added into each well, and the culture was further continued for 6 hours. The cells were harvested for the measurement of [$^3$H]-thymidine uptake by the cells. The measurement was carried out in a liquid scintillation counter (Beckman).

Positive control experiment was carried out with PDGF in the same manner. Negative control experiment was performed in the same manner but without CTGF added.

The results are shown in FIG. 25.

<4-13-3> Activity of Inhibiting Cell Proliferation

The CTGF sample (diluted 20 times with a DMEM medium) prepared above in <4-13-1> was allowed to react for 30 minutes with the human anti-human CTGF monoclonal antibodies of the present invention (the final concentration: 20 μg/ml, 2 μg/ml, or 0.2 μg/ml) that was prepared above. The same experiment described in <4-13-2> was carried out with the mixture.

Positive control assay was carried out in the same manner but without any antibodies added. Negative control assay was performed in the same manner in the absence of any of the CTGF samples and the antibodies.

The results are shown in FIGS. 15 and 16.

The same experiment described above was repeated several times. The results including those shown in FIGS. 15 and 16 are summarized in the column "Activity of Inhibiting the proliferation of NRK Cells" of FIG. 2. In the column of FIG. 2, the mark "○" indicates that the cell proliferation was significantly inhibited by the antibody.

Thus, it was revealed that the human anti-human CTGF monoclonal antibodies of the present invention significantly suppressed or inhibited the proliferation of human fibroblast cells.

<4-14> Epitope Mapping

The experiment described below was performed to determine the sites (epitopes) in the structure of human CTGF responsible for the specific binding with the human anti-human CTGF monoclonal antibodies of the present invention.

This experiment was carried out by the inventive sandwich ELISA 30 with two antibodies. The method of the sandwich ELISA of the present invention is described in detail in Example 5. Specifically, the experiment was conducted according to the following steps:

(Step 1)

Antibody-immobilized microplates, on which each of the human 35 anti-human CTGF monoclonal antibodies (0.3 µg/50 µl /well) listed in FIG. 2 was immobilized, were prepared in the same manner described later in Example <5-1>.

(Step 2)

Labeled monoclonal antibodies were prepared in the same manner described later in Example <5-2>, by using the monoclonal antibodies, A, B, C and D, of the present invention, as follows:

[Antibody A]

Mouse monoclonal antibody 8-64-6 reactive to human CTGF (derived from a hybridoma identified by international deposit accession No. FERM BP-6209);

[Antibody B]

Human anti-human CTGF monoclonal antibody A11.1 (derived from a hybridoma identified by international deposit accession No. FERM BP-6535);

[Antibody C]

Human anti-human CTGF monoclonal antibody C26.11 (consisting of the heavy chain having an amino acid sequence comprising the amino acid sequence of SEQ ID NO: 8 as well as the light chain having an amino acid sequence comprising the amino acid sequence of SEQ ID NO: 18);

[Antibody D]

Human anti-human CTGF monoclonal antibody C59.1 (consisting of the heavy chain having an amino acid sequence comprising the amino acid sequence of SEQ ID NO: 10 as well as the light chain having an amino acid sequence comprising the amino acid sequence of SEQ ID NO: 20).

(Step 3)

ELISA was conducted in the same manner described later in Example <5-3>. Specifically, the purified recombinant human CTGF prepared in the above example was added (15 ng/well) into the wells of each antibody-immobilized microplate prepared in Step 1. After the antigen-antibody reaction was allowed to proceed, the respective labeled monoclonal antibodies prepared in Step 2 were added (0.1 µl/50 µl/well) and reacted thereto. After the subsequent treatment conducted in the same manner described later in Example <5-3>, the reaction was stopped by adding a stop solution into each well. The intensity of fluorescence emitted in each well was measured with the fluorometer at a wavelength of 460 nm (excitation: 355 nm).

The value of fluorescence intensity obtained is expected to depend on the positional relationship between the site (epitope) on the human CTGF bound with the monoclonal antibody immobilized on the microplate and the site (epitope) on the human CTGF bound with the labeled monoclonal antibody. Accordingly, the results are predicted to be described below in (1) to (3).

(1) When the site (epitope) on the human CTGF where the monoclonal antibody immobilized on the microplate binds, is identical to the site (epitope) on the human CTGF where the labeled monoclonal antibody binds, then the labeled antibody added later cannot react with the antigen-antibody complex consisting of the human CTGF and the monoclonal antibody immobilized on the microplate. Therefore, the value of fluorescence intensity to be measured in Step 3 can be sufficiently near 0 in this case.

(2) When the site (epitope) on the human CTGF where the monoclonal antibody immobilized on the microplate binds, is adjacent to the site (epitope) on the human CTGF where the labeled monoclonal antibody binds, then, because of some steric hindrance around the site, the labeled antibody added later becomes less reactive to the antigen-antibody complex consisting of the human CTGF and the monoclonal antibody immobilized on the microplate. Therefore, the value of fluorescence intensity to be measured in Step 3 is expected to be low in this case.

(3) When the site (epitope) on the human CTGF where the monoclonal antibody immobilized on the microplate binds, is distant from the site (epitope) on the human CTGF where the labeled monoclonal antibody binds, then the labeled antibody added later can react with the antigen-antibody complex consisting of the human CTGF and the monoclonal antibody immobilized on the microplate. Therefore, the value of fluorescence intensity to be measured in Step 3 can be significantly high in this case.

The result of the experiment agreed with the above prediction. The result is shown in the column of "Epitope mapping" of FIG. 2.

The meaning of each alphabet used in the column of FIG. 2 is illustrated bellow.

"(A)" indicates the "Antibody A" used above as the labeled antibody;

"(B)" indicates the "Antibody B" used above as the labeled antibody;

"(C)" indicates the "Antibody C" used above as the labeled antibody;

"(D)" indicates the "Antibody D" used above as the labeled antibody;

"A" indicates an epitope identical or almost identical to the epitope of "Antibody A";

"B" indicates an epitope identical or almost identical to the epitope of "Antibody B";

"C" indicates an epitope identical or almost identical to the epitope of "Antibody C";

"D" indicates an epitope identical or almost identical to the epitope of "Antibody D";

"-" indicates an epitope which is different from any of the epitopes of "Antibody A," "Antibody B," "Antibody C" and "Antibody D";

"B/C" indicates an epitope identical or almost identical to the epitope of "Antibody B" and/or the epitope of "Antibody C";

"A-/B" indicates an epitope close to the epitope of "Antibody A" in position and identical or almost identical to the epitope of "Antibody B."

Others are indicated in the same manner as indicated above.

<4-15> Therapeutic Effect on Kidney Diseases and Fibrotic Diseases in Tissues

The therapeutic effect of the human anti-human CTGF monoclonal antibodies of the present invention on various diseases was studied by using a mouse model of the diseases.

The mouse model used in this study is a disease model exhibiting a part of the pathologic features or a part of clinical findings as observed in any of the diseases and morbid conditions indicated below.

The therapeutic effect found in the present study should be considered to represent all of the therapeutic effects on the diseases or morbid conditions indicated below:

kidney diseases (renal failure, nephritis, kidney fibrosis, etc.), various fibrotic diseases in tissues (kidney fibrosis, pulmonary fibrosis, hepatic fibrosis, tissue fibrosis of skin, etc., fibrosis of synovial tissue associated with rheumatoid arthritis and fibrotic diseases associated with various cancers), skin diseases (scleroderma, psoriasisa, atopic dermatitis, etc.), liver diseases (cirrhosis, hepatic fibrosis, hepatitis, etc.), lung diseases (pulmonary fibrosis, pneumonia, etc.) and rheumatoid arthritis and arteriosclerosis, etc.

<4-15-1> Preparation of a Disease Model Mouse

The left side abdomen of each B6C3F1 mouse (male, 7-week old, 6 individuals per each group, SLC) was opened by a surgical operation under anesthesia with pentobarbital (50 mg/kg). The ureter extending from the left kidney was ligated with sutures at two sites and then cut between the two ligated sites (UUO, unilateral ureteral obstruction). After this treatment, the opened abdominal part was sutured. This operation results in the loss of the most important function in the left kidney-the normal renal filtering function of body fluids such as blood. A variety of pathological manifestations as seen in various kidney diseases are observed in the operated kidney.

<4-15-2> Therapeutic Effect of Anti-CTGF Monoclonal Antibody

The human anti-human CTGF monoclonal antibody, M84 or M32 (prepared in the previous Example) was dissolved in a phosphate buffer and given to the above-prepared model mice by intraperitoneal injection (5 mg/kg). The administration of the antibody was carried out, for the first time, immediately after the operation, and then every third day, four times in total. After the final administration (14 days after the operation), the left kidney was removed from each mouse by a surgical operation. The extracted kidneys were delipidated and dehydrated with acetone, and the proteins were hydrolyzed by using 6N hydrochloric acid. Subsequently, the samples were dried, while being kept warm and blown with nitrogen gas, and dissolved in purified water to serve as the assay samples. The contents of hydroxyproline (OH-proline) in the samples from kidney tissues were determined according to a previously reported method (Analytical Biochemistry, Vol. 55, p. 288–291, 1973; Kidney Lnt., Vol. 54, No. 1, p. 99–109, 1998).

The increased hydroxyproline level in the kidney is an index of the onset of nephritis and kidney fibrosis resulting from renal failure. Accordingly, the decrease in the hydroxyproline concentration indicates that the monoclonal antibodies are useful for the treatment of kidney diseases. Control experiments were carried out as follows in the same manner described above:

(1) Phosphate buffer alone (without any antibodies) was given intraperitoneally to mice treated with the above-mentioned UUO (ureter ligation treatment) in the same manner described above.

(2) The abdomen was opened and then sutured without performing UUO in normal mice.

(3) No surgical operation with the UUO treatment was performed in normal mice.

(4) Mice were fed with food in which Pirfenidone (Kidney Int. Vol. 54, No. 1, p. 99–109, 1998) was mixed, instead of the antibody treatment described above (positive control experiment). Pirfenidone is a drug for the treatment of fibrotic diseases such as kidney fibrosis and is being under clinical trial.

The results are shown in FIG. 17.

These results illustrated that the monoclonal antibodies of the present invention had significant suppressing effects and therapeutic effects on the kidney diseases and tissue fibrotic diseases.

Surprisingly, the efficacy of the monoclonal antibodies of the present invention is the same as that of the drug used in a high dose as a positive control (for example, the amount of the drug given to mice corresponds to about 100 g, in total, if the drug is administered four times to a patient with 50 kg of body weight).

<4-16> Determination and Analysis of Gene Sequence and Amino Acid Sequence of Human Anti-human CTGF Monoclonal Antibody Nucleotide sequencing was carried out as described below to determine the cDNA sequence encoding the variable region of the heavy chain of each human monoclonal antibody against human CTGF prepared in the above examples as well as the cDNA sequence encoding the viable region and constant regions of the light chain of the antibody. The structural features of the genes were also analyzed. The procedures of sequencing analysis used in this example is schematically illustrated in FIG. 18.

After culturing, the hybridomas (clone: A29, C26, C59, C114, and M295; about $5\times10^7$ cells), which were prepared in the previous example, producing the human anti-human CTGF monoclonal antibodies, were centrifuged and the resulting precipitates were recovered. The cells were stored at −80° C. for the later polyA+RNA extraction.

PolyA$^+$ RNA was extracted and purified from each hybridoma using a commercial product, FASTRACK 2.0 KIT (Invitrogen Co.), as follows. Each of the above frozen cell samples were lysed in a lysis buffer and solubilized by homogenizing with POLYTRON. After incubating at 45° C., the solubilized materials were mixed with Oligo (dT) cellulose, and the mixtures were shaken gently for about 1 hour. Subsequently, the Oligo (dT) cellulose was washed, and then polyA$^+$ RNAs were eluted with an elution buffer. Eluted PolyA$^+$ RNAs were precipitated with ethanol, and then dissolved in 20 μl of Tris-EDTA buffer. The concentrations of obtained polyA$^+$ RNAs were determined by measuring absorbance at a wave length of 260nm.

Complementary DNAs were prepared by using the obtained polyA+RNAs as templates by RACE-PCR with a commercially available product, MARATHON cDNA AMPLIFICATION KIT (CLONTECH), according to a usual procedure ("PCR Method for Gene Amplification: Basic Techniques and Recent Advancement" Kyoritsu Shuppan Co., Ltd., p.13–15, 1992). Specifically, the first-strand cDNA synthesis was performed using the polyA$^+$ RNA (1–5 μg) purified from each of the hybridomas as a template, and then the second strand was prepared from the first strand. The cDNAs were extracted once with phenol/chloroform/isoamyl alcohol and then treated once with chloroform. The cDNAs were precipitated with ethanol. An adaptor DNA (SEQ ID NO: 25) was ligated to the cDNAs. The resultant DNA products were diluted 250 times. The respective cDNAs encoding the heavy chain and the light chain of the antibody were prepared by using the dilutes as templates by PCR in a usual manner. The primer of SEQ ID NO: 26 was used in the PCR for the antibody heavy chain. The primer of SEQ ID NO: 27 was used in the PCR for the antibody light chain.

Each PCR product was fractionated by agarose-gel electrophoresis, and the DNAs of interest were recovered therefrom. The nucleotide sequences of the respective cDNAs obtained were determined by using a commercially available reagent, DYE TERMINATOR CYCLE SEQUENCING FS KIT (PE-Applied Biosystems) and a PRISM377 DNA Sequencer (PE-Applied Biosystems). Sequencing Primers used in the sequence determination were the same as those used in the above PCR amplification.

Based on the sequences obtained, appropriate sequencing primers were designed and prepared for further sequencing analysis.

Sequence listing attached hereto contains the cDNA sequence encoding the variable region of the heavy chain of each human monoclonal antibody against human CTGF produced by the above-mentioned hybridomas; the cDNA sequence encoding the variable region of the light chain of each of the antibodies; and the deduced amino acid sequences thereof.

<Clone A29>
 (Variable Region of the Heavy Chain)
  DNA sequence: SEQ ID NO: 5 (signal sequence: nucleotides 1–57, V region: nucleotides 58–363)
  Amino acid sequence: SEQ ID NO: 6 (signal sequence: amino acids 1–19, variable region: comprising amino acids 21–120)
 (Variable Region of the Light Chain)
  DNA sequence: SEQ ID NO: 15 (signal sequence: nucleotides 1–60, V region: nucleotides 61–365)
  Amino acid sequence: SEQ ID NO: 16 (signal sequence: amino acids 1–20, variable region: comprising amino acids 21–120)
<Clone C26>
 (Variable Region of the Heavy Chain)
  DNA sequence: SEQ ID NO: 7 (signal sequence: nucleotides 1–30 57, V region: nucleotides 58–357)
  Amino acid sequence: SEQ ID NO: 8 (signal sequence: amino acids 1–19, variable region: comprising amino acids 21–118)
 (Variable Region of the Light Chain)
  DNA sequence: SEQ ID NO: 17 (signal sequence: nucleotides 1–60, V region: nucleotides 61–364)
  Amino acid sequence: SEQ ID NO: 18 (signal sequence: amino acids 1–20, variable region: comprising amino acids 21–121)
<Clone C59>
 (Variable Region of the Heavy Chain)
  DNA sequence: SEQ ID NO: 9 (signal sequence: nucleotides 1–57, V region: nucleotides 58–350)
  Amino acid sequence: SEQ ID NO: 10 (signal sequence: amino acids 1–19, variable region: comprising amino acids 21–116)
 (Variable Region of the Light Chain)
  DNA sequence: SEQ ID NO: 19 (signal sequence: nucleotides 1–66, V region: nucleotides 67–353)
  Amino acid sequence: SEQ ID NO: 20 (signal sequence: amino acids 1–22, variable region: comprising amino acids 23–117)
<Clone C114>
 (Variable Region of the Heavy Chain)
  DNA sequence: SEQ ID NO: 11 (signal sequence: nucleotides 1–57, V region: nucleotides 58–350)
  Amino acid sequence: SEQ ID NO: 12 (signal sequence: amino acids 1–19, variable region: comprising a segment of amino acids 21–116)
 (Variable Region of the Light Chain)
  DNA sequence: SEQ ID NO: 21 (signal sequence: comprising nucleotides 1–47, V region: nucleotides 48–335)
  Amino acid sequence: SEQ ID NO: 22 (signal sequence: comprising amino acids 1–16, variable region: comprising amino acids 17–111)
<Clone M295>
 (Variable Region of the Heavy Chain)
  DNA sequence: SEQ ID NO: 13 (signal sequence: nucleotides 1–58, V region: nucleotides 59–353)
  Amino acid sequence: SEQ ID NO: 14 (signal sequence: amino acids 1–19, variable region: comprising amino acids 21–117)
 (Variable Region of the Light Chain)
  DNA sequence: SEQ ID NO: 23 (signal sequence: nucleotides 1–66, V region: nucleotides 67–356)
  Amino acid sequence: SEQ ID NO: 24 (signal sequence: amino acids 1–22, variable region: comprising amino acids 23–118)

By using a gene sequence-analyzing computer software, a library of variable region genes of human immunoglobulin, V BASE SEQUENCE, constructed by Tomlinson et al. (Immunol. Today, Vol. 16, No. 5, p. 237–242, 1995) was searched for the respective DNA sequences determined.

The result showed that the respective V region genes of the heavy and light chains of the above-mentioned human monoclonal antibodies are composed of the segments indicated below.

<Gene for Heavy-chain V Region>
 Clone A29: DP-38
 Clone C26: DP-75
 Clone C59: DP-5
 Clone C114: DP-5
 Clone M295: DP-65
<Gene for Light-chain V Region>
 Clone A29: DPK24
 Clone C26: DPK12
 Clone C59: DPK1
 Clone C114: DPK1
 Clone M295: DPK9

It is assumed that N-additions are located between the V region and the downstream D region as well as between the D region and the further downstream J region in the cDNA sequences encoding the heavy chains of the above human monoclonal antibodies.

EXAMPLE 5

Establishment of a Sandwich ELISA System for Assaying Human CTGF and Mouse CTGF

<5-1> Preparation of a Antibody-immobilized Microplate

In this example, the monoclonal antibody 8-64-6 (derived from a hybridoma identified by international deposit accession No. FERM BP-6209), which was derived from normal mouse and prepared in the above-described manner, was used as a monoclonal antibody which is immobilized on a microplate. This monoclonal antibody is highly reactive to human CTGF and crossreactive to mouse CTGF.

The monoclonal antibody 8-64-6 was diluted with phosphate buffer and added at a concentration of 1 $\mu$g/50 $\mu$l/well into each well of a 96-well ELISA microplate (Corning Costar Co.). The plate was incubated at room temperature for 1 hour for adsorbing the antibody onto the plate.

Subsequently, the plate was washed with a phosphate buffer and then a phosphate buffer (200 $\mu$l/well) containing 3% bovine serum albumin (BSA) was added into each well. The plate was incubated at room temperature for 2 hours for the blocking of antibody-free sites on the microplate. The plate was washed three times with phosphate buffer.

<5-2> Preparation of a Labeled Monoclonal Antibody

In this example, the monoclonal antibody 8-86-2 (derived from a hybridoma identified by international deposit accession No. FERM BP-6208), which was derived from normal mouse and prepared in the above-described manner, was used as a monoclonal antibody for the labeling. This monoclonal antibody is highly reactive to human CTGF, mouse CTGF, and rat CTGFs.

One milliliter of the monoclonal antibody 8-86-2 (20 mg/ml) was dialyzed with 0.1M NaHCO3 (pH8.2–8.3) solution (at 4° C. for 24 hours). Then 100 µl of NHS-biotin (2 mg/ml; Pierce Chemical Co.) was added thereto and stirred vigorously. After the reaction was continued at room temperature for 30 minutes, the mixture was dialyzed with phosphate buffer (at 4° C. for 24 hours).

<5-3> Establishment of a Assay Method Using Sandwich ELISA

The sandwich ELISA system for assaying human CTGF and mouse CTGF, which was established in the present invention, is as follows.

Samples (50 µl/well) to be assayed were added into each well of the antibody-immobilized microplate prepared in Example <5-1> and incubated at room temperature for 1 hour. The microplate was washed three times with phosphate buffer containing 0.1% Tween 20. The biotin-labeled monoclonal antibody prepared in Example <5-2> was diluted with a phosphate buffer containing 1% BSA and 0.1% Tween 20 and added (0.3 µl/50 µl/well) into the respective wells. The plate was incubated at room temperature for 1 hour.

The microplate was washed three times with phosphate buffer containing 0.1% Tween 20. A solution of streptavidin-β-galactosidase (50/11; Gibco-BRL), diluted 1000 times with a solution (pH7.0) containing 20 mM HEPES, 0.5M NaCl and BSA (1 mg/ml), was added into each well. The plate was incubated at room temperature for 30 minutes.

The microplate was washed three times with phosphate buffer containing 0.1% Tween 20. A solution of 1% 4-Methyl-umbelliferyl-β-D-galactoside (50 µl; Sigma) in a phosphatebuffer (10 mM, pH7.0, containing Na and K ions) containing 100 mM NaCl, 1 mM $MgCl_2$ and 1 mg/ml BSA, was added into each well. The plate was incubated at room temperature for 10 minutes.

1M $Na_2CO_3$ (100 µl) was added to each well to stop the reaction. The fluorescence intensity was measured by the FLUOROSCAN II MICROPLATE FLUOROMETER (Flow Laboratories Inc.) at a wavelength of 460nm (excitation wavelength: 355 nm). The amount of human CTGF or mouse CTGF in the sample were determined by using the calibration curves as prepared in the following example.

<5-4> Preparation of the Calibration Curve

The calibration curve was prepared by using the sandwich ELSA established in Example <5-3>, in which the labeled CTGF standard used was the affinity-purified recombinant human CTGF or recombinant mouse CTGF, which were prepared in Example <4–8>. The result is shown in FIG. 19.

The calibration curve for human CTGF was obtained with a significant difference even within an extremely low concentration range of 3 ng/ml to 1000 ng/ml. The calibration curve for mouse CTGF was also obtained with a significant difference for a concentration range of 30 ng/ml to 1000 ng/ml. However, rat CTGF was not measurable in the sandwich ELISA system established in Example <5-3>.

EXAMPLE 6

Establishment of a Sandwich ELISA System for Assaying Mouse CTGF and Rat CTGF

<6-1> Preparation of Antibody-immobilized Microplate

In this example, the monoclonal antibody 13-51-2, which was derived from normal rat and prepared in the above-described manner, was used as a monoclonal antibody which is immobilized on a microplate. This monoclonal antibody is highly reactive to mouse CTGF and crossreactive to rat CTGF.

The monoclonal antibody 13-51-2 was diluted with phosphate buffer and added at a concentration of 1 µg/50 µl/well into each well of a 96-well ELISA microplate (Corning Costar Co.). The plate was incubated at room temperature for 1 hour for adsorbing the antibody onto the plate.

Subsequently, the plate was washed with a phosphate buffer and then a phosphate buffer (200 µl /well) containing 3% Bovine serum albumin (BSA) was added into each well. The plate was incubated at room temperature for 2 hours for the blocking of antibody-free sites on the microplate. The plate was washed three times with phosphate buffer.

<6-2> Preparation of a Labeled Monoclonal Antibody

In this example, labeled monoclonal antibody was the biotin-labeled monoclonal antibody prepared in Example <5-2>.

Specifically, the labeled monoclonal antibody was prepared by labeling, with biotin, the antibody 8-86-2 (derived from a hybridoma identified by international deposit accession No. FERM BP-6208) highly reactive to all of human CTGF, mouse CTGF, and rat CTGF.

<6-3> Establishment of a Assay Method Using Sandwich ELISA

The sandwich ELISA system for assaying mouse CTGF and rat CTGF, which was established in the present invention, is as follows. Samples (50 µl/well) to be assayed were added into each well of the antibody-immobilized microplate prepared in Example <6-1> and incubated at room temperature for 1 hour. The microplate was washed three times with phosphate buffer containing 0.1% Tween 20. The biotin-labeled monoclonal antibody prepared in Example <6-2> was diluted with a phosphate buffer containing 1% BSA and 0.1% Tween 20 and added (0.3 µl/50 µl/well) into the respective wells. The plate was incubated at room temperature for 1 hour.

The microplate was washed three times with phosphate buffer containing 0.1% Tween 20. A solution of streptavidin-β-galactosidase (50 µl; Gibco-BRL), diluted 1000 times with a solution (pH7.0) containing 20 mM HEPES, 0.5M NaCl and BSA (1 mg/ml), was added into each well. The plate was incubated at room temperature for 30 minutes.

The microplate was washed three times with phosphate buffer containing 0.1% Tween 20. A solution of 1% 4-Methyl-umbelliferyl-β-D-galactoside (50 µl; Sigma) in a phosphate buffer (10 mM, pH7.0, containing Na and K ions) containing 100 mM NaCl, 1 mM $MgCl_2$ and 1 mg/ml BSA, was added into each well. The plate was incubated at room temperature for 10 minutes.

1M $Na_2CO_3$ (100 µl) was added to each well to stop the reaction. The fluorescence intensity was measured by the FLUOROSCAN II MICROPLATE FLUOROMETER (Flow Laboratories Inc.) at a wavelength of 460 nm (excitation wavelength: 355 nm). The amount of mouse CTGF or rat CTGF in the sample were determined by using the calibration curve as prepared in the following example.

<6-4> Preparation of the Calibration Curve

The calibration curve was prepared by using the sandwich ELSA established in Example <6-3> in which the labeled CTGF standard used was the affinity-purified recombinant mouse CTGF or recombinant rat CTGF, which were prepared in Example <4-8>. The result is shown in FIG. 20.

The calibration curve for mouse CTGF was obtained with a significant difference even for an extremely low concentration range of 1 ng/ml to 1000 ng/ml. The calibration curve for rat CTGF was also obtained with a significant difference for a concentration range of 10 ng/ml to 1000 ng/ml. However, human CTGF was not measurable in the sandwich ELISA system established in Example <6-3>.

EXAMPLE 7

Assay of CTGF in the Sera from Patients Affected with Various Diseases

CTGF in the sera from patients affected with various diseases was assayed by the sandwich ELISA established in Example <5-3>.

<7-1> Biliary Atresia, Rheumatic Vasculitis, Malignant Rheumatoid Arthritis, Psoriasis, and Atopic Dermatitis Human sera used in this experiment were collected from normal healthy persons (33 samples), patients affected with biliary atresia and submitted to a surgical operation (post-operative sample; <Group 1> patients with normal clinical findings (17 samples); <Group 2> patients with progressing symptoms (14 samples); <Group 3> patients with severe symptoms in need of liver transplantation (8 samples)), patients with rheumatic vasculitis (10 samples), patient with malignant rheumatoid arthritis (MRA)(17 samples), patients with psoriasis (24 samples) and patients with atopic dermatitis (34 samples).

The results are shown in FIG. 21 (biliary atresia) and FIG. 22 (rheumatic vasculitis, malignant rheumatoid arthritis, psoriasis, and atopic dermatitis).

It was evidenced that, among patients affected with biliary atresia, CTGF was significantly expressed in Group 2 patients (with symptoms at progressive stage). In addition, as compared with normal healthy persons, patients affected with rheumatic vasculitis or malignant rheumatoid arthritis exhibited significantly higher expression of CTGF.

<7-2> Rheumatoid Arthritis and Osteoarthritis

Samples used in this experiment were synovial fluids collected from patients affected with rheumatoid arthritis (RA; 36 patients) and patients with osteoarthritis (OA; 19 patients). The result is shown in FIG. 23.

It was found that the synovial fluid CTGF levels of patients with rheumatoid arthritis were significantly higher than those of patients with osteoarthritis.

Based on this result, it can be stated that the expression of CTGF in patients with various diseases as well as normal healthy persons can be highly sensitively quantified by the assay system of the present invention and that the system can be utilized as a clinical diagnosis for accurate clinical judgment of the degree of illness.

EXAMPLE 8

Preparation of Antibody Fragments F(ab')$_2$ and Fab

The antibody fragments F(ab')$_2$ and Fab derived from various monoclonal antibodies prepared above, are prepared as follows.

A sodium acetate buffer (20 mM; pH3.5) containing monoclonal antibody (5 mg/ml) is incubated at 37° C. for 30 minutes. Insolubilized pepsin (1 ml; Pierce Chemical Co.) is added thereto. The mixture is then incubated at 37° C. for 12 hours while being shaken on a rotator. The reaction solution is centrifuged (3000 rpm, for 10 minutes) and the resulting supernatant is recovered.

Protein A-affinity chromatography is performed by using a Protein A column kit (Amersham) according to the supplier's protocol, as follows. A binding buffer is added to the precipitate obtained by centrifugation. The solution is centrifuged (3000 rpm, for 10 minutes) again, and then the resulting supernatant is recovered. The first and second supernatants obtained are combined together and an equal volume of the binding buffer is added thereto. The mixture is adjusted to pH 8.9 by adding 1N sodium hydroxide thereto. The mixed solution is loaded onto the Protein A column equilibrated with the binding buffer. Then the column is washed twice with the binding buffer (5 ml) to elute and collect the fraction of interest. The fraction is dialyzed with 5 mM phosphate buffer (2 L, pH6.8) (at 4° C., for 24 hours).

Further purification is performed by high performance liquid chromatography (HPLC) using hydroxyapatite column (BioRad). The sample solution after dialysis is loaded onto the hydroxyapatite column. 5 mM phosphate buffer is allowed to flow through the column for 15 minutes, the antibody fragments are eluted with a linear gradient of 5 mM–0.4M phosphate buffer. The eluate is collected on a fraction collector and the absorbance is monitored at a wavelength of 280 nm for the recovery of F(ab')$_2$-containing fractions. The fractions collected are dialyzed with 2L of phosphate buffer (at 4° C., for 24 hours). The purified F(ab')$_2$ of monoclonal antibody is thus obtained.

EXAMPLE 9

Preparation of Human-CTGF-expressing Transgenic Mouse

The human CTGF-encoding cDNA obtained in Example 2 was blunted by using a DNA blunting kit (Takara Shuzo Co.) and inserted into an expression vector, PCAGGS (Gene, Vol. 108, p. 193–200, 1991), containing chicken β-actin promoter to obtain the plasmid phCTGF. Human kidney-derived fibroblast cell line 293-T (ATCC CRL1573) was transformed by electroporation with phCTGF. It was verified that the transformant expressed and secreted human CTGF into the culture supernatant by the sandwich ELISA established in Example 5.

The plasmid phCTGF was linearized by the treatment with restriction enzyme for the subsequent preparation of transgenic mouse.

White ICR females with a copulatory plug were selected as foster mothers that were obtained by mating white ICR female mouse(Japan SLC) with a vasectomized white ICR male mouse(Japan SLC). Donor female mice giving fertilized eggs to be used for human CTGF gene transfer were prepared by mating a female BDF-1 mouse (Japan SLC), which were superovulated by the administration of PEAMEX (5 units; Sankyo Zohki Co.) and PREGNYL (5 units; Organon Co.), with a BDF-1 male mouse (Japan SLC). After the mating, the oviduct was removed from the BDF-1 mouse (female), and was hyaluronidase-treated to obtain only fertilized eggs. The eggs were stored in a medium.

The human CTGF gene was introduced into the fertilized eggs by using a manipulator under a microscope according to the usual method. Fertilized eggs were held-in-place with a holding needle. The above-mentioned linear human CTGF gene, which was dissolved in Tris-EDTA buffer, was microinjected into the male pronucleus of the egg with a DNA injection needle at 37° C.

After the gene transfer, only fertilized eggs with a normal appearance were selected. The eggs, to which the human CTGF was introduced, were transferred into the fimbria of the oviduct in the ovary of the mouse (white ICR mouse) used as a foster mother.

Genomic DNA was extracted form the tails of the resulting offspring (chimeric mice) born from the foster mother. The presence of the transferred human CTGF gene in mouse genome was confirmed by PCR. In addition, it was confirmed that human CTGF was expressed and secreted into blood serum of the mouse, by the sandwich ELISA established by Example 5. Then the chimeric mice were mated with normal mice to prepare heterozygous transgenic mice expressing human CTGF at high levels. The heterozygous mice were mated to each other to prepare homozygous transgenic mice.

EXAMPLE 11

Preparation of Rat CTGF

<11-1> cDNA Cloning (1) Preparation of Rat cDNA Library and Probe

Cells of rat kidney-derived fibroblast strain NRK-49F (ATCC CRL-1570; about $1 \times 10^6$ cells/ml) were centrifuged (at 4° C., 2,000×g, for 5 minutes). The cells precipitated were suspended in ISOGEN (Nippon Gene) and then chloroform was added thereto. After the mixture was shaken, the upper layer was recovered. Isopropanol was added to the obtained upper solution. The mixture was allowed to stand at room temperature for 10 minutes and centrifuged (at 4° C., 12,000×g, for 10 minutes) for RNA precipitation. After washing with ethanol, the precipitated RNA was dissolved in TE buffer. Poly(A)+ RNA was purified from the total RNA using an mRNA Purification Kit (Pharmacia).

Complementary DNA synthesis was performed by using the poly (A)+RNA (5 μg) as a template and a SUPER-SCRIPT 1 SYSTEM FOR cDNA SYNTHESIS KIT (GIBCO-BRL). An oligo dT primer with NotI site (GIBCO-BRL) was used for improved screening efficiency. After linking to a SalI adaptor, cDNA was digested with NotI to give unidirectional CDNA. The heterogeneous cDNA was fractionated by using a cDNA size fractionation column (GIBCO-BRL).

The nucleotide sequences of the human and mouse cDNAs obtained in Example 2 were compared to each other. A pair of 5' (SEQ ID NO: 3) and 3' (SEQ ID NO: 4) primers were designed and synthesized based on a highly homologous region shared by the human and mouse CTGF cDNAs.

PCR (polymerase chain reaction) amplification was performed by using the CDNA library prepared above as a template and by using the above-mentioned primers and Ex Taq DNA polymerase (Takara Shuzo Co.). The reaction was carried out on a DNA THERMAL CYCLER (Perkin Elmer Cetus). The final concentration of each primer was 0.4 μM and that of $Mg^{2+}$ was 1.5 mM. The cycling profile was 35 cycles of the following cycle: denaturing at 94° C. for 1 minute, annealing at 55° C. for 1 minute and extension at 72° C. for 1 minute. After electrophoresed on an agarose gel, the amplified DNA was purified by using a QUIAEX DNA extraction kit (QUIAGEN).

The recovered DNA fragment was ligated with a vector pCRII (Invitrogen Co.) by using the TA CLONING KIT (Invitrogen Co.). Nucleotide sequence of the resulting cDNA was sequenced on an A.L.F. DNA SEQUENCER (Pharmacia) by using an AUTO READ SEQUENCING KIT (Pharmacia) according to the dideoxy method. The nucleotide sequence of the cDNA fragment was compared with those of human and mouse CTGF cDNAs obtained in Examples 2 and 3. It was confirmed that the CDNA fragment contained the coding region for rat homologue (rat CTGF) corresponding to the human and mouse CTGF gene.

A probe for plaque hybridization was prepared by labeling the cDNA (about 0.8 kb) with FITC by using an ECL RANDOM PRIME LABELING KIT (Amersham).

(2) Ligation of CDNA to Vector and Packaging

The cDNA obtained above in (1) was ligated to a vector 1zipLox NotI-SalI arm (GIBCO-BRL). The ligation reaction was performed by using a DNA ligation Kit (Takara Shuzo Co.). The ligated DNA was packaged in vitro by using a GIGA PACK II GOLD (Stratagene). A cDNA library comprising recombinant phage-containing plaques was prepared with the obtained phage particles and *E. coli* host Y1090 strain (GIBCO-BRL).

(3) Screening of a CDNA Library

According to the plaque hybridization method described in "Molecular Cloning: A Laboratory Manual (Maniatis et al., Cold Spring Harbor Laboratory, Cold Spring Harbor, N.Y.)", screening of the CDNA library prepared above in (2) was carried out by using RAPID HYBRIDIZATION BUFFER (Amersham), as follows.

After the cDNA ($1 \times 10^4$ plaques) prepared above in (2) was seeded on agar plates, filter replicas were prepared with HYBOND-N-NYLON MEMBRANES (Amersham). Plaque hybridization was performed in the RAPID HYBRIDIZATION BUFFER (Amersham) by using the FITC-labeled probe prepared above in (1) and the replicas. The primary screening and the secondary screening yielded 13 positive clones. Each clone obtained by single-plaque isolation was treated by in vivo excision method according to the manual provided by the supplier GIBCO-BRL. Thirteen clones were obtained as plasmid DNAs.

(4) Determination of Nucleotide Sequence

Nucleotide sequence of the 13 cDNA cones were determined on an A.L.F. DNA SEQUENCER (Pharmacia) by using an AUTO READ SEQUENCING KIT (Pharmacia) according to the dideoxy method. All 13 clones shared the same nucleotide sequence. Comparison of the cDNA sequences with those of human and mouse CTGFs revealed that an obtained clone, r311, contained a full-length cDNA encoding rat CTGF. The full-length CDNA sequence (comprising the nucleotide sequence of the 5' end and the 3' end thereof) of rat CTGF is shown in SEQ ID NO: 1, and the deduced amino acid sequence thereof is shown in SEQ ID NO: 2.

<11-2> Preparation of Recombinant Rat CTGF

The clone r311 prepared in Example <11-1>, which contained a cDNA encoding rat CTGF, was digested with SalI and DraI, to obtain the fragment of rat CTGF-encoding cDNA. The DNA fragment was inserted into a plasmid pcDNA3.1 (−) (Invitrogen Co.) to prepare an expression vector. Human epithelioid cell line Hela cell (ATCC CCL-2) was transformed with the vector by electroporation. GENETICIN-resistant transformants were selected by culturing the transformed cells in an RPMI1640 medium containing GENETICIN (0.8 mg/ml; GIBCO-BRL) and 10% fetal calf serum for about two weeks. The selected transformants were cultured in a serum-free medium ASF104 (Ajinomoto Co. Inc.) for the expression of the recombinant rat CTGF. The expression of rat CTGF was confirmed by Western blotting using the monoclonal antibody, which was prepared above in Example 4, having the crossreactivity to rat CTGF.

The culture supernatant was recovered and treated by ammonium sulfate precipitation method. The precipitated proteins were fractionated by heparin-column chromatography. The column was washed with 0.3M NaCl/PBS, and then the protein fraction of interest was eluted with 0.5M NaCl/PBS. Thus, a fraction with partially purified rat CTGF was obtained.

Industrial Applicability

The present invention provides previously unavailable various monoclonal antibodies derived from a variety of mammals. The antibodies are reactive to CTGFs from a variety of mammals such humans, mice, rats and rabbits, and are different from one another in respect to the properties such as antigenic specificity, affinity for the antigen, neutralizing activity, and crossreactivity. Particularly, the present invention leads the way in the world in providing various human monoclonal antibodies against human CTGF by using, as an immune animal, the transgenic mouse prepared to produce human antibodies by recombinant technology.

Among the monoclonal antibodies of the present invention, the anti-human CTGF monoclonal antibody and the pharmaceutical composition thereof, suppress and inhibit the onset and advancement of various diseases which are believed to be caused by CTGF; such diseases include, for example, kidney diseases (kidney fibrosis, nephritis, and renal failure, etc.), lung diseases (for example, pulmonary fibrosis and pneumonia), liver diseases (for example, hepatic fibrosis, cirrhosis, and hepatitis), skin diseases (for example, injuries, scleroderma, psoriasis, and keloid), arthritis (for example, rheumatoid arthritis and osteoarthritis), and vascular diseases (for example, rheumatic vasculitis), tissue fibrosis developed as a complication in various cancers, and arteriosclerosis (specifically, tissue fibrosis which occurs as a complication). The anti-human CTGF monoclonal antibody and the pharmaceutical composition thereof are thus useful as pharmaceuticals for treating or preventing these diseases.

The utility value of the antibody as a pharmaceutical is dramatically elevated, because the human monoclonal antibodies and the pharmaceutical composition thereof are nonantigetic in humans, the antigenicity being a major therapeutic problem (side effect) in the treatment with antibody pharmaceuticals comprising antibodies derived from non-human mammals such as mice.

By using immunoassay with the monoclonal antibodies of the present invention, it is possible to provide various immunoassay systems (methods and kits) for conveniently and highly sensitively assaying intact CTGF in the body fluids (such as serum) from mammals (human, mouse, rat and rabbit). It is also possible to easily purify CTGFs of high purity from various mammals by using affinity column chromatography with an insoluble carrier on which the monoclonal antibody is immobilized.

Moreover, the inventive non-human transgenic mammal (transgenic mouse, etc.) expressing human CTGF is extremely useful as a tool for screening candidate pharmaceutical agents (low molecular weight compounds, antibodies, antisense nucleotides, and polypeptides except human CTGF) having the activity of regulating human CTGF functions (inhibition, suppression, activation, stimulation, etc.) as well as being useful as an animal model for studying physiological functions of human CTGF. Specifically, it is possible to assess the effect of such a pharmaceutical agent on human CTGF by administering the agent to the non-human transgenic mammal and assaying the levels of human CTGF expressed in the animal, by using the assay system (sandwich ELISA, etc.) of the present invention.

What is claimed is:

1. A non-human monoclonal antibody or a portion thereof selected from the group consisting of F(ab')2, Fab, Fab', Fv, sFv, dsFv and dAb, which (a) binds to human, mouse and rat connective tissue growth factors (CTGFs) and (b) has the IgG isotype.

2. The non-human monoclonal antibody or a portion thereof according to claim 1, wherein said antibody inhibits the binding of human CTGF to human kidney-derived fibroblast cell line 293-T (ATCC CRL 1573).

3. The non-human monoclonal antibody or a portion thereof according to claim 1, wherein said antibody is a mouse, rat or hamster antibody.

4. The non-human monoclonal antibody or a portion thereof according to claim 3, wherein said antibody inhibits the binding of human CTGF to human kidney-derived fibroblast cell line 293-T (ATCC CRL 1573).

5. A non-human monoclonal antibody which is produced by a hybridoma identified by international deposit accession numbers selected from the group consisting of FERM BP-6208 and FERM BP-6209.

6. A cell producing the non-human monoclonal antibody according to claim 1.

7. The cell according to claim 6, wherein said cell is a hybridoma obtained by fusing a mammalian myeloma cell with a mammalian B cell that produces the non-human monoclonal antibody.

8. A cell identified by international deposit accession numbers selected from the group consisting of FERM BP-6208 and FERM BP-6209.

9. An antibody-immobilized insoluble carrier comprising the non-human monoclonal antibody according to claim 1 or claim 5.

10. The non-human antibody-immobilized insoluble carrier according to claim 9, wherein said insoluble carrier is selected from the group consisting of plates, test tubes, tubes, beads, balls, filters and membranes.

11. The non-human antibody-immobilized insoluble carrier according to claim 9, wherein said insoluble carrier is a filter or membrane, for affinity column chromatography.

12. A labeled antibody comprising the non-human monoclonal antibody or a portion thereof according to claim 1 or the non-human monoclonal antibody according to claim 5 that is labeled with a labeling agent that provides a detectable signal.

13. The labeled non-human antibody according to claim 12, wherein said labeling agent is an enzyme, fluorescent substance, chemiluminescent substance, biotin, avidin, or radioisotope.

14. A kit for detecting or assaying mammalian CTGF, comprising the non-human monoclonal antibody or a portion thereof according to claim 1 or the non-human monoclonal antibody according to claim 5.

15. A kit for detecting or assaying mammalian CTGF comprising an antibody-immobilized insoluble carrier which comprises the non-human monoclonal antibody according to claim 1 or claim 5.

16. A kit for detecting or assaying mammalian CTGF comprising a labeled antibody which comprises the non-human monoclonal antibody or a portion thereof according to claim 1 or the non-human monoclonal antibody according to claim 5 that is labeled with a labeling agent that provides a detectable signal.

17. A kit for purifying mammalian CTGF, comprising an antibody-immobilized insoluble carrier which comprises the non-human monoclonal antibody according to claim 1 or claim 5.

* * * * *

SEQUENCE LISTING

```
<160> NUMBER OF SEQ ID NOS: 27

<210> SEQ ID NO 1
<211> LENGTH: 2338
<212> TYPE: DNA
<213> ORGANISM: Rat
<220> FEATURE:
<221> NAME/KEY: 5'UTR
<222> LOCATION: (1)..(212)
<221> NAME/KEY: CDS
<222> LOCATION: (213)..(1256)
<221> NAME/KEY: 3'UTR
<222> LOCATION: (1257)..(2338)
<221> NAME/KEY: polyA_signal
<222> LOCATION: (2297)..(2302)

<400> SEQUENCE: 1
ctccaagaag actcagccag acccactcca gctccgaccc taggagaccg acctcctcca      60
gacggcagca gccccagccc agtggacaac cccaggagcc accacctgga gcgtccggac     120
accaacctcc gccccgagac cgagtccagg ctccggccgc gcccctcgtc gcctctgcac     180
cccgctgtgc gtcctcctgc cgcgccccga cc atg ctc gcc tcc gtc gcg ggt      233
                                   Met Leu Ala Ser Val Ala Gly
                                    1               5 ccc gtt agc ctc gcc ttg gtg ctc ctc ctc tgc acc cgg cct gcc acc      281
Pro Val Ser Leu Ala Leu Val Leu Leu Leu Cys Thr Arg Pro Ala Thr
```

-continued

|  |  |  |  | 10 |  |  |  |  | 15 |  |  |  |  | 20 |  |  |
|---|---|---|---|---|---|---|---|---|---|---|---|---|---|---|---|---|
| ggc | cag | gac | tgc | agc | gcg | cag | tgt | cag | tgc | gca | cgt | gaa | gcg | gcg | ccg | 329 |
| Gly | Gln | Asp | Cys | Ser | Ala | Gln | Cys | Gln | Cys | Ala | Arg | Glu | Ala | Ala | Pro |  |
|  | 25 |  |  |  | 30 |  |  |  |  | 35 |  |  |  |  |  |  |
| cgc | tgc | ccc | gcc | ggc | gtg | agc | ctg | gtg | ctg | gac | ggc | tgc | ggc | tgc | tgc | 377 |
| Arg | Cys | Pro | Ala | Gly | Val | Ser | Leu | Val | Leu | Asp | Gly | Cys | Gly | Cys | Cys |  |
| 40 |  |  |  |  | 45 |  |  |  |  | 50 |  |  |  |  | 55 |  |
| cgc | gtc | tgc | gcc | aag | cag | ctg | gga | gaa | ctg | tgc | acg | gag | cgt | gat | ccc | 425 |
| Arg | Val | Cys | Ala | Lys | Gln | Leu | Gly | Glu | Leu | Cys | Thr | Glu | Arg | Asp | Pro |  |
|  |  |  |  | 60 |  |  |  |  | 65 |  |  |  |  | 70 |  |  |
| tgc | gac | cca | cac | aag | ggt | ctc | ttc | tgc | gac | ttc | ggc | tcc | ccc | gcc | aac | 473 |
| Cys | Asp | Pro | His | Lys | Gly | Leu | Phe | Cys | Asp | Phe | Gly | Ser | Pro | Ala | Asn |  |
|  |  |  | 75 |  |  |  |  | 80 |  |  |  |  | 85 |  |  |  |
| cgc | aag | att | ggc | gtg | tgc | cct | gcc | aaa | gat | ggt | gca | ccc | tgt | gtc | ttc | 521 |
| Arg | Lys | Ile | Gly | Val | Cys | Pro | Ala | Lys | Asp | Gly | Ala | Pro | Cys | Val | Phe |  |
|  |  | 90 |  |  |  |  | 95 |  |  |  |  | 100 |  |  |  |  |
| ggt | ggg | tcc | gtg | tac | cgc | agc | ggc | gag | tcc | ttc | caa | agc | agt | tgc | aaa | 569 |
| Gly | Gly | Ser | Val | Tyr | Arg | Ser | Gly | Glu | Ser | Phe | Gln | Ser | Ser | Cys | Lys |  |
|  | 105 |  |  |  |  | 110 |  |  |  |  | 115 |  |  |  |  |  |
| tac | cag | tgc | act | tgc | ctg | gat | ggg | gcc | gtg | ggc | tgt | gtg | ccc | ctg | tgc | 617 |
| Tyr | Gln | Cys | Thr | Cys | Leu | Asp | Gly | Ala | Val | Gly | Cys | Val | Pro | Leu | Cys |  |
| 120 |  |  |  |  | 125 |  |  |  |  | 130 |  |  |  |  | 135 |  |
| agc | atg | gac | gtg | cgc | ctg | ccc | agc | cct | gac | tgc | ccc | ttc | ccg | aga | agg | 665 |
| Ser | Met | Asp | Val | Arg | Leu | Pro | Ser | Pro | Asp | Cys | Pro | Phe | Pro | Arg | Arg |  |
|  |  |  | 140 |  |  |  |  | 145 |  |  |  |  | 150 |  |  |  |
| gtc | aag | ctg | ccc | ggg | aaa | tgc | tgt | gag | gag | tgg | gtg | tgt | gat | gag | ccc | 713 |
| Val | Lys | Leu | Pro | Gly | Lys | Cys | Cys | Glu | Glu | Trp | Val | Cys | Asp | Glu | Pro |  |
|  |  |  | 155 |  |  |  |  | 160 |  |  |  |  | 165 |  |  |  |
| aag | gac | cgc | aca | gtg | gtt | ggc | cct | gcc | cta | gct | gcc | tac | cga | ctg | gaa | 761 |
| Lys | Asp | Arg | Thr | Val | Val | Gly | Pro | Ala | Leu | Ala | Ala | Tyr | Arg | Leu | Glu |  |
|  |  | 170 |  |  |  |  | 175 |  |  |  |  | 180 |  |  |  |  |
| gac | aca | ttt | ggc | cct | gac | cca | act | atg | atg | cga | gcc | aac | tgc | ctg | gtc | 809 |
| Asp | Thr | Phe | Gly | Pro | Asp | Pro | Thr | Met | Met | Arg | Ala | Asn | Cys | Leu | Val |  |
|  | 185 |  |  |  |  | 190 |  |  |  |  | 195 |  |  |  |  |  |
| cag | acc | aca | gag | tgg | agc | gcc | tgt | tct | aag | acc | tgt | ggg | atg | ggc | atc | 857 |
| Gln | Thr | Thr | Glu | Trp | Ser | Ala | Cys | Ser | Lys | Thr | Cys | Gly | Met | Gly | Ile |  |
| 200 |  |  |  |  | 205 |  |  |  |  | 210 |  |  |  |  | 215 |  |
| tcc | acc | cgg | gtt | acc | aat | gac | aat | acc | ttc | tgc | agg | ctg | gag | aag | cag | 905 |
| Ser | Thr | Arg | Val | Thr | Asn | Asp | Asn | Thr | Phe | Cys | Arg | Leu | Glu | Lys | Gln |  |
|  |  |  |  | 220 |  |  |  |  | 225 |  |  |  |  | 230 |  |  |
| agt | cgt | ctc | tgc | atg | gtc | agg | ccc | tgt | gaa | gct | gac | cta | gag | gaa | aac | 953 |
| Ser | Arg | Leu | Cys | Met | Val | Arg | Pro | Cys | Glu | Ala | Asp | Leu | Glu | Glu | Asn |  |
|  |  | 235 |  |  |  |  | 240 |  |  |  |  | 245 |  |  |  |  |
| att | aag | aag | ggc | aaa | aag | tgc | atc | cgg | acg | cct | aaa | att | gcc | aag | cct | 1001 |
| Ile | Lys | Lys | Gly | Lys | Lys | Cys | Ile | Arg | Thr | Pro | Lys | Ile | Ala | Lys | Pro |  |
|  | 250 |  |  |  |  | 255 |  |  |  |  | 260 |  |  |  |  |  |
| gtc | aag | ttt | gag | ctt | tct | ggc | tgc | acc | agt | gtg | aag | acc | tac | cgg | gct | 1049 |
| Val | Lys | Phe | Glu | Leu | Ser | Gly | Cys | Thr | Ser | Val | Lys | Thr | Tyr | Arg | Ala |  |
|  | 265 |  |  |  |  | 270 |  |  |  |  | 275 |  |  |  |  |  |
| aag | ttc | tgt | ggg | gtg | tgc | acg | gac | ggc | cgc | tgc | tgc | aca | ccg | cac | aga | 1097 |
| Lys | Phe | Cys | Gly | Val | Cys | Thr | Asp | Gly | Arg | Cys | Cys | Thr | Pro | His | Arg |  |
| 280 |  |  |  |  | 285 |  |  |  |  | 290 |  |  |  |  | 295 |  |
| acc | acc | aca | ctg | ccg | gtg | gag | ttc | aag | tgc | ccc | gat | ggc | gag | atc | atg | 1145 |
| Thr | Thr | Thr | Leu | Pro | Val | Glu | Phe | Lys | Cys | Pro | Asp | Gly | Glu | Ile | Met |  |
|  |  |  |  | 300 |  |  |  |  | 305 |  |  |  |  | 310 |  |  |
| aaa | aag | aac | atg | atg | ttc | atc | aag | acc | tgt | gcc | tgc | cat | tac | aac | tgt | 1193 |
| Lys | Lys | Asn | Met | Met | Phe | Ile | Lys | Thr | Cys | Ala | Cys | His | Tyr | Asn | Cys |  |
|  |  |  |  | 315 |  |  |  |  | 320 |  |  |  |  | 325 |  |  |
| ccc | ggg | gac | aat | gac | atc | ttt | gag | tcc | ttg | tac | tac | agg | aag | atg | tat | 1241 |

```
Pro Gly Asp Asn Asp Ile Phe Glu Ser Leu Tyr Tyr Arg Lys Met Tyr
            330                 335                 340 gga gac atg gcg taa agccagggag taagggacac gaactcattt agactataac    1296
Gly Asp Met Ala
    345 ttgaactgag ttacatctca ttttcttctg taaaaaaaac aaaaagggtt acagtagcac   1356 attaatttaa atctgggttc ctaactgctg tgggagaaaa cacccaccg aagtgagaac    1416 cgtgtgtcat tgtcatgcaa atagcctgtc aatctcagac actggtttcg agacagttta   1476 gacttgacag ttgttcacta gcgcacagtg acagaacgca cactaaggtg agcctcctgg   1536 aagagtggag atgccaggag aaagacaggt actagctgag gtcatttttaa aagcagcgat  1596 atgcctactt tttggagtgt gacaggggag ggacattata gcttgcttgc agacagacct   1656 gctctagcaa gagctgggtg tgtgtcctcc actcggtgag gctgaagcca gctattcttt   1716 cagtaagaac agcagtttca gcgctgacat tctgattcca gygacactgg tcgggagtca   1776 gaaccttgtc tattagactg gacagcttgt ggcaagtgaa tttgccggta acaagccaga   1836 tttttatgga tcttgtaaat attgtggata aatatatata tttgtacagt tatctargtt   1896 aatttaaaga cgtttgtgcc tattgttctt gttttaagtg cttttggaat tttaaactg    1956 atagcctcaa actccaaaca ccatcgatag gacataaagc ttgtctgtga ttcaaaacaa   2016 aggagatact gcagtggaaa ctgtaacctg agtgactgtc tgtcagaaca tatggtacgt   2076 agacggtaaa gcaatggatc agaagtcaga tttctagtag gaaatgtaaa atcactgttg   2136 gcgaacaaat ggcctttatt aagaaatggc ttgctcaggg taactggtca gatttccacg   2196 aggaagtgtt tgctgcttct ttgactatga ctggtttggg aggcagttta tttgttgaga   2256 gtgtgaccaa aagttacatg tttgcacctt tctagttgaa aataaagtat atatattttt   2316 tatatgaaaa aaaaaaaaaa aa                                            2338

<210> SEQ ID NO 2
<211> LENGTH: 347
<212> TYPE: PRT
<213> ORGANISM: Rat

<400> SEQUENCE: 2

Met Leu Ala Ser Val Ala Gly Pro Val Ser Leu Ala Leu Val Leu Leu
  1               5                  10                  15

Leu Cys Thr Arg Pro Ala Thr Gly Gln Asp Cys Ser Ala Gln Cys Gln
             20                  25                  30

Cys Ala Arg Glu Ala Ala Pro Arg Cys Pro Ala Gly Val Ser Leu Val
         35                  40                  45

Leu Asp Gly Cys Gly Cys Cys Arg Val Cys Ala Lys Gln Leu Gly Glu
     50                  55                  60

Leu Cys Thr Glu Arg Asp Pro Cys Asp Pro His Lys Gly Leu Phe Cys
 65                  70                  75                  80

Asp Phe Gly Ser Pro Ala Asn Arg Lys Ile Gly Val Cys Pro Ala Lys
                 85                  90                  95

Asp Gly Ala Pro Cys Val Phe Gly Gly Ser Val Tyr Arg Ser Gly Glu
            100                 105                 110

Ser Phe Gln Ser Ser Cys Lys Tyr Gln Cys Thr Cys Leu Asp Gly Ala
        115                 120                 125

Val Gly Cys Val Pro Leu Cys Ser Met Asp Val Arg Leu Pro Ser Pro
    130                 135                 140

Asp Cys Pro Phe Pro Arg Arg Val Lys Leu Pro Gly Lys Cys Cys Glu
```

```
                145                 150                 155                 160
Glu Trp Val Cys Asp Glu Pro Lys Asp Arg Thr Val Val Gly Pro Ala
                    165                 170                 175

Leu Ala Ala Tyr Arg Leu Glu Asp Thr Phe Gly Pro Asp Pro Thr Met
                    180                 185                 190

Met Arg Ala Asn Cys Leu Val Gln Thr Thr Glu Trp Ser Ala Cys Ser
            195                 200                 205

Lys Thr Cys Gly Met Gly Ile Ser Thr Arg Val Thr Asn Asp Asn Thr
    210                 215                 220

Phe Cys Arg Leu Glu Lys Gln Ser Arg Leu Cys Met Val Arg Pro Cys
225                 230                 235                 240

Glu Ala Asp Leu Glu Glu Asn Ile Lys Lys Gly Lys Lys Cys Ile Arg
                    245                 250                 255

Thr Pro Lys Ile Ala Lys Pro Val Lys Phe Glu Leu Ser Gly Cys Thr
                    260                 265                 270

Ser Val Lys Thr Tyr Arg Ala Lys Phe Cys Gly Val Cys Thr Asp Gly
            275                 280                 285

Arg Cys Cys Thr Pro His Arg Thr Thr Thr Leu Pro Val Glu Phe Lys
    290                 295                 300

Cys Pro Asp Gly Glu Ile Met Lys Lys Asn Met Met Phe Ile Lys Thr
305                 310                 315                 320

Cys Ala Cys His Tyr Asn Cys Pro Gly Asp Asn Asp Ile Phe Glu Ser
                    325                 330                 335

Leu Tyr Tyr Arg Lys Met Tyr Gly Asp Met Ala
                    340                 345

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:
      Artificially synthesized primer sequence
<221> NAME/KEY: primer_bind
<222> LOCATION: (1)..(20)

<400> SEQUENCE: 3
tgcggctgct gccgcgtctg                                                20

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence:
      Artificially synthesized primer sequence
<221> NAME/KEY: primer_bind
<222> LOCATION: (1)..(21)

<400> SEQUENCE: 4
gcacaggtct tgatgaacat c                                              21

<210> SEQ ID NO 5
<211> LENGTH: 444
<212> TYPE: DNA
<213> ORGANISM: Homo sapiens
<220> FEATURE:
<221> NAME/KEY: CDS
<222> LOCATION: (1)..(444)
<221> NAME/KEY: sig_peptide
<222> LOCATION: (1)..(57)
<221> NAME/KEY: V_region
```

-continued

```
<222> LOCATION: (58)..(363)

<400> SEQUENCE: 5 atg gag ttt ggg ctg agc tgg att ttc ctt gct gct att tta aaa ggt      48
Met Glu Phe Gly Leu Ser Trp Ile Phe Leu Ala Ala Ile Leu Lys Gly
1               5                   10                  15 gtc cag tgt gag gtg cag ctg gtg gag tct ggg gga ggc ttg gta aag      96
Val Gln Cys Glu Val Gln Leu Val Glu Ser Gly Gly Gly Leu Val Lys
            20                  25                  30 cct ggg ggg tcc ctt aag acc tct cct gtg cag cct ctg gat tca act     144
Pro Gly Gly Ser Leu Lys Thr Ser Pro Val Gln Pro Leu Asp Ser Thr
        35                  40                  45 ttc agt aac gcc tgg atg agc tgg gtc cgc cag gct cca gga agg ggc     192
Phe Ser Asn Ala Trp Met Ser Trp Val Arg Gln Ala Pro Gly Arg Gly
    50                  55                  60 tgg agt ggg ttg gcc gta tta aaa gca aaa ctg atg gtg gga cac aca     240
Trp Ser Gly Leu Ala Val Leu Lys Ala Lys Leu Met Val Gly His Thr
65                  70                  75                  80 gac tac gct gca ccc gtg aaa ggc aga ttc acc atc tca aga gat gat     288
Asp Tyr Ala Ala Pro Val Lys Gly Arg Phe Thr Ile Ser Arg Asp Asp
                85                  90                  95 tca aaa aac acg ctg tat ctg caa atg aac agc ctg aaa acc gag gac     336
Ser Lys Asn Thr Leu Tyr Leu Gln Met Asn Ser Leu Lys Thr Glu Asp
            100                 105                 110 aca gcc gtg tat tac tgt acc aca aaa tgg gtg gct acg gac tac ttt     384
Thr Ala Val Tyr Tyr Cys Thr Thr Lys Trp Val Ala Thr Asp Tyr Phe
        115                 120                 125 gac tac tgg ggc cag gga acc ctg gtc acc gtc tcc tca gcc tcc acc     432
Asp Tyr Trp Gly Gln Gly Thr Leu Val Thr Val Ser Ser Ala Ser Thr
    130                 135                 140 aag ggc cca tcg                                                     444
Lys Gly Pro Ser
145

<210> SEQ ID NO 6
<211> LENGTH: 148
<212> TYPE: PRT
<213> ORGANISM: Homo sapiens

<400> SEQUENCE: 6

Met Glu Phe Gly Leu Ser Trp Ile Phe Leu Ala Ala Ile Leu Lys Gly
1               5                   10                  15

Val Gln Cys Glu Val Gln Leu Val Glu Ser Gly Gly Gly Leu Val Lys
            20                  25                  30

Pro Gly Gly Ser Leu Lys Thr Ser Pro Val Gln Pro Leu Asp Ser Thr
        35                  40                  45

Phe Ser Asn Ala Trp Met Ser Trp Val Arg Gln Ala Pro Gly Arg Gly
    50                  55                  60

Trp Ser Gly Leu Ala Val Leu Lys Ala Lys Leu Met Val Gly His Thr
65                  70                  75                  80

Asp Tyr Ala Ala Pro Val Lys Gly Arg Phe Thr Ile Ser Arg Asp Asp
                85                  90                  95

Ser Lys Asn Thr Leu Tyr Leu Gln Met Asn Ser Leu Lys Thr Glu Asp
            100                 105                 110

Thr Ala Val Tyr Tyr Cys Thr Thr Lys Trp Val Ala Thr Asp Tyr Phe
        115                 120                 125

Asp Tyr Trp Gly Gln Gly Thr Leu Val Thr Val Ser Ser Ala Ser Thr
    130                 135                 140
```

```
Lys Gly Pro Ser
145

<210> SEQ ID NO 7
<211> LENGTH: 447
<212> TYPE: DNA
<213> ORGANISM: Homo sapiens
<220> FEATURE:
<221> NAME/KEY: CDS
<222> LOCATION: (1)..(447)
<221> NAME/KEY: sig_peptide
<222> LOCATION: (1)..(57)
<221> NAME/KEY: V_region
<222> LOCATION: (58)..(357)

<400> SEQUENCE: 7 atg gac tgg acc tgg agg atc tct ttc ttg gtg gca gca gcc aca gga      48
Met Asp Trp Thr Trp Arg Ile Ser Phe Leu Val Ala Ala Ala Thr Gly
  1               5                  10                  15 gcc cac tcc cag gtg cag ctg gtg cag tct ggg gct gag gtg aag aag      96
Ala His Ser Gln Val Gln Leu Val Gln Ser Gly Ala Glu Val Lys Lys
             20                  25                  30 cct ggg gcc tca gtg aag gtc tcc tgc aag gct ttc tgg cta cac ctt     144
Pro Gly Ala Ser Val Lys Val Ser Cys Lys Ala Phe Trp Leu His Leu
         35                  40                  45 tca ccc ggc tac tat atg cac tgg gtg cga cag gcc cct gga caa ggg     192
Ser Pro Gly Tyr Tyr Met His Trp Val Arg Gln Ala Pro Gly Gln Gly
     50                  55                  60 ctt gag tgg atg gga tgg atc aac cct aac agt agt ggc aca cac tat     240
Leu Glu Trp Met Gly Trp Ile Asn Pro Asn Ser Ser Gly Thr His Tyr
 65                  70                  75                  80 gca cag atg ttt cag ggc agg gtc acc gtg acc agg gac acg tcc atc     288
Ala Gln Met Phe Gln Gly Arg Val Thr Val Thr Arg Asp Thr Ser Ile
                 85                  90                  95 agc aca gcc tac atg gag ctg agc agg ctg aga tct gac gac acg gcc     336
Ser Thr Ala Tyr Met Glu Leu Ser Arg Leu Arg Ser Asp Asp Thr Ala
            100                 105                 110 gtg tat tac tgt gcg aga gag ggg ata gca gca gct gcc atc tac ggt     384
Val Tyr Tyr Cys Ala Arg Glu Gly Ile Ala Ala Ala Ala Ile Tyr Gly
        115                 120                 125 atg gac gtc tgg ggc caa ggg acc acg gtc acc gtc tcc tca gcc tcc     432
Met Asp Val Trp Gly Gln Gly Thr Thr Val Thr Val Ser Ser Ala Ser
    130                 135                 140 acc aag ggc cca tcg                                                  447
Thr Lys Gly Pro Ser
145

<210> SEQ ID NO 8
<211> LENGTH: 149
<212> TYPE: PRT
<213> ORGANISM: Homo sapiens

<400> SEQUENCE: 8

Met Asp Trp Thr Trp Arg Ile Ser Phe Leu Val Ala Ala Ala Thr Gly
  1               5                  10                  15

Ala His Ser Gln Val Gln Leu Val Gln Ser Gly Ala Glu Val Lys Lys
             20                  25                  30

Pro Gly Ala Ser Val Lys Val Ser Cys Lys Ala Phe Trp Leu His Leu
         35                  40                  45

Ser Pro Gly Tyr Tyr Met His Trp Val Arg Gln Ala Pro Gly Gln Gly
     50                  55                  60

Leu Glu Trp Met Gly Trp Ile Asn Pro Asn Ser Ser Gly Thr His Tyr
```

```
                65                  70                  75                  80
            Ala Gln Met Phe Gln Gly Arg Val Thr Val Thr Arg Asp Thr Ser Ile
                            85                  90                  95

Ser Thr Ala Tyr Met Glu Leu Ser Arg Leu Arg Ser Asp Asp Thr Ala
                        100                 105                 110

Val Tyr Tyr Cys Ala Arg Glu Gly Ile Ala Ala Ala Ile Tyr Gly
                    115                 120                 125

Met Asp Val Trp Gly Gln Gly Thr Thr Val Thr Val Ser Ser Ala Ser
                130                 135                 140

Thr Lys Gly Pro Ser
            145

<210> SEQ ID NO 9
<211> LENGTH: 438
<212> TYPE: DNA
<213> ORGANISM: Homo sapiens
<220> FEATURE:
<221> NAME/KEY: CDS
<222> LOCATION: (1)..(438)
<221> NAME/KEY: sig_peptide
<222> LOCATION: (1)..(57)
<221> NAME/KEY: V_region
<222> LOCATION: (58)..(350)

<400> SEQUENCE: 9 atg gac tgc acc tgg agg atc ctc ttc ttg gtg gca gca gct aca ggc       48
Met Asp Cys Thr Trp Arg Ile Leu Phe Leu Val Ala Ala Ala Thr Gly
 1               5                  10                  15 acc cac gcc cag gtc cag ctg gta cag ttt ggg gct gag gtg aag aag       96
Thr His Ala Gln Val Gln Leu Val Gln Phe Gly Ala Glu Val Lys Lys
                20                  25                  30 cct ggg gcc tca gtg aag gtc tcc tgc aag gtt tcc gga tac acc ctc      144
Pro Gly Ala Ser Val Lys Val Ser Cys Lys Val Ser Gly Tyr Thr Leu
            35                  40                  45 act gaa tta tcc atg cac tgg gtg cga cag gct cct gga aaa ggg ctt      192
Thr Glu Leu Ser Met His Trp Val Arg Gln Ala Pro Gly Lys Gly Leu
        50                  55                  60 gag tgg atg gga agt ttt gat cct gaa gat ggt gaa aca atc tac gca      240
Glu Trp Met Gly Ser Phe Asp Pro Glu Asp Gly Glu Thr Ile Tyr Ala
 65                  70                  75                  80 cag aag ttc cag ggc aga gtc acc atg acc gag gac aca tct aca gac      288
Gln Lys Phe Gln Gly Arg Val Thr Met Thr Glu Asp Thr Ser Thr Asp
                85                  90                  95 aca gcc tac atg gag ctg agc agc ctg aga tct gag gac acg gcc gtg      336
Thr Ala Tyr Met Glu Leu Ser Ser Leu Arg Ser Glu Asp Thr Ala Val
               100                 105                 110 tat tac tgt gca acc tct acg gtg gta act ccg tgg tac ttt gac tac      384
Tyr Tyr Cys Ala Thr Ser Thr Val Val Thr Pro Trp Tyr Phe Asp Tyr
           115                 120                 125 tgg ggc cag gga acc ctg gtc acc gtc tcc tca gcc tcc acc aag ggc      432
Trp Gly Gln Gly Thr Leu Val Thr Val Ser Ser Ala Ser Thr Lys Gly
       130                 135                 140 cca tcg                                                              438
Pro Ser
145

<210> SEQ ID NO 10
<211> LENGTH: 146
<212> TYPE: PRT
<213> ORGANISM: Homo sapiens

<400> SEQUENCE: 10
```

```
Met Asp Cys Thr Trp Arg Ile Phe Leu Val Ala Ala Thr Gly
 1               5                  10                  15

Thr His Ala Gln Val Gln Leu Val Gln Phe Gly Ala Glu Val Lys Lys
                20                  25                  30

Pro Gly Ala Ser Val Lys Val Ser Cys Lys Val Ser Gly Tyr Thr Leu
            35                  40                  45

Thr Glu Leu Ser Met His Trp Val Arg Gln Ala Pro Gly Lys Gly Leu
        50                  55                  60

Glu Trp Met Gly Ser Phe Asp Pro Glu Asp Gly Glu Thr Ile Tyr Ala
65                  70                  75                  80

Gln Lys Phe Gln Gly Arg Val Thr Met Thr Glu Asp Thr Ser Thr Asp
                85                  90                  95

Thr Ala Tyr Met Glu Leu Ser Ser Leu Arg Ser Glu Asp Thr Ala Val
                100                 105                 110

Tyr Tyr Cys Ala Thr Ser Thr Val Val Thr Pro Trp Tyr Phe Asp Tyr
                115                 120                 125

Trp Gly Gln Gly Thr Leu Val Thr Val Ser Ser Ala Ser Thr Lys Gly
        130                 135                 140

Pro Ser
145
```

<210> SEQ ID NO 11
<211> LENGTH: 438
<212> TYPE: DNA
<213> ORGANISM: Homo sapiens
<220> FEATURE:
<221> NAME/KEY: CDS
<222> LOCATION: (1)..(438)
<221> NAME/KEY: sig_peptide
<222> LOCATION: (1)..(57)
<221> NAME/KEY: V_region
<222> LOCATION: (58)..(350)

<400> SEQUENCE: 11

```
atg gac tgc acc tgg agg atc ttc ttc ttg gtg gca gca gct aca ggc      48
Met Asp Cys Thr Trp Arg Ile Phe Phe Leu Val Ala Ala Ala Thr Gly
 1               5                  10                  15 acc cac gcc cag gtc cag ctg gta cag tct ggg gct gag gtg aag aag      96
Thr His Ala Gln Val Gln Leu Val Gln Ser Gly Ala Glu Val Lys Lys
                20                  25                  30 cct ggg gcc tca gtg aag gtc tcc tgc aag gtt tcc gga tac acc ctc     144
Pro Gly Ala Ser Val Lys Val Ser Cys Lys Val Ser Gly Tyr Thr Leu
            35                  40                  45 act gaa tta tcc atg cac tgg gtg cga cag gct cct gga aaa ggg ctt     192
Thr Glu Leu Ser Met His Trp Val Arg Gln Ala Pro Gly Lys Gly Leu
        50                  55                  60 gag tgg atg gga agt ttt gat cct gaa gat ggt gaa aca atc tac gca     240
Glu Trp Met Gly Ser Phe Asp Pro Glu Asp Gly Glu Thr Ile Tyr Ala
65                  70                  75                  80 cag aag ttc cag ggc aga gtc acc atg acc gag gac aca tct aca gac     288
Gln Lys Phe Gln Gly Arg Val Thr Met Thr Glu Asp Thr Ser Thr Asp
                85                  90                  95 aca gcc tac atg gag ctg agc agc ctg aga tct gag gac acg gcc gtg     336
Thr Ala Tyr Met Glu Leu Ser Ser Leu Arg Ser Glu Asp Thr Ala Val
                100                 105                 110 tat tac tgt gca acc tct acg gtg gta act ccg tgg tac ttt gac tac     384
Tyr Tyr Cys Ala Thr Ser Thr Val Val Thr Pro Trp Tyr Phe Asp Tyr
                115                 120                 125 tgg ggc cag gga acc ctg gtc acc gtc tcc tca gcc tcc acc aag ggc     432
```

```
Trp Gly Gln Gly Thr Leu Val Thr Val Ser Ser Ala Ser Thr Lys Gly
    130                 135                 140 cca tcg                                                                    438
Pro Ser
145

<210> SEQ ID NO 12
<211> LENGTH: 146
<212> TYPE: PRT
<213> ORGANISM: Homo sapiens

<400> SEQUENCE: 12

Met Asp Cys Thr Trp Arg Ile Phe Phe Leu Val Ala Ala Ala Thr Gly
1               5                   10                  15

Thr His Ala Gln Val Gln Leu Val Gln Ser Gly Ala Glu Val Lys Lys
            20                  25                  30

Pro Gly Ala Ser Val Lys Val Ser Cys Lys Val Ser Gly Tyr Thr Leu
        35                  40                  45

Thr Glu Leu Ser Met His Trp Val Arg Gln Ala Pro Gly Lys Gly Leu
    50                  55                  60

Glu Trp Met Gly Ser Phe Asp Pro Glu Asp Gly Glu Thr Ile Tyr Ala
65                  70                  75                  80

Gln Lys Phe Gln Gly Arg Val Thr Met Thr Glu Asp Thr Ser Thr Asp
                85                  90                  95

Thr Ala Tyr Met Glu Leu Ser Ser Leu Arg Ser Glu Asp Thr Ala Val
            100                 105                 110

Tyr Tyr Cys Ala Thr Ser Thr Val Val Thr Pro Trp Tyr Phe Asp Tyr
        115                 120                 125

Trp Gly Gln Gly Thr Leu Val Thr Val Ser Ser Ala Ser Thr Lys Gly
    130                 135                 140

Pro Ser
145

<210> SEQ ID NO 13
<211> LENGTH: 450
<212> TYPE: DNA
<213> ORGANISM: Homo sapiens
<220> FEATURE:
<221> NAME/KEY: CDS
<222> LOCATION: (1)..(450)
<221> NAME/KEY: sig_peptide
<222> LOCATION: (1)..(58)
<221> NAME/KEY: V_region
<222> LOCATION: (59)..(353)

<400> SEQUENCE: 13 atg aaa cac ctg tgg ttc ttc ctt cct gct ggt ggc agc tcc cag atg      48
Met Lys His Leu Trp Phe Phe Leu Pro Ala Gly Gly Ser Ser Gln Met
1               5                   10                  15 ggt cct gtc cca ggt gca gct gca gga gtc ggg ccc agg act ggt gaa      96
Gly Pro Val Pro Gly Ala Ala Ala Gly Val Gly Pro Arg Thr Gly Glu
            20                  25                  30 gcc ttc aca gac cct gtc ctc acc tgc act gtc tct ggt ggc tcc atc     144
Ala Phe Thr Asp Pro Val Leu Thr Cys Thr Val Ser Gly Gly Ser Ile
        35                  40                  45 agc agt ggt ggt tac tac tgg agc tgg atc cgc cag cac cca ggg aag     192
Ser Ser Gly Gly Tyr Tyr Trp Ser Trp Ile Arg Gln His Pro Gly Lys
    50                  55                  60 ggc ctg gag tgg att ggg tac atc tat tac agt ggg agc acc tac tac     240
Gly Leu Glu Trp Ile Gly Tyr Ile Tyr Tyr Ser Gly Ser Thr Tyr Tyr
65                  70                  75                  80
```

```
aac ccg tcc ctc aag agt cga gtt acc ata tca gta gac acg tct aag    288
Asn Pro Ser Leu Lys Ser Arg Val Thr Ile Ser Val Asp Thr Ser Lys
                85                  90                  95 aac cag ttc tcc ctg aag ctg agc tct gtg act gcc gcg gac acg gcc    336
Asn Gln Phe Ser Leu Lys Leu Ser Ser Val Thr Ala Ala Asp Thr Ala
            100                 105                 110 gtg tat tac tgt gcg agc tat tac tat gat agt ggt ggt tat tac gac    384
Val Tyr Tyr Cys Ala Ser Tyr Tyr Tyr Asp Ser Gly Gly Tyr Tyr Asp
            115                 120                 125 tac ttt gac tac tgg ggc cag gga acc ctg gtc acc gtc tcc tca gcc    432
Tyr Phe Asp Tyr Trp Gly Gln Gly Thr Leu Val Thr Val Ser Ser Ala
        130                 135                 140 tcc acc aag ggc cca tcg                                            450
Ser Thr Lys Gly Pro Ser
145                 150

<210> SEQ ID NO 14
<211> LENGTH: 150
<212> TYPE: PRT
<213> ORGANISM: Homo sapiens

<400> SEQUENCE: 14

Met Lys His Leu Trp Phe Phe Leu Pro Ala Gly Gly Ser Ser Gln Met
 1               5                  10                  15

Gly Pro Val Pro Gly Ala Ala Gly Val Gly Pro Arg Thr Gly Glu
            20                  25                  30

Ala Phe Thr Asp Pro Val Leu Thr Cys Thr Val Ser Gly Gly Ser Ile
            35                  40                  45

Ser Ser Gly Gly Tyr Tyr Trp Ser Trp Ile Arg Gln His Pro Gly Lys
 50                  55                  60

Gly Leu Glu Trp Ile Gly Tyr Ile Tyr Tyr Ser Gly Ser Thr Tyr Tyr
 65                  70                  75                  80

Asn Pro Ser Leu Lys Ser Arg Val Thr Ile Ser Val Asp Thr Ser Lys
                85                  90                  95

Asn Gln Phe Ser Leu Lys Leu Ser Ser Val Thr Ala Ala Asp Thr Ala
            100                 105                 110

Val Tyr Tyr Cys Ala Ser Tyr Tyr Tyr Asp Ser Gly Gly Tyr Tyr Asp
            115                 120                 125

Tyr Phe Asp Tyr Trp Gly Gln Gly Thr Leu Val Thr Val Ser Ser Ala
        130                 135                 140

Ser Thr Lys Gly Pro Ser
145                 150

<210> SEQ ID NO 15
<211> LENGTH: 423
<212> TYPE: DNA
<213> ORGANISM: Homo sapiens
<220> FEATURE:
<221> NAME/KEY: CDS
<222> LOCATION: (1)..(423)
<221> NAME/KEY: sig_peptide
<222> LOCATION: (1)..(60)
<221> NAME/KEY: V_region
<222> LOCATION: (61)..(365)

<400> SEQUENCE: 15 atg gtg ttg cag acc cag gtc ttc att tct ctg ttg ctc tgg atc tct    48
Met Val Leu Gln Thr Gln Val Phe Ile Ser Leu Leu Leu Trp Ile Ser
 1               5                  10                  15 ggt gcc tac ggg gac atc gtg atg acc cag tct cca gac tcc ctg gct    96
```

```

Gly Ala Tyr Gly Asp Ile Val Met Thr Gln Ser Pro Asp Ser Leu Ala
            20                  25                  30 gtg tct ctg ggc gag agg gcc acc atc aac tgc aag tcc agc cag act       144
Val Ser Leu Gly Glu Arg Ala Thr Ile Asn Cys Lys Ser Ser Gln Thr
        35                  40                  45 gtt tta tac agc tcc aac aat aag aac tac tta gct tgg tac cag cag       192
Val Leu Tyr Ser Ser Asn Asn Lys Asn Tyr Leu Ala Trp Tyr Gln Gln
    50                  55                  60 aaa cca gga cag cct cct aag ctg ctc att tac tgg gca tct acc cgg       240
Lys Pro Gly Gln Pro Pro Lys Leu Leu Ile Tyr Trp Ala Ser Thr Arg
65                  70                  75                  80 gaa tcc ggg gtc cct gac cga ttc agt ggc agc ggg tct ggg aca gat       288
Glu Ser Gly Val Pro Asp Arg Phe Ser Gly Ser Gly Ser Gly Thr Asp
                85                  90                  95 ttc act ctc acc atc agc agc ctg cag gct gac gat gtg gca gtt tat       336
Phe Thr Leu Thr Ile Ser Ser Leu Gln Ala Asp Asp Val Ala Val Tyr
            100                 105                 110 tac tgt cag caa tat tat agt act cct ccg tgg acg ttc ggc caa ggg       384
Tyr Cys Gln Gln Tyr Tyr Ser Thr Pro Pro Trp Thr Phe Gly Gln Gly
        115                 120                 125 acc aag gtg gaa atc aaa cga act gtg gct gca cca tct                   423
Thr Lys Val Glu Ile Lys Arg Thr Val Ala Ala Pro Ser
    130                 135                 140

<210> SEQ ID NO 16
<211> LENGTH: 141
<212> TYPE: PRT
<213> ORGANISM: Homo sapiens

<400> SEQUENCE: 16

Met Val Leu Gln Thr Gln Val Phe Ile Ser Leu Leu Leu Trp Ile Ser
1               5                   10                  15

Gly Ala Tyr Gly Asp Ile Val Met Thr Gln Ser Pro Asp Ser Leu Ala
            20                  25                  30

Val Ser Leu Gly Glu Arg Ala Thr Ile Asn Cys Lys Ser Ser Gln Thr
        35                  40                  45

Val Leu Tyr Ser Ser Asn Asn Lys Asn Tyr Leu Ala Trp Tyr Gln Gln
    50                  55                  60

Lys Pro Gly Gln Pro Pro Lys Leu Leu Ile Tyr Trp Ala Ser Thr Arg
65                  70                  75                  80

Glu Ser Gly Val Pro Asp Arg Phe Ser Gly Ser Gly Ser Gly Thr Asp
                85                  90                  95

Phe Thr Leu Thr Ile Ser Ser Leu Gln Ala Asp Asp Val Ala Val Tyr
            100                 105                 110

Tyr Cys Gln Gln Tyr Tyr Ser Thr Pro Pro Trp Thr Phe Gly Gln Gly
        115                 120                 125

Thr Lys Val Glu Ile Lys Arg Thr Val Ala Ala Pro Ser
    130                 135                 140

<210> SEQ ID NO 17
<211> LENGTH: 420
<212> TYPE: DNA
<213> ORGANISM: Homo sapiens
<220> FEATURE:
<221> NAME/KEY: CDS
<222> LOCATION: (1)..(420)
<221> NAME/KEY: sig_peptide
<222> LOCATION: (1)..(60)
<221> NAME/KEY: V_region
<222> LOCATION: (61)..(364)
```

```
<400> SEQUENCE: 17 atg aag gat ctg ctc agc ttc ctg ggg ctg cta atg ctc tgg ata cct        48
Met Lys Asp Leu Leu Ser Phe Leu Gly Leu Leu Met Leu Trp Ile Pro
 1               5                  10                  15 gga tcc agt gca gat att gtc atg acc cag acg cca ctc ttc tgt ccg        96
Gly Ser Ser Ala Asp Ile Val Met Thr Gln Thr Pro Leu Phe Cys Pro
            20                  25                  30 tca ccc ctg gac agc cga gcc tcc atc tcc tgc aag tct ggt ctg agc       144
Ser Pro Leu Asp Ser Arg Ala Ser Ile Ser Cys Lys Ser Gly Leu Ser
 35                  40                  45 ctc ctg cac agt gat gga aag acc tat ttg cat tgg tac ctg cag aag       192
Leu Leu His Ser Asp Gly Lys Thr Tyr Leu His Trp Tyr Leu Gln Lys
     50                  55                  60 cca ggc cag cct cca cag ctc ctg atc tat gag agt ttc caa ccg gtt       240
Pro Gly Gln Pro Pro Gln Leu Leu Ile Tyr Glu Ser Phe Gln Pro Val
 65                  70                  75                  80 ctc ctg gag tgc cag ata ggc tca gtg gca gcg ggt cag gac aga ttt       288
Leu Leu Glu Cys Gln Ile Gly Ser Val Ala Ala Gly Gln Asp Arg Phe
                 85                  90                  95 cac act gaa aat cag ccg ggt gga agg ctg agg aat gtt ggg gtt tat       336
His Thr Glu Asn Gln Pro Gly Gly Arg Leu Arg Asn Val Gly Val Tyr
            100                 105                 110 tac tgc atg caa agt tta cag ctt ccg ctc act ttc ggc gga ggg acc       384
Tyr Cys Met Gln Ser Leu Gln Leu Pro Leu Thr Phe Gly Gly Gly Thr
        115                 120                 125 aag gtg gag atc aaa cga act gtg gct gca cca tct                       420
Lys Val Glu Ile Lys Arg Thr Val Ala Ala Pro Ser
130                 135                 140

<210> SEQ ID NO 18
<211> LENGTH: 140
<212> TYPE: PRT
<213> ORGANISM: Homo sapiens

<400> SEQUENCE: 18

Met Lys Asp Leu Leu Ser Phe Leu Gly Leu Leu Met Leu Trp Ile Pro
 1               5                  10                  15

Gly Ser Ser Ala Asp Ile Val Met Thr Gln Thr Pro Leu Phe Cys Pro
            20                  25                  30

Ser Pro Leu Asp Ser Arg Ala Ser Ile Ser Cys Lys Ser Gly Leu Ser
 35                  40                  45

Leu Leu His Ser Asp Gly Lys Thr Tyr Leu His Trp Tyr Leu Gln Lys
     50                  55                  60

Pro Gly Gln Pro Pro Gln Leu Leu Ile Tyr Glu Ser Phe Gln Pro Val
 65                  70                  75                  80

Leu Leu Glu Cys Gln Ile Gly Ser Val Ala Ala Gly Gln Asp Arg Phe
                 85                  90                  95

His Thr Glu Asn Gln Pro Gly Gly Arg Leu Arg Asn Val Gly Val Tyr
            100                 105                 110

Tyr Cys Met Gln Ser Leu Gln Leu Pro Leu Thr Phe Gly Gly Gly Thr
        115                 120                 125

Lys Val Glu Ile Lys Arg Thr Val Ala Ala Pro Ser
130                 135                 140

<210> SEQ ID NO 19
<211> LENGTH: 405
<212> TYPE: DNA
<213> ORGANISM: Homo sapiens
<220> FEATURE:
```

```
<221> NAME/KEY: CDS
<222> LOCATION: (1)..(405)
<221> NAME/KEY: sig_peptide
<222> LOCATION: (1)..(66)
<221> NAME/KEY: V_region
<222> LOCATION: (67)..(353)

<400> SEQUENCE: 19 atg gac atg agg gtc cct gct cag ctc ctg ggg ctc ctg ctg ctc tgg      48
Met Asp Met Arg Val Pro Ala Gln Leu Leu Gly Leu Leu Leu Leu Trp
 1               5                  10                  15 ctc tca ggt gcc aga tgt gac atc cag atg acc cag tct cca tcc ttc      96
Leu Ser Gly Ala Arg Cys Asp Ile Gln Met Thr Gln Ser Pro Ser Phe
            20                  25                  30 cct gtc tgc atc tgt agg aga cag agt cac cat cac ttg cca ggc gag     144
Pro Val Cys Ile Cys Arg Arg Gln Ser His His His Leu Pro Gly Glu
        35                  40                  45 tca gga cat tca cca cta ttt aaa ttg gta tca gca gaa acc agg gaa     192
Ser Gly His Ser Pro Leu Phe Lys Leu Val Ser Ala Glu Thr Arg Glu
    50                  55                  60 agc cct aag ctc ctg atc tac gat gca tcc aat ttg gaa aca ggg tcc     240
Ser Pro Lys Leu Leu Ile Tyr Asp Ala Ser Asn Leu Glu Thr Gly Ser
 65                  70                  75                  80 cat cac ggt tca gtg gaa gtg gat ctg gga cag att tta ctt tca cca     288
His His Gly Ser Val Glu Val Asp Leu Gly Gln Ile Leu Leu Ser Pro
                85                  90                  95 tca gca gcc tgc agc tct gaa gat att gca aca tat tac tgt caa cag     336
Ser Ala Ala Cys Ser Ser Glu Asp Ile Ala Thr Tyr Tyr Cys Gln Gln
            100                 105                 110 tat aat aat ctc atc acc ttc ggc caa ggg aca cga ctg gag att aaa     384
Tyr Asn Asn Leu Ile Thr Phe Gly Gln Gly Thr Arg Leu Glu Ile Lys
        115                 120                 125 cga act gtg gct gca cca tct                                         405
Arg Thr Val Ala Ala Pro Ser
    130                 135

<210> SEQ ID NO 20
<211> LENGTH: 135
<212> TYPE: PRT
<213> ORGANISM: Homo sapiens

<400> SEQUENCE: 20

Met Asp Met Arg Val Pro Ala Gln Leu Leu Gly Leu Leu Leu Leu Trp
 1               5                  10                  15

Leu Ser Gly Ala Arg Cys Asp Ile Gln Met Thr Gln Ser Pro Ser Phe
            20                  25                  30

Pro Val Cys Ile Cys Arg Arg Gln Ser His His His Leu Pro Gly Glu
        35                  40                  45

Ser Gly His Ser Pro Leu Phe Lys Leu Val Ser Ala Glu Thr Arg Glu
    50                  55                  60

Ser Pro Lys Leu Leu Ile Tyr Asp Ala Ser Asn Leu Glu Thr Gly Ser
 65                  70                  75                  80

His His Gly Ser Val Glu Val Asp Leu Gly Gln Ile Leu Leu Ser Pro
                85                  90                  95

Ser Ala Ala Cys Ser Ser Glu Asp Ile Ala Thr Tyr Tyr Cys Gln Gln
            100                 105                 110

Tyr Asn Asn Leu Ile Thr Phe Gly Gln Gly Thr Arg Leu Glu Ile Lys
        115                 120                 125

Arg Thr Val Ala Ala Pro Ser
    130                 135
```

<210> SEQ ID NO 21
<211> LENGTH: 387
<212> TYPE: DNA
<213> ORGANISM: Homo sapiens
<220> FEATURE:
<221> NAME/KEY: CDS
<222> LOCATION: (1)..(387)
<221> NAME/KEY: sig_peptide
<222> LOCATION: (1)..(47)
<223> OTHER INFORMATION: Initiation codon and a portion of a signal sequence are lacked.
<221> NAME/KEY: V_region
<222> LOCATION: (48)..(335)

<400> SEQUENCE: 21

| | | | | | | | | | | | | | | | | |
|---|---|---|---|---|---|---|---|---|---|---|---|---|---|---|---|---|
| gat | agg | gtc | cta | ggg | gtc | ctg | atg | gtt | ggg | ttt | tcg | gtg | ccg | gat | gag | 48 |
| Asp | Arg | Val | Leu | Gly | Val | Leu | Met | Val | Gly | Phe | Ser | Val | Pro | Asp | Glu | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| aac | atc | cag | atg | acc | cag | tat | cca | tct | ccc | tgt | ctg | cat | acc | tgt | agg | 96 |
| Asn | Ile | Gln | Met | Thr | Gln | Tyr | Pro | Ser | Pro | Cys | Leu | His | Thr | Cys | Arg | |
| | | | 20 | | | | | 25 | | | | | 30 | | | |

| | | | | | | | | | | | | | | | | |
|---|---|---|---|---|---|---|---|---|---|---|---|---|---|---|---|---|
| aga | cag | agt | cac | cat | cac | ttg | cca | gag | cga | gct | cag | gac | att | cac | cac | 144 |
| Arg | Gln | Ser | His | His | His | Leu | Pro | Glu | Arg | Ala | Gln | Asp | Ile | His | His | |
| | | 35 | | | | | 40 | | | | | 45 | | | | |

| | | | | | | | | | | | | | | | | |
|---|---|---|---|---|---|---|---|---|---|---|---|---|---|---|---|---|
| tat | cta | aat | tgg | tat | cag | cag | aaa | cca | ggg | aaa | gcc | cta | agc | tct | gat | 192 |
| Tyr | Leu | Asn | Trp | Tyr | Gln | Gln | Lys | Pro | Gly | Lys | Ala | Leu | Ser | Ser | Asp | |
| | 50 | | | | | 55 | | | | | 60 | | | | | |

| | | | | | | | | | | | | | | | | |
|---|---|---|---|---|---|---|---|---|---|---|---|---|---|---|---|---|
| cta | cga | tgc | atc | caa | ttt | gga | aac | agg | gtc | cca | tca | cgg | ttc | agt | gga | 240 |
| Leu | Arg | Cys | Ile | Gln | Phe | Gly | Asn | Arg | Val | Pro | Ser | Arg | Phe | Ser | Gly | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| agt | gga | tct | ggg | aca | gat | tct | act | tca | cca | tca | gca | gcc | tgc | agc | tct | 288 |
| Ser | Gly | Ser | Gly | Thr | Asp | Ser | Thr | Ser | Pro | Ser | Ala | Ala | Cys | Ser | Ser | |
| | | | | 85 | | | | | 90 | | | | | 95 | | |

| | | | | | | | | | | | | | | | | |
|---|---|---|---|---|---|---|---|---|---|---|---|---|---|---|---|---|
| gaa | gat | att | gca | aca | tat | tac | tgt | caa | cag | tat | aat | aat | ctc | atc | acc | 336 |
| Glu | Asp | Ile | Ala | Thr | Tyr | Tyr | Cys | Gln | Gln | Tyr | Asn | Asn | Leu | Ile | Thr | |
| | | | 100 | | | | | 105 | | | | | 110 | | | |

| | | | | | | | | | | | | | | | | |
|---|---|---|---|---|---|---|---|---|---|---|---|---|---|---|---|---|
| ttc | ggc | caa | ggg | aca | cga | ctg | gag | att | aaa | cga | act | gtg | gct | gca | cca | 384 |
| Phe | Gly | Gln | Gly | Thr | Arg | Leu | Glu | Ile | Lys | Arg | Thr | Val | Ala | Ala | Pro | |
| | | 115 | | | | | 120 | | | | | 125 | | | | |

| | | |
|---|---|---|
| tct | | 387 |
| Ser | | |

<210> SEQ ID NO 22
<211> LENGTH: 129
<212> TYPE: PRT
<213> ORGANISM: Homo sapiens

<400> SEQUENCE: 22

Asp Arg Val Leu Gly Val Leu Met Val Gly Phe Ser Val Pro Asp Glu
 1               5                  10                  15

Asn Ile Gln Met Thr Gln Tyr Pro Ser Pro Cys Leu His Thr Cys Arg
             20                  25                  30

Arg Gln Ser His His His Leu Pro Glu Arg Ala Gln Asp Ile His His
         35                  40                  45

Tyr Leu Asn Trp Tyr Gln Gln Lys Pro Gly Lys Ala Leu Ser Ser Asp
     50                  55                  60

Leu Arg Cys Ile Gln Phe Gly Asn Arg Val Pro Ser Arg Phe Ser Gly
 65                  70                  75                  80

Ser Gly Ser Gly Thr Asp Ser Thr Ser Pro Ser Ala Ala Cys Ser Ser
                 85                  90                  95

```
Glu Asp Ile Ala Thr Tyr Tyr Cys Gln Gln Tyr Asn Asn Leu Ile Thr
            100                 105                 110
Phe Gly Gln Gly Thr Arg Leu Glu Ile Lys Arg Thr Val Ala Ala Pro
        115                 120                 125
Ser
```

```
<210> SEQ ID NO 23
<211> LENGTH: 411
<212> TYPE: DNA
<213> ORGANISM: Homo sapiens
<220> FEATURE:
<221> NAME/KEY: CDS
<222> LOCATION: (1)..(411)
<221> NAME/KEY: sig_peptide
<222> LOCATION: (1)..(66)
<221> NAME/KEY: V_region
<222> LOCATION: (67)..(356)

<400> SEQUENCE: 23
```

```
atg gac atg agg gtc cct gct cag ctc ctg ggg ctc ctg ctg ctc tgg      48
Met Asp Met Arg Val Pro Ala Gln Leu Leu Gly Leu Leu Leu Leu Trp
 1               5                  10                  15 ctc tca ggt gcc aga tgt gac atc cag atg acc cag tct cca tcc tcc      96
Leu Ser Gly Ala Arg Cys Asp Ile Gln Met Thr Gln Ser Pro Ser Ser
            20                  25                  30 ctg tct gca tct gta gga gac aga gtc acc atc act tgc cgg gca agt     144
Leu Ser Ala Ser Val Gly Asp Arg Val Thr Ile Thr Cys Arg Ala Ser
        35                  40                  45 cag agc att agc agc tat tta aat tgg tat cag cag aaa cca ggg aaa     192
Gln Ser Ile Ser Ser Tyr Leu Asn Trp Tyr Gln Gln Lys Pro Gly Lys
    50                  55                  60 gcc cct aag ctc ctg att tat gct gca tcc agt ttg caa agt ggg tcc     240
Ala Pro Lys Leu Leu Ile Tyr Ala Ala Ser Ser Leu Gln Ser Gly Ser
65                  70                  75                  80 cat caa ggt tca gtg gca gtg gat tat gcg aca gat ttc cat ttc tca     288
His Gln Gly Ser Val Ala Val Asp Tyr Ala Thr Asp Phe His Phe Ser
                85                  90                  95 cca tca gca gtt tgc cac ctg acg att ttg caa ctt act act gtc cac     336
Pro Ser Ala Val Cys His Leu Thr Ile Leu Gln Leu Thr Thr Val His
            100                 105                 110 aga gtt aca gta tcc cat tca ctt tcg gcc ctg ggg acc aaa gtg gat     384
Arg Val Thr Val Ser His Ser Leu Ser Ala Leu Gly Thr Lys Val Asp
        115                 120                 125 agc aaa cga act gtg gct gca cca tct                                  411
Ser Lys Arg Thr Val Ala Ala Pro Ser
    130                 135
```

```
<210> SEQ ID NO 24
<211> LENGTH: 137
<212> TYPE: PRT
<213> ORGANISM: Homo sapiens

<400> SEQUENCE: 24
```

```
Met Asp Met Arg Val Pro Ala Gln Leu Leu Gly Leu Leu Leu Leu Trp
 1               5                  10                  15

Leu Ser Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Ser Ile Ser Ser Tyr Leu Asn Trp Tyr Gln Gln Lys Pro Gly Lys
    50                  55                  60
```

-continued

```
Ala Pro Lys Leu Leu Ile Tyr Ala Ala Ser Ser Leu Gln Ser Gly Ser
 65                  70                  75                  80

His Gln Gly Ser Val Ala Val Asp Tyr Ala Thr Asp Phe His Phe Ser
                 85                  90                  95

Pro Ser Ala Val Cys His Leu Thr Ile Leu Gln Leu Thr Thr Val His
            100                 105                 110

Arg Val Thr Val Ser His Ser Leu Ser Ala Leu Gly Thr Lys Val Asp
            115                 120                 125

Ser Lys Arg Thr Val Ala Ala Pro Ser
    130                 135

<210> SEQ ID NO 25
<211> LENGTH: 27
<212> TYPE: DNA
<213> ORGANISM: Artificial Sequence
<220> FEATURE:
<223> OTHER INFORMATION: Description of Artificial Sequence:
      Artificially synthesized adaptor sequence
<221> NAME/KEY: misc_difference
<222> LOCATION: (1)..(27)

<400> SEQUENCE: 25
ccatcctaat acgactcact atagggc                                      27

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence:
      Artificially synthesized primer sequence
<221> NAME/KEY: primer_bind
<222> LOCATION: (1)..(25)

<400> SEQUENCE: 26
ccagggccgc tgtgctctcg gaggt                                        25

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence:
      Artificially synthesized primer sequence
<221> NAME/KEY: primer_bind
<222> LOCATION: (1)..(23)

<400> SEQUENCE: 27
gggggtcagg ctggaactga gga                                          23
```